(12) United States Patent
Davis et al.

(10) Patent No.: US 10,682,287 B2
(45) Date of Patent: Jun. 16, 2020

(54) DOSING CONTROL COUPLING FOR ENTERAL FLUID TRANSFER AND ENTERAL COUPLINGS AND SYRINGES

(71) Applicant: NEOMED, INC., Woodstock, GA (US)

(72) Inventors: Benjamin M. Davis, Woodstock, GA (US); Aaron N. Ingram, Canton, GA (US); Duane Webb, Roswell, GA (US); Mariann Cary, Canton, GA (US)

(73) Assignee: NeoMed, Inc., Woodstock, GA (US)

( * ) Notice: Subject to any disclaimer, the term of this patent is extended or adjusted under 35 U.S.C. 154(b) by 0 days.

(21) Appl. No.: 15/659,323

(22) Filed: Jul. 25, 2017

(65) Prior Publication Data

US 2017/0319438 A1 Nov. 9, 2017

Related U.S. Application Data

(63) Continuation-in-part of application No. 15/210,282, filed on Jul. 14, 2016, now Pat. No. 10,420,709.

(Continued)

(51) Int. Cl.
*A61J 15/00* (2006.01)
*A61M 5/34* (2006.01)
(Continued)

(52) U.S. Cl.
CPC ......... *A61J 15/0026* (2013.01); *A61J 7/0053* (2013.01); *A61M 5/3134* (2013.01);
(Continued)

(58) Field of Classification Search
CPC .. A61J 15/0026; A61J 15/0076; A61J 7/0053; A61J 1/1475; A61J 15/0084;
(Continued)

(56) References Cited

U.S. PATENT DOCUMENTS

| 1,704,921 A | 3/1929 | Nicoll |
| 2,708,438 A | 5/1955 | Cohen |

(Continued)

FOREIGN PATENT DOCUMENTS

| CA | 2548976 A1 | 12/2007 |
| DE | 2108381 A1 | 8/1972 |

(Continued)

OTHER PUBLICATIONS

Kasper, Debby Non-patent literature "Enfit enteral connections: Are you ready?", Mar. 26, 2015.*

(Continued)

*Primary Examiner* — Kevin C Sirmons
*Assistant Examiner* — Alexandra Lalonde
(74) *Attorney, Agent, or Firm* — Dority & Manning, P.A.

(57) ABSTRACT

An enteral dosing control coupling comprising a cylindrical collar defining a hollow internal chamber and a lumen extension tip projecting axially into the internal chamber, the lumen extension tip defining an internal lumen extending therethrough. In example forms, the lumen extension tip is integrally formed with the cylindrical collar. In other example forms, the lumen extension tip is a separate piece and is removably engageable within the cylindrical collar. In some example forms, the present invention relates to syringes, connectors, couplings, etc. having ISO 80369-3 formatted couplings. In other example forms, the present invention relates to connectors, couplings, etc. for adapting coupling formats other than the ISO 80369-3 coupling format to the ISO 80369-3 coupling format.

20 Claims, 37 Drawing Sheets

Related U.S. Application Data

(60) Provisional application No. 62/376,006, filed on Aug. 17, 2016, provisional application No. 62/366,399, filed on Jul. 25, 2016, provisional application No. 62/350,934, filed on Jun. 16, 2016, provisional application No. 62/207,120, filed on Aug. 19, 2015, provisional application No. 62/192,454, filed on Jul. 14, 2015.

(51) Int. Cl.
*A61M 5/31* (2006.01)
*A61J 7/00* (2006.01)
*A61M 39/12* (2006.01)
*A61M 39/10* (2006.01)

(52) U.S. Cl.
CPC ........ *A61M 5/345* (2013.01); *A61M 39/1011* (2013.01); *A61M 39/12* (2013.01); *A61J 15/0092* (2013.01); *A61M 2005/3104* (2013.01); *A61M 2005/3106* (2013.01); *A61M 2039/1077* (2013.01); *A61M 2039/1094* (2013.01); *A61M 2202/0482* (2013.01)

(58) Field of Classification Search
CPC .. A61J 15/0088; A61M 5/3134; A61M 5/345; A61M 2039/1094; A61M 5/178; A61M 5/1782; A61M 5/3129; A61M 2039/1077; A61M 2039/1083; A61M 2039/1088; A61M 36/1011; A61M 36/12; A61M 36/10; A61M 39/1011; A61M 39/12; A61M 39/10
See application file for complete search history.

(56) References Cited

U.S. PATENT DOCUMENTS

| | | |
|---|---|---|
| 2,869,543 A | 1/1959 | Ratcliff et al. |
| 2,939,459 A | 6/1960 | Lazarte et al. |
| 3,326,215 A | 6/1967 | Sarnoff et al. |
| 3,370,754 A | 2/1968 | Cook et al. |
| 3,489,147 A | 1/1970 | Shaw |
| 3,557,787 A | 1/1971 | Cohen |
| 3,570,486 A | 3/1971 | Engelsher et al. |
| 3,572,337 A | 3/1971 | Schunk |
| 3,659,749 A | 5/1972 | Schwartz |
| 3,678,931 A | 7/1972 | Cohen |
| 3,680,558 A | 8/1972 | Kapelowitz |
| 3,682,174 A | 8/1972 | Cohen |
| 3,684,136 A | 8/1972 | Baumann |
| 3,685,514 A | 8/1972 | Cheney |
| 3,756,390 A | 9/1973 | Abbey et al. |
| 3,885,562 A | 5/1975 | Lampkin |
| 3,885,710 A | 5/1975 | Cohen |
| 3,896,805 A | 7/1975 | Weingarten |
| 3,921,633 A | 11/1975 | Tischlinger |
| 4,043,334 A | 8/1977 | Brown et al. |
| 4,046,145 A | 9/1977 | Choksi et al. |
| 4,171,699 A | 10/1979 | Jones et al. |
| 4,254,768 A | 3/1981 | Ty |
| 4,351,334 A | 9/1982 | Inglefield, Jr. |
| D267,536 S | 1/1983 | Findlay |
| 4,464,174 A | 8/1984 | Ennis |
| D282,807 S | 3/1986 | Hasse |
| D287,877 S | 1/1987 | Holewinski et al. |
| 4,639,248 A | 1/1987 | Schweblin |
| 4,693,706 A | 9/1987 | Ennis, III |
| 4,702,737 A | 10/1987 | Pizzino |
| D320,084 S | 9/1991 | Stewart et al. |
| D323,031 S | 1/1992 | Ahlstrand et al. |
| 5,115,816 A | 5/1992 | Lee |
| D330,862 S | 11/1992 | Shibley et al. |
| 5,176,415 A | 1/1993 | Choksi |
| 5,188,599 A | 2/1993 | Botich et al. |
| 5,244,122 A | 9/1993 | Botts |
| 5,279,566 A | 1/1994 | Kline, Jr. et al. |
| 5,286,067 A | 2/1994 | Choksi |
| 5,372,586 A | 12/1994 | Haber et al. |
| 5,395,345 A | 3/1995 | Gross |
| 5,395,348 A | 3/1995 | Ryan |
| D369,214 S | 4/1996 | Nason |
| 5,533,973 A | 7/1996 | Piontek et al. |
| 5,569,193 A | 10/1996 | Hofstetter et al. |
| D383,205 S | 9/1997 | Pagay et al. |
| 5,704,918 A | 1/1998 | Higashikawa |
| 5,779,668 A | 7/1998 | Grabenkort |
| 5,785,682 A | 7/1998 | Grabenkort |
| 5,824,012 A | 10/1998 | Burchett et al. |
| 5,836,919 A | 11/1998 | Skurka et al. |
| 5,843,042 A | 12/1998 | Ren |
| 5,876,379 A | 3/1999 | Beauvais et al. |
| 5,891,165 A | 4/1999 | Buckner |
| 6,010,481 A | 1/2000 | Lee |
| D420,129 S | 2/2000 | McMahon |
| 6,126,644 A | 10/2000 | Naganuma et al. |
| 6,126,679 A | 10/2000 | Botts |
| 6,164,044 A | 12/2000 | Porfano et al. |
| 6,165,153 A * | 12/2000 | Kashmer ............. A61M 5/5013 604/110 |
| D436,661 S | 1/2001 | Berry |
| 6,200,295 B1 | 3/2001 | Burchett et al. |
| D445,176 S | 7/2001 | Landers |
| 6,270,519 B1 | 8/2001 | Botts |
| D447,797 S | 9/2001 | Odell et al. |
| 6,391,008 B1 | 5/2002 | Tsai |
| 6,394,983 B1 | 5/2002 | Mayoral et al. |
| D460,820 S | 7/2002 | Niedospial, Jr. |
| D461,243 S | 8/2002 | Niedospial, Jr. |
| 6,432,087 B1 | 8/2002 | Hoeck et al. |
| D462,761 S | 9/2002 | Swenson |
| D463,025 S | 9/2002 | Swenson |
| 6,544,233 B1 | 4/2003 | Fukui et al. |
| 6,689,106 B2 | 2/2004 | Bush, Jr. et al. |
| 6,752,782 B2 | 6/2004 | Liao |
| D504,512 S | 4/2005 | Fournier |
| D505,200 S | 5/2005 | Simpson et al. |
| 6,972,004 B2 | 12/2005 | La |
| 6,991,618 B2 | 1/2006 | Lau et al. |
| 7,018,089 B2 | 3/2006 | Wenz et al. |
| 7,032,764 B2 | 4/2006 | Viggiano |
| 7,172,085 B2 | 2/2007 | Beaudette |
| D542,406 S | 5/2007 | Knight et al. |
| D552,773 S | 10/2007 | Greenberg |
| 7,320,678 B2 | 1/2008 | Ruth et al. |
| 7,322,941 B2 | 1/2008 | Henshaw |
| 7,367,964 B2 | 5/2008 | Heinz et al. |
| D578,210 S | 10/2008 | Muta et al. |
| D581,048 S | 11/2008 | Kawamura |
| 7,455,661 B2 | 11/2008 | Barrelle et al. |
| D593,801 S | 6/2009 | Wilson et al. |
| 7,611,503 B2 | 11/2009 | Spohn et al. |
| 7,713,245 B2 | 5/2010 | Cipoletti et al. |
| D618,347 S | 6/2010 | Bradshaw |
| 7,842,217 B2 | 11/2010 | Enns et al. |
| D632,144 S | 2/2011 | Weisenbach |
| 7,879,002 B2 | 2/2011 | Jessop |
| D635,249 S | 3/2011 | Becker |
| 7,951,108 B2 | 5/2011 | Harper et al. |
| 8,016,795 B2 | 9/2011 | Barrelle et al. |
| D646,531 S | 10/2011 | Murphy |
| D649,242 S | 11/2011 | Kosinski et al. |
| D650,903 S | 12/2011 | Kosinski et al. |
| 8,075,523 B2 | 12/2011 | Wayman et al. |
| 8,231,585 B2 | 7/2012 | Heinz et al. |
| D675,540 S | 2/2013 | Montminy |
| 8,398,601 B2 | 3/2013 | Smith et al. |
| 8,465,461 B2 | 6/2013 | Wu et al. |
| D690,417 S | 9/2013 | Solomon |
| 8,540,682 B2 | 9/2013 | Carlyon |
| 8,540,683 B2 | 9/2013 | Williams, Jr. et al. |
| 8,568,365 B2 | 10/2013 | Reid |
| 8,684,979 B2 | 4/2014 | Deighan et al. |
| 8,740,858 B2 | 6/2014 | Kawamura |

(56) References Cited

U.S. PATENT DOCUMENTS

| | | | |
|---|---|---|---|
| 8,784,377 B2 | 7/2014 | Ranalletta et al. | |
| D713,028 S | 9/2014 | Yevmenenko | |
| D715,428 S | 10/2014 | Baid | |
| 8,870,833 B2 | 10/2014 | Lloyd et al. | |
| 8,882,725 B2 | 11/2014 | Davis | |
| D721,803 S | 1/2015 | Dubach | |
| 8,936,577 B2 | 1/2015 | Lee et al. | |
| 8,945,182 B2 | 2/2015 | Oates, II et al. | |
| 8,985,357 B1 | 3/2015 | Strayer et al. | |
| 8,992,505 B2 | 3/2015 | Thorne, Jr. et al. | |
| D726,305 S | 4/2015 | Furukawa | |
| 9,060,918 B1 | 6/2015 | Tomassini | |
| D739,524 S | 9/2015 | Zemel et al. | |
| 9,149,622 B2 | 10/2015 | Bonnet et al. | |
| D743,025 S | 11/2015 | Berler | |
| 9,272,099 B2 | 3/2016 | Limaye et al. | |
| 9,345,638 B2 | 5/2016 | Ferrara | |
| 9,408,971 B2 | 8/2016 | Carlyon | |
| 9,408,981 B2 | 8/2016 | Cowan | |
| D773,042 S | 11/2016 | Hwang et al. | |
| 9,504,630 B2 | 11/2016 | Liu | |
| 9,522,237 B2 | 12/2016 | Alheidt et al. | |
| D785,162 S | 4/2017 | Swisher et al. | |
| D792,969 S | 7/2017 | Taylor | |
| 9,839,750 B2 | 12/2017 | Limaye et al. | |
| 2002/0151851 A1 | 10/2002 | Fu | |
| 2003/0034264 A1 | 2/2003 | Hamai et al. | |
| 2003/0199816 A1 | 10/2003 | Ramming | |
| 2004/0133169 A1 | 7/2004 | Heinz et al. | |
| 2005/0038395 A1 | 2/2005 | Shih | |
| 2005/0177100 A1 | 8/2005 | Harper et al. | |
| 2005/0251096 A1* | 11/2005 | Armstrong | A61M 5/14546 604/218 |
| 2006/0161106 A1 | 7/2006 | Wu | |
| 2006/0189932 A1 | 8/2006 | Yang et al. | |
| 2006/0264824 A1 | 11/2006 | Swisher, III | |
| 2007/0005014 A1 | 1/2007 | Lin et al. | |
| 2007/0123822 A1 | 5/2007 | Wang et al. | |
| 2008/0021414 A1 | 1/2008 | Alheidt | |
| 2008/0045929 A1 | 2/2008 | Birnbach | |
| 2008/0114307 A1 | 5/2008 | Smith et al. | |
| 2008/0140020 A1 | 6/2008 | Shirley | |
| 2008/0223807 A1 | 9/2008 | Botts | |
| 2010/0030146 A1* | 2/2010 | Kakish | A61M 5/504 604/110 |
| 2012/0022457 A1 | 1/2012 | Silver | |
| 2012/0029471 A1 | 2/2012 | Lee et al. | |
| 2012/0150129 A1* | 6/2012 | Jin | A61M 39/10 604/240 |
| 2012/0245564 A1* | 9/2012 | Tekeste | A61M 5/3134 604/535 |
| 2012/0265150 A1 | 10/2012 | Frey et al. | |
| 2012/0302997 A1 | 11/2012 | Gardner et al. | |
| 2013/0030379 A1 | 1/2013 | Ingram et al. | |
| 2013/0090606 A1 | 4/2013 | Shams | |
| 2013/0098861 A1 | 4/2013 | Lair et al. | |
| 2013/0103003 A1 | 4/2013 | Capitaine et al. | |
| 2013/0144255 A1 | 6/2013 | Cohn | |
| 2013/0150797 A1 | 6/2013 | Lesch, Jr. | |
| 2013/0197485 A1 | 8/2013 | Gardner et al. | |
| 2014/0276442 A1 | 9/2014 | Haughey | |
| 2015/0073356 A1 | 3/2015 | Sasayama et al. | |
| 2015/0164744 A1 | 6/2015 | Ingram et al. | |
| 2015/0224031 A1 | 8/2015 | Methner | |
| 2015/0231038 A1 | 8/2015 | Oates, II et al. | |
| 2015/0238747 A1* | 8/2015 | Russo | A61M 39/1011 604/533 |
| 2016/0030293 A1* | 2/2016 | Dorsey | A61J 15/0096 604/506 |
| 2016/0067422 A1 | 3/2016 | Davis et al. | |
| 2016/0106928 A1 | 4/2016 | Davis et al. | |
| 2016/0159635 A1 | 6/2016 | Davis et al. | |
| 2016/0175201 A1 | 6/2016 | Schuessler | |
| 2016/0199591 A1 | 7/2016 | Matsui | |
| 2016/0250415 A1 | 9/2016 | Yagi et al. | |
| 2016/0279032 A1 | 9/2016 | Davis et al. | |
| 2016/0317393 A1 | 11/2016 | Davis et al. | |
| 2016/0354288 A1 | 12/2016 | Uehara et al. | |
| 2016/0354594 A1 | 12/2016 | Uehara et al. | |
| 2017/0014616 A1 | 1/2017 | Davis et al. | |
| 2017/0203045 A1 | 7/2017 | Ivosevic et al. | |
| 2018/0014998 A1* | 1/2018 | Yuki | A61M 5/34 |

FOREIGN PATENT DOCUMENTS

| | | |
|---|---|---|
| EP | 0148715 A1 | 7/1985 |
| EP | 1110568 A2 | 6/2001 |
| EP | 1447072 A1 | 8/2004 |
| EP | 1980282 A1 | 10/2008 |
| EP | 2269685 A2 | 1/2011 |
| FR | 1126718 A | 11/1956 |
| FR | 2720279 A1 | 12/1995 |
| FR | 2929854 A1 | 10/2009 |
| FR | 2930428 A1 | 10/2009 |
| JP | 2002126094 A | 5/2002 |
| WO | 9200717 A1 | 1/1992 |
| WO | 9803210 A2 | 1/1998 |
| WO | 9831410 A1 | 7/1998 |
| WO | 0130415 A2 | 5/2001 |
| WO | 03072162 A2 | 9/2003 |
| WO | 2011026156 A1 | 3/2011 |
| WO | 2013081699 A2 | 6/2013 |
| WO | WO 2013/081699 A2 | 6/2013 |
| WO | 2016154304 A1 | 9/2016 |
| WO | 2016205626 A1 | 12/2016 |
| WO | 2017011754 A1 | 1/2017 |

OTHER PUBLICATIONS

International Search Report & Written Opinion for PCT/US2017/043747; dated Nov. 2, 2017; 14 pgs.

Guide to New Enteral Feeding Connections; Covidien; Dec. 31, 2015; 4 pgs.

Invitation to Pay Additional Fees for PCT/US2017/042559; dated Oct. 16, 2017; 15 pgs.

10 ml Liquid Medicine Dispenser / Oral Syringe with Filler Tube; 1 pg; date unknown.

Alternative Syringes Low Displacement Option PowerPoint Presentation; Presented by Rork Swisher of Covidien; ISO 80369 Series Meeting; Berlin Germany; 11 pgs; Mar. 19, 2014.

Bostik Evo-Stik Adhesive Express Syringe; www.amazon.co.uk/Bostik-808546-Evo-Stik-Adhesive-Express/dp/B006O6DMFO; 1 pg; date unknown.

Brazilian Peel Syringe Applicator; www.amazon.com/Brazilian-Peel-Applications/dp/B003IIUN6W/ref=cm_cr_pr_product_top?ie=UTF8; 1 pg; date unknown.

Carrera, Amy Long, MS, RD, CNSC, CWCMS; Enfit: How to Transition to the New Feeding Tube Connectors; Shield Healthcare, Inc.; Feb. 4, 2015; 5 pgs.

"Enfit Update"; Feeding Tube Awareness Foundation; Feb. 2015; 5 pgs.

"Enteral Connectors: New Standards and Designs"; Pash, Elizabeth MS, RD, LDN; DNS Symposium; Baltimore, Maryland; Jun. 2015; 32 pgs.

International Search Report & Written Opinion for PCT/US2011/051338; dated Dec. 14, 2011; 20 pgs.

International Search Report & Written Opinion for PCT/US2016/023771; 17 pgs; dated Jun. 27, 2016.

International Search Report & Written Opinion for PCT/US2016/042248; dated Sep. 21, 2016; 10 pgs.

J-B Weld Epoxy Springe; www.lowes.com/pd_556898-81288-50112_0_?productID=50149636; 1 pg; date unknown.

Medi-Pals Oral Medication Dispenser; 1 pg; Jun. 19, 2012.

MediPop 3 in 1 Pacifier; 1 pg; date unknown.

NeoMed Enteral Syringe; 2007 (8 pgs).

Premier Safety Institute; New Enteral Feeding Products with ENFit Connectors: Implementation Timeline Delayed; SafetyShare; Jun. 18, 2015; 2 pgs.

(56) References Cited

OTHER PUBLICATIONS

New ISO Tubing Connector Standards: A Follow-Up to the Sentinel Event Alert Webinar PowerPoint Presention; www.iointcommission. org; 50 pgs; Dec. 3, 2014.
New Tube Feeding Connectors Webinar PowerPoint Presention; www.oley.org; 24 pgs; Jun. 24, 2014.
Oral Medication Dispenser; 1 pg; Jun. 19, 2012.
Oral Medication Nurser; 1 pg; Oct. 6, 2006.
Slap-Shot Flexible Oral Doser; 1 pg; date unknown.
Sulzer Dosing Syringe with Piston; www.directindustry.com/prod/sulzer-chemtech/product-28889-903259.html; 1 pg; date unknown.
Vygon Sales Sheet; 2014 (2 pgs).
Written Opinion for PCT/US2016/042248; dated Jul. 11, 2017; 8 pgs.
International Search Report & Written Opinion for PCT/US2017/042559; dated Dec. 7, 2017; 21 pgs.
International Search Report & Written Opinion for PCT/US2017/052321; dated Feb. 13, 2018; 17 pgs.

* cited by examiner

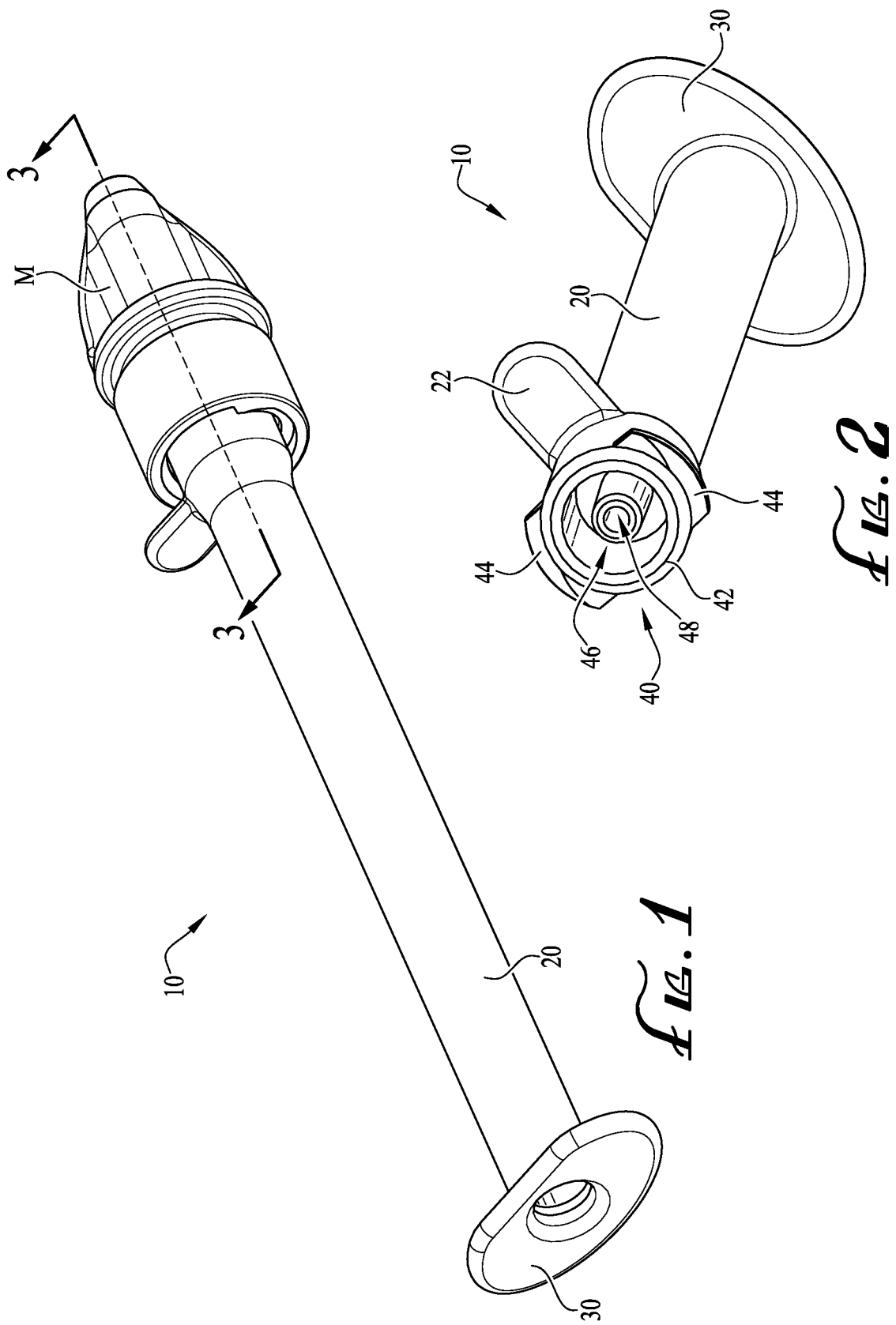

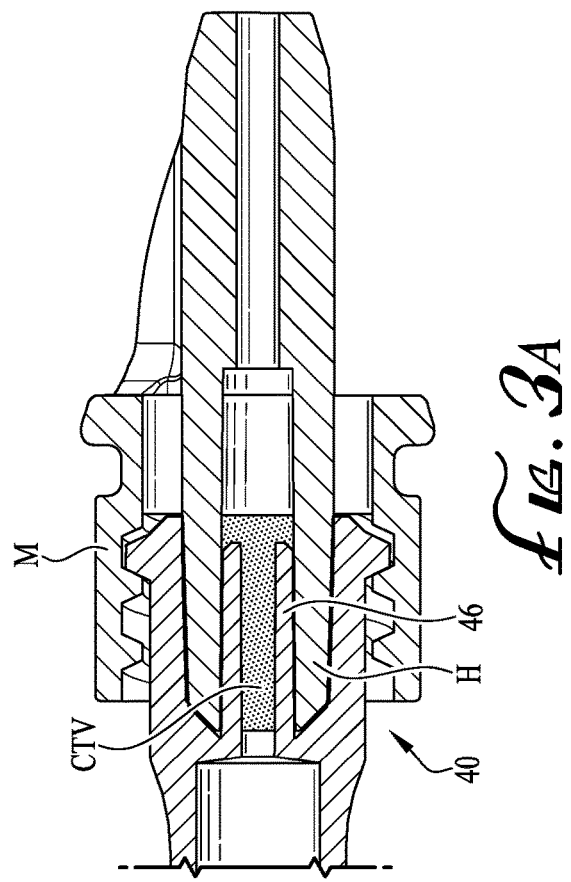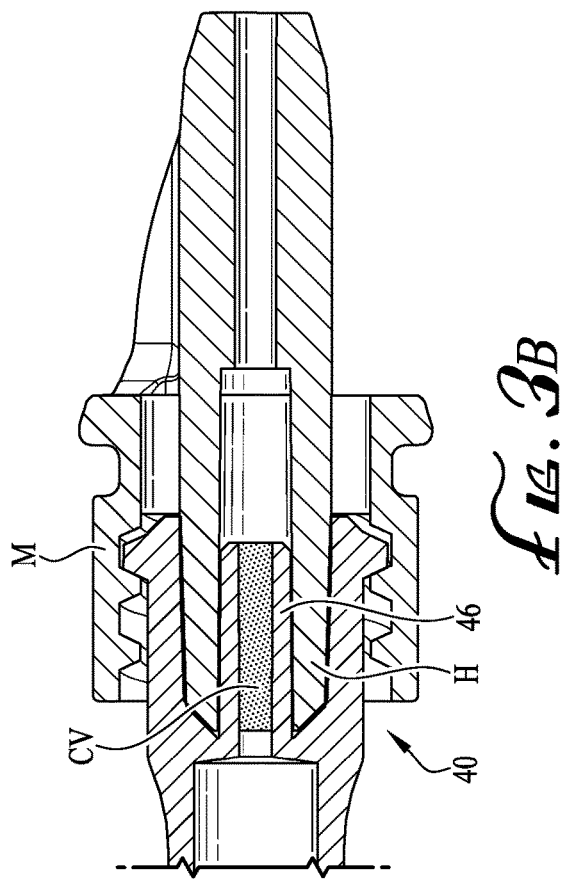

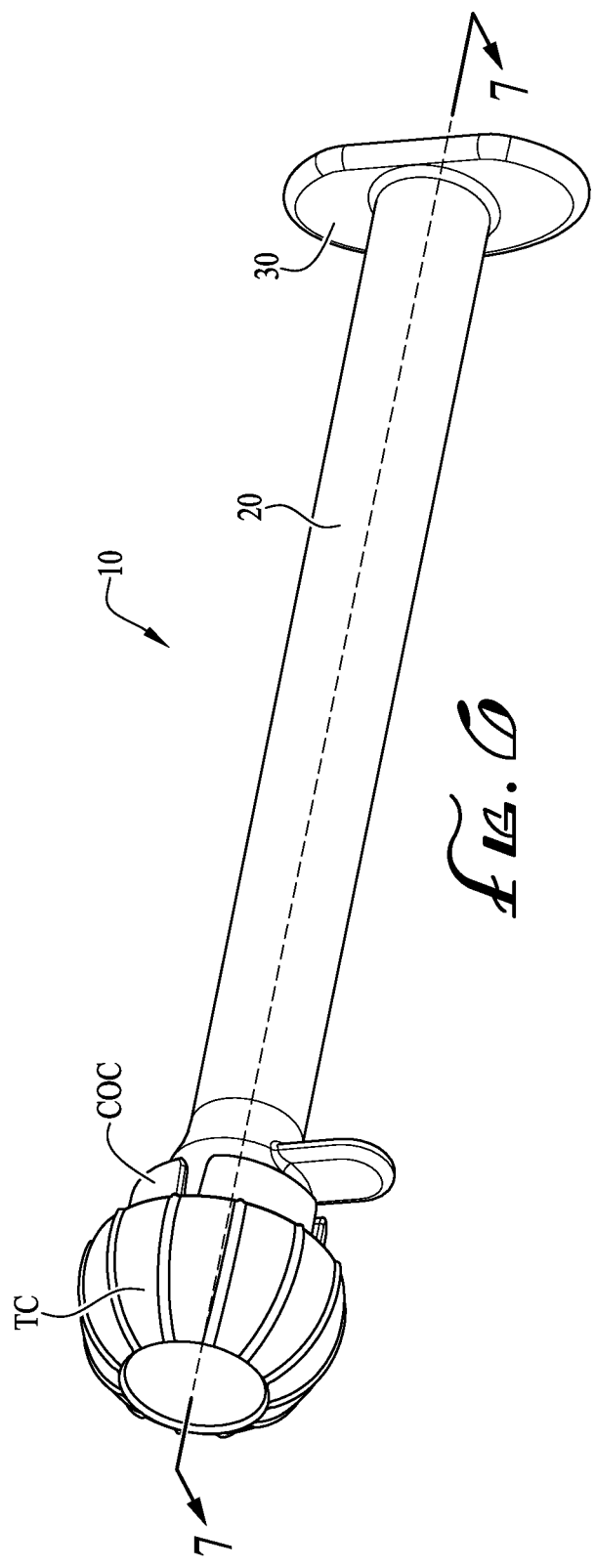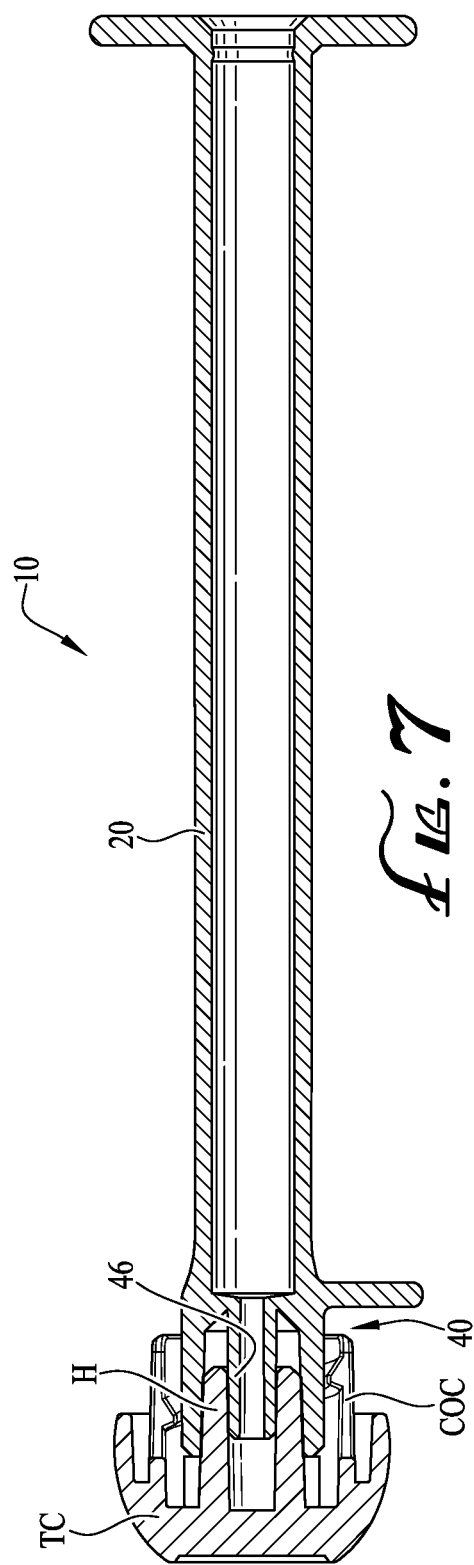

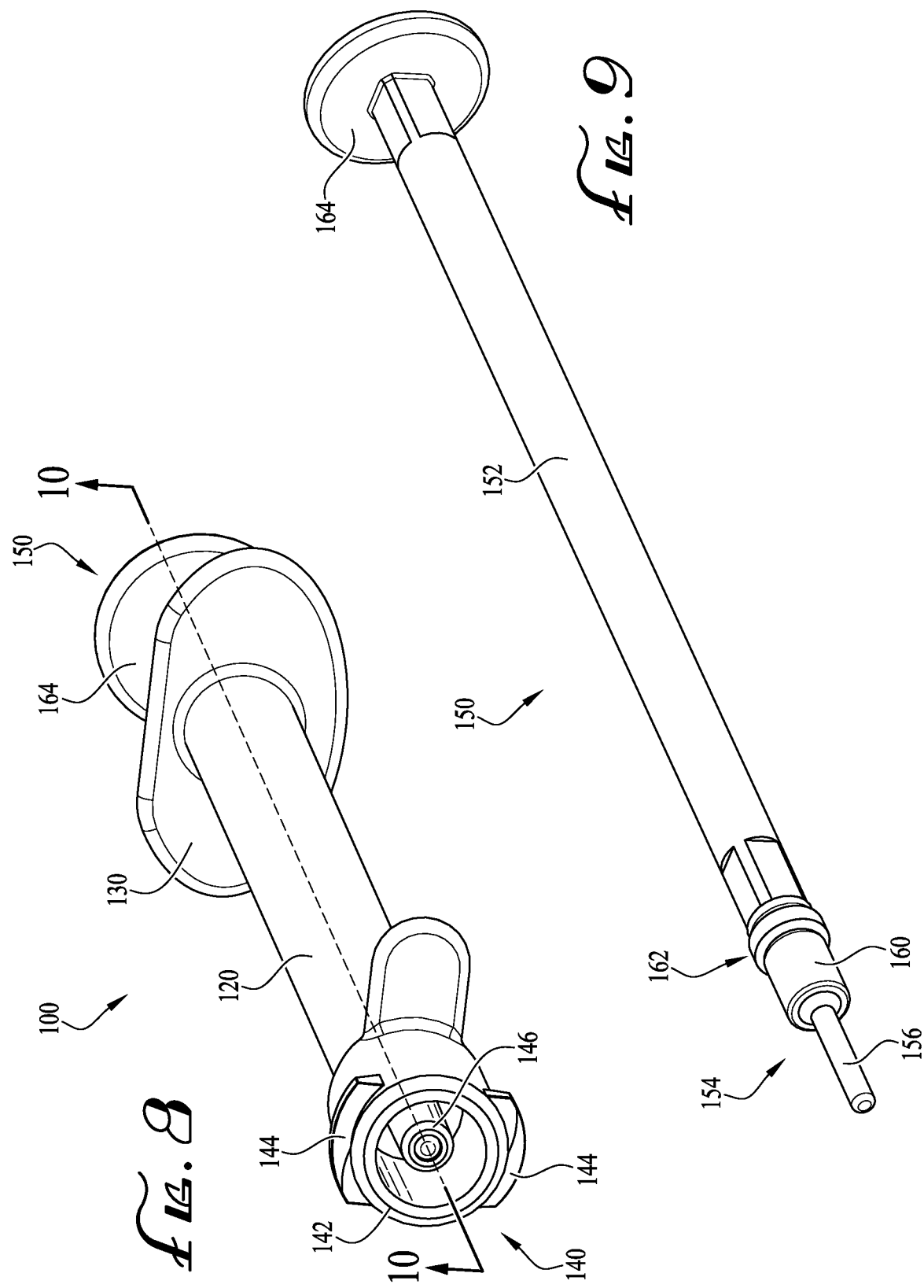

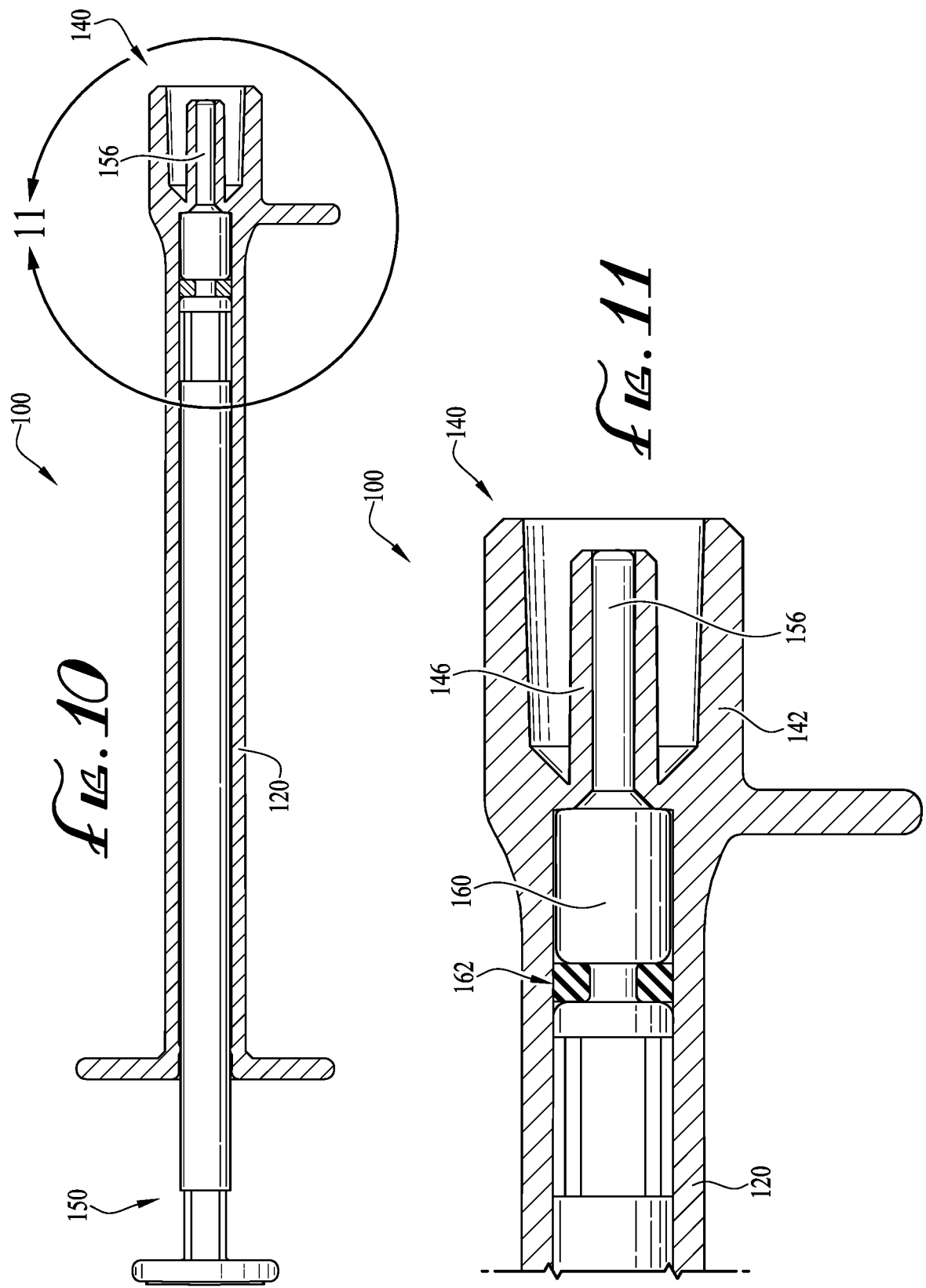

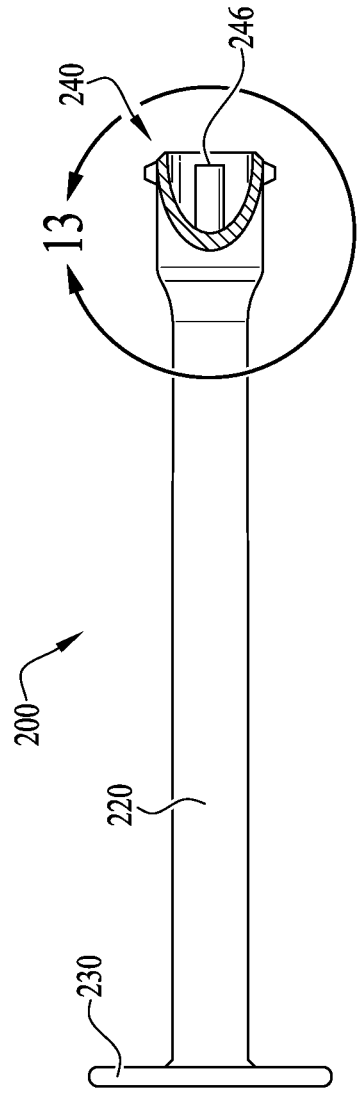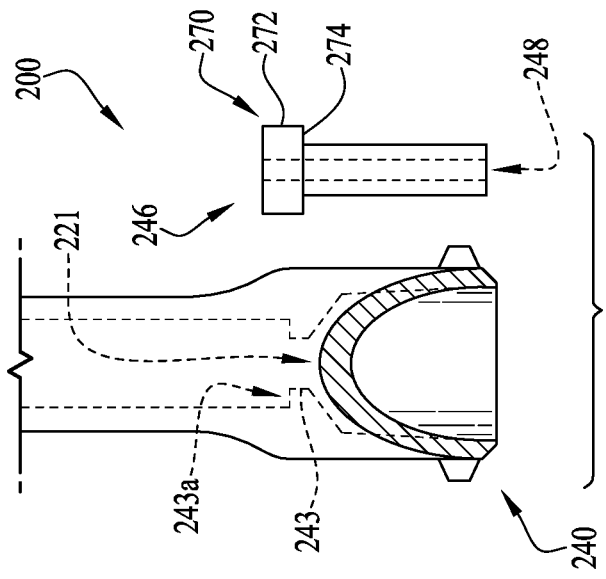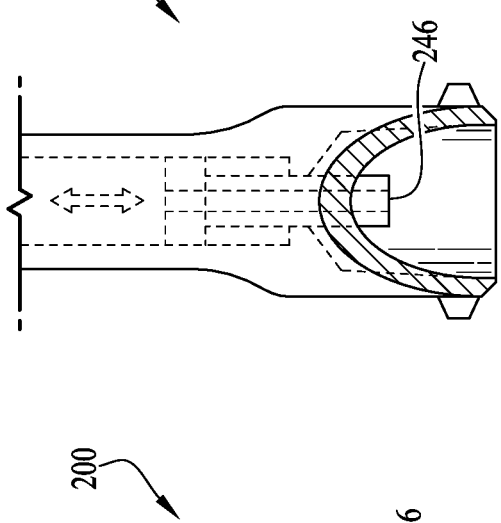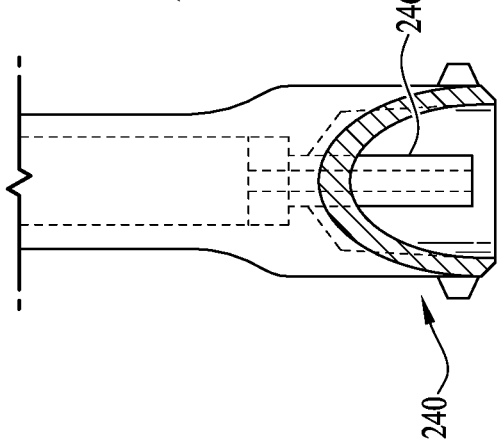

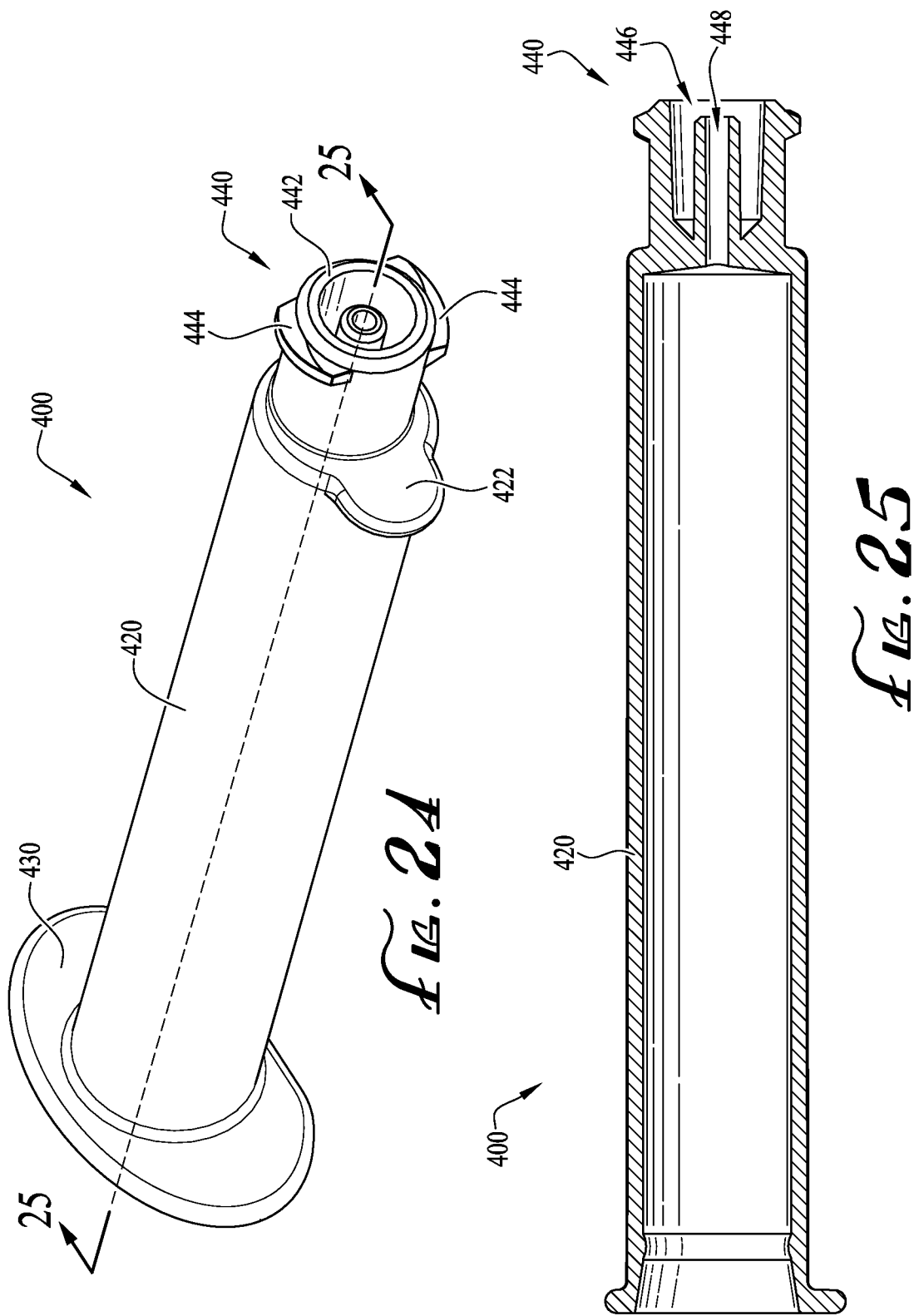

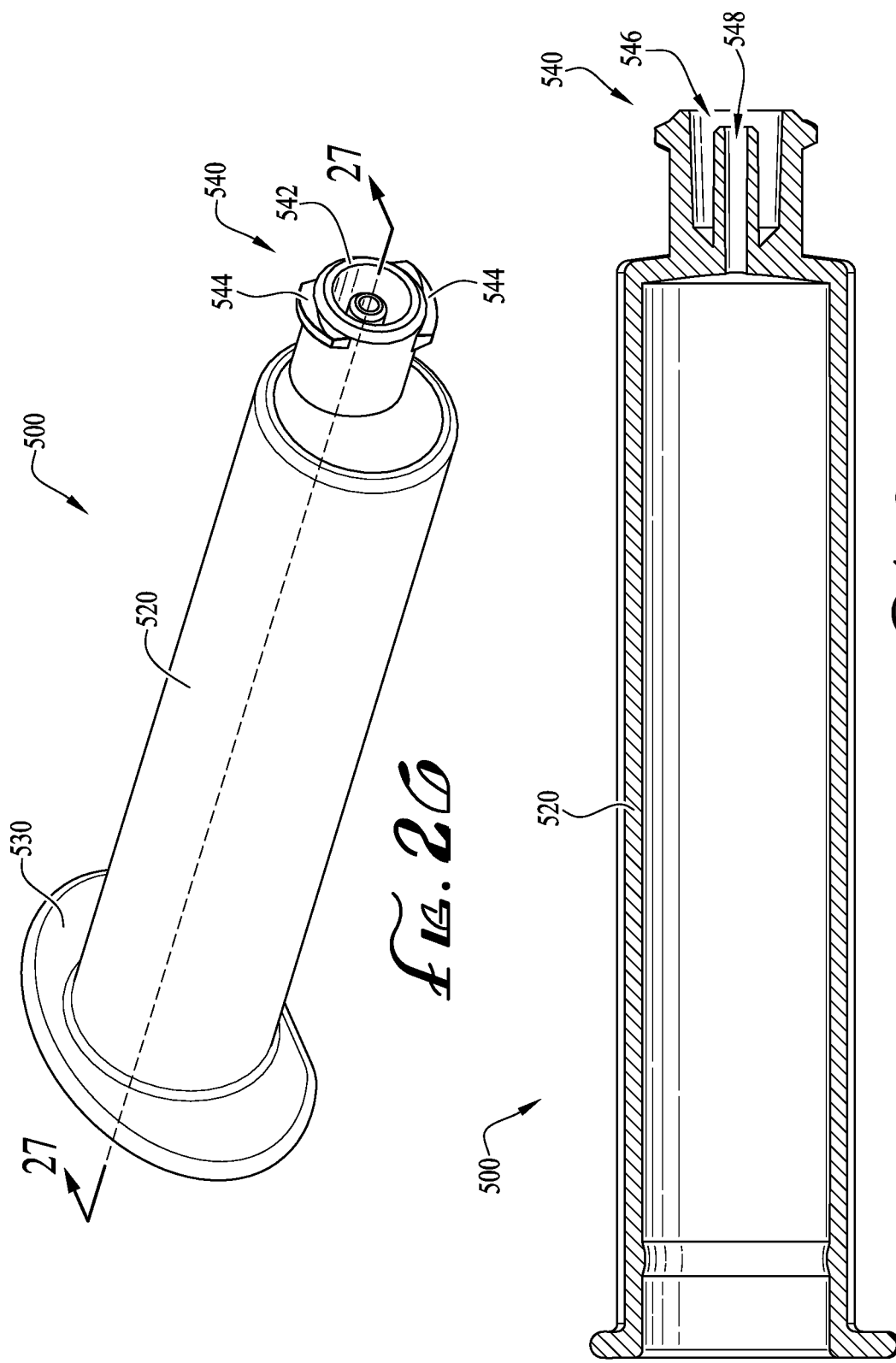

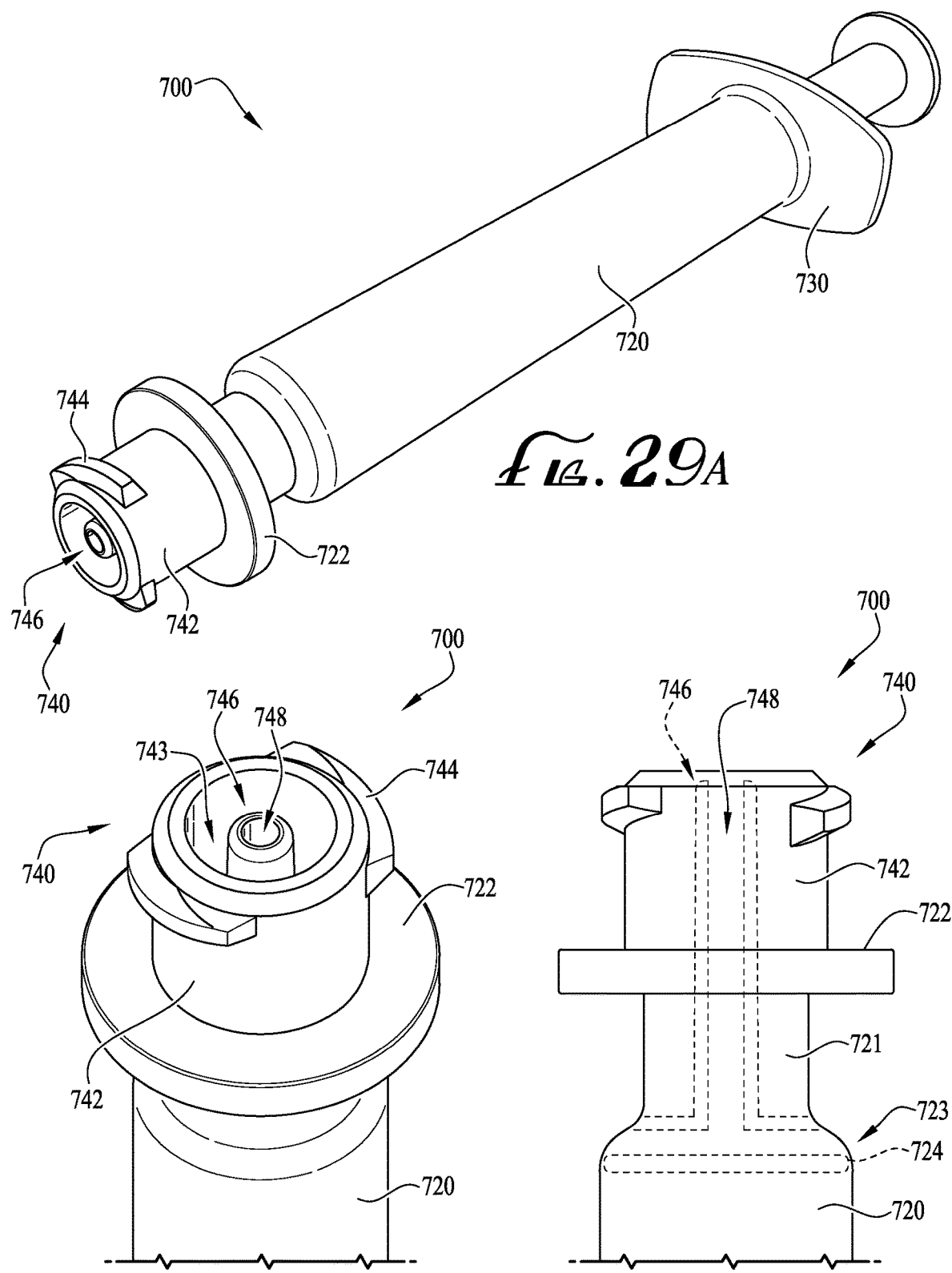

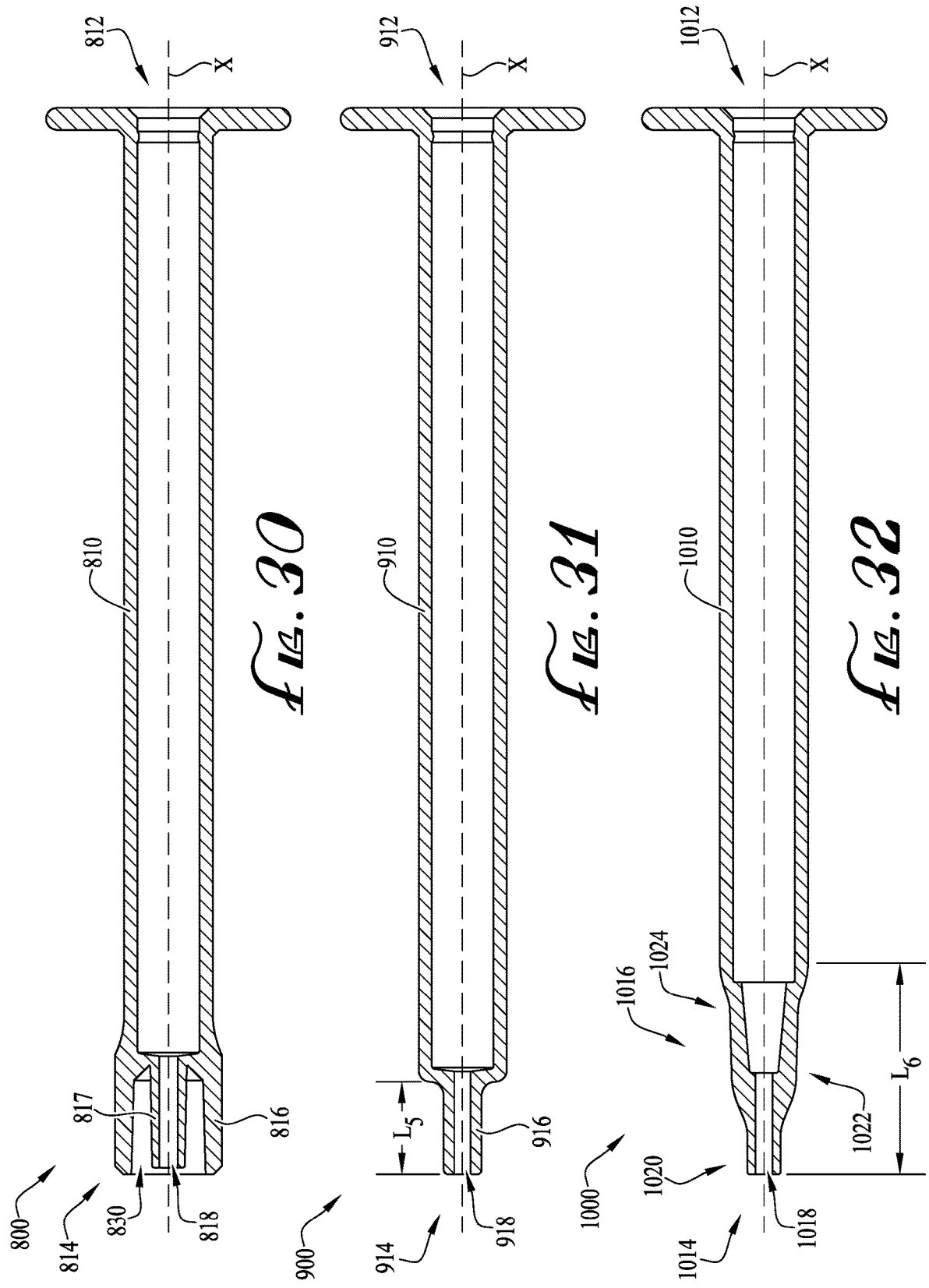

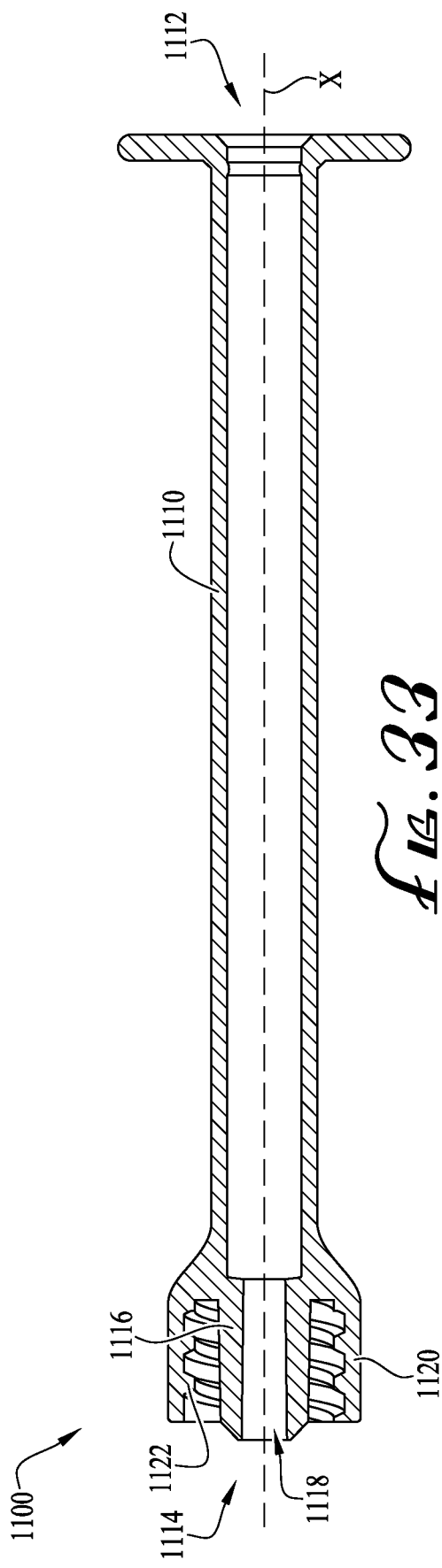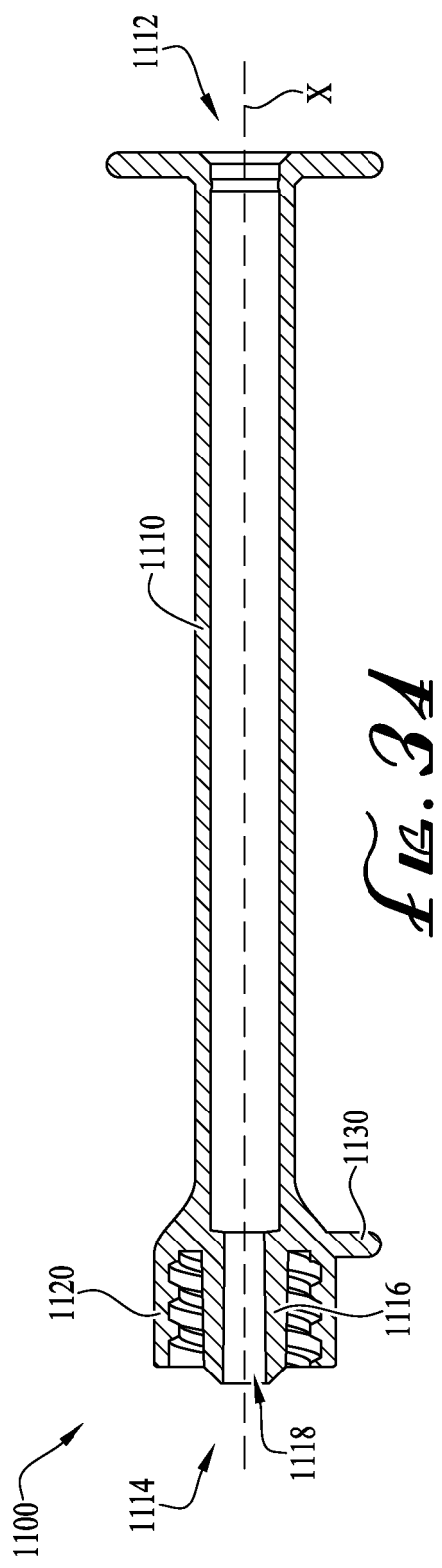

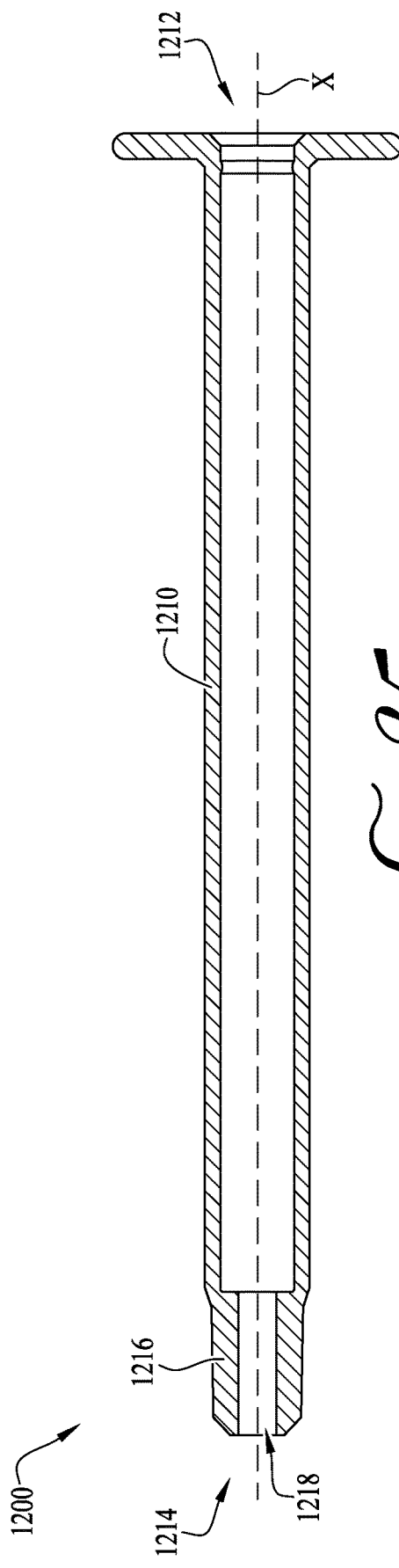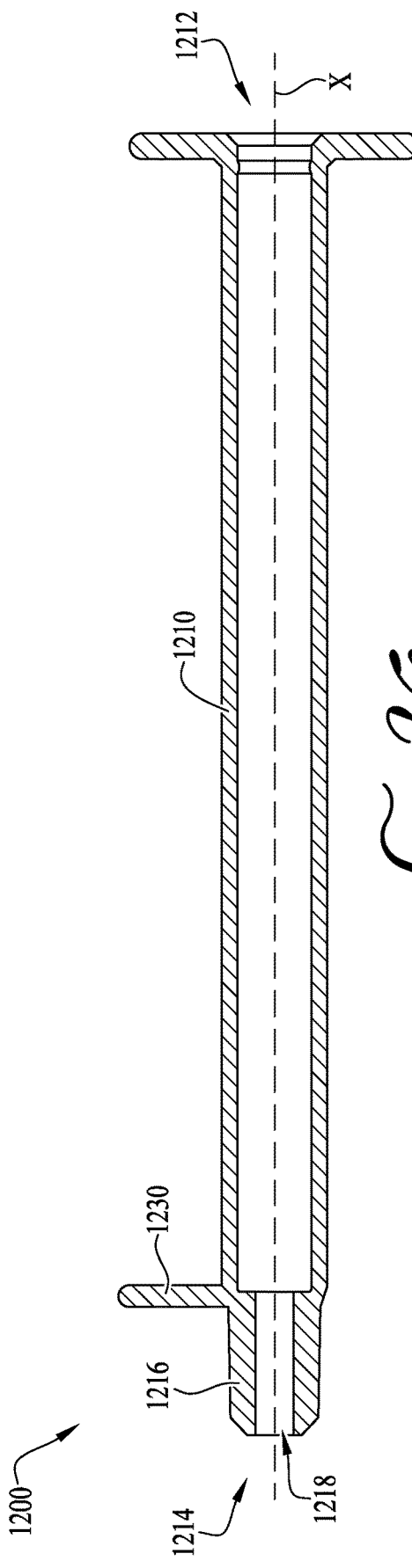

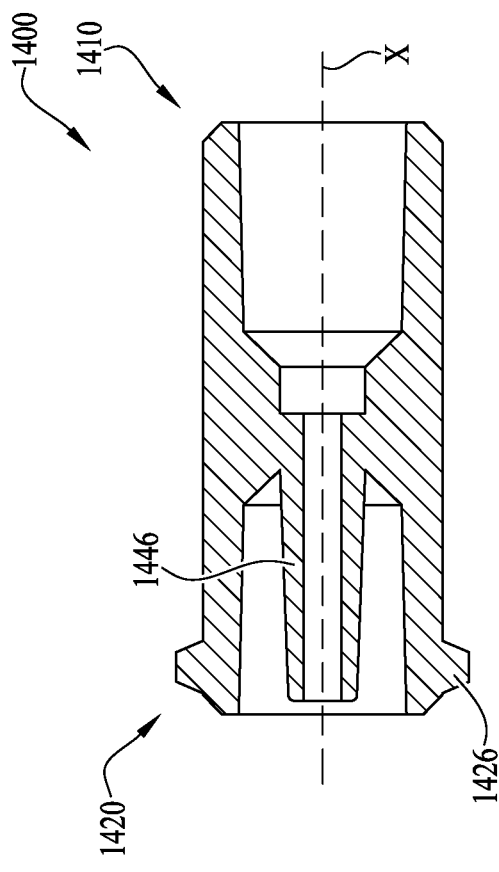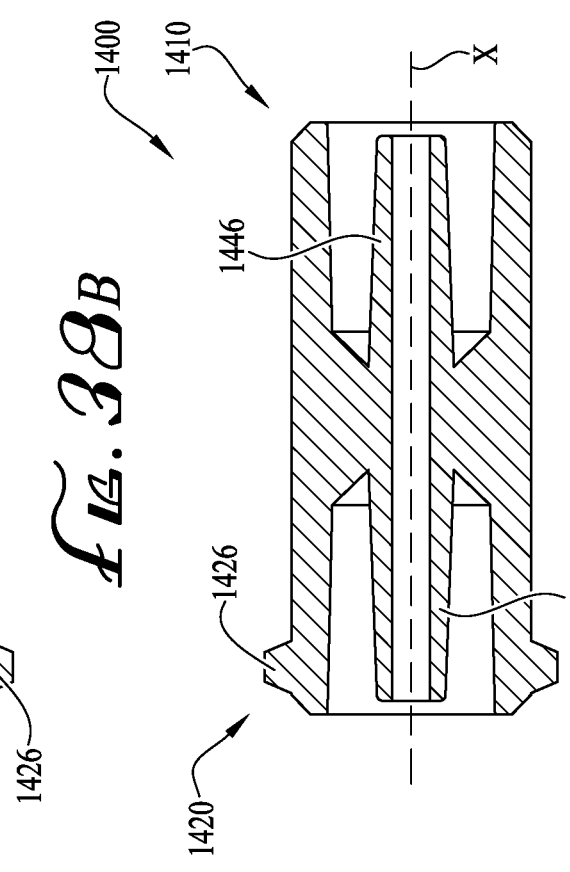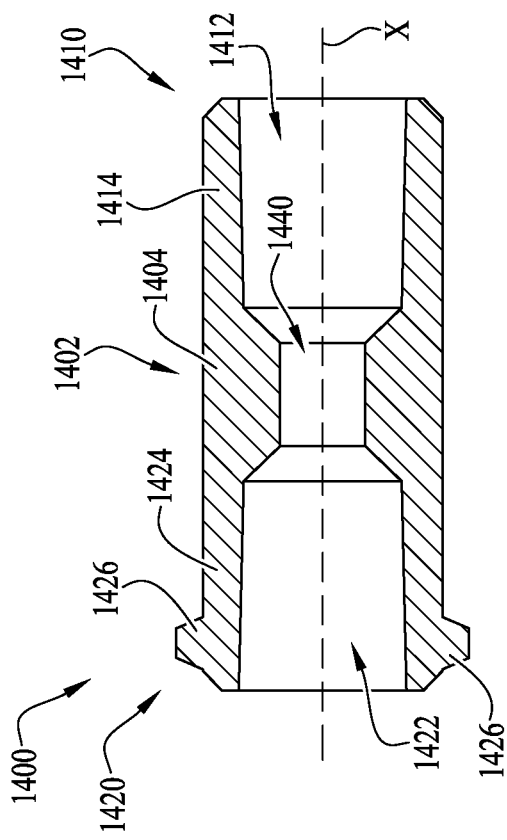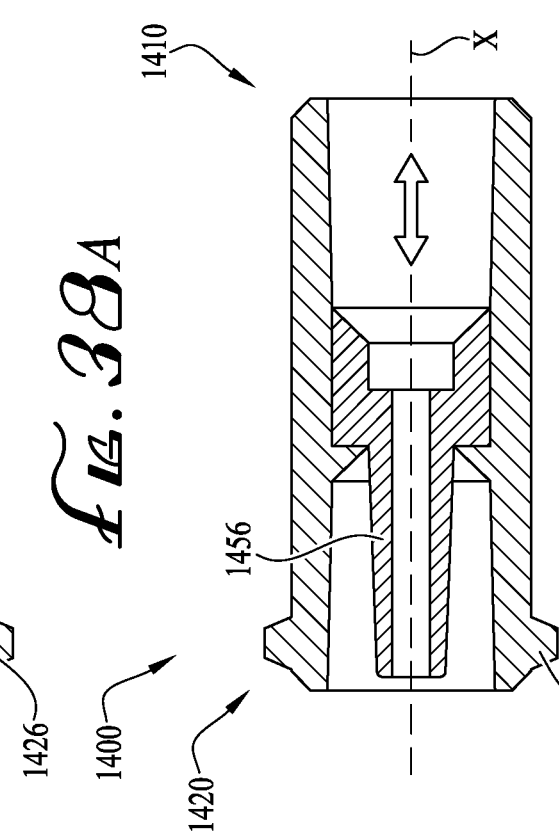
Fig. 38A
Fig. 38B
Fig. 38C
Fig. 38D

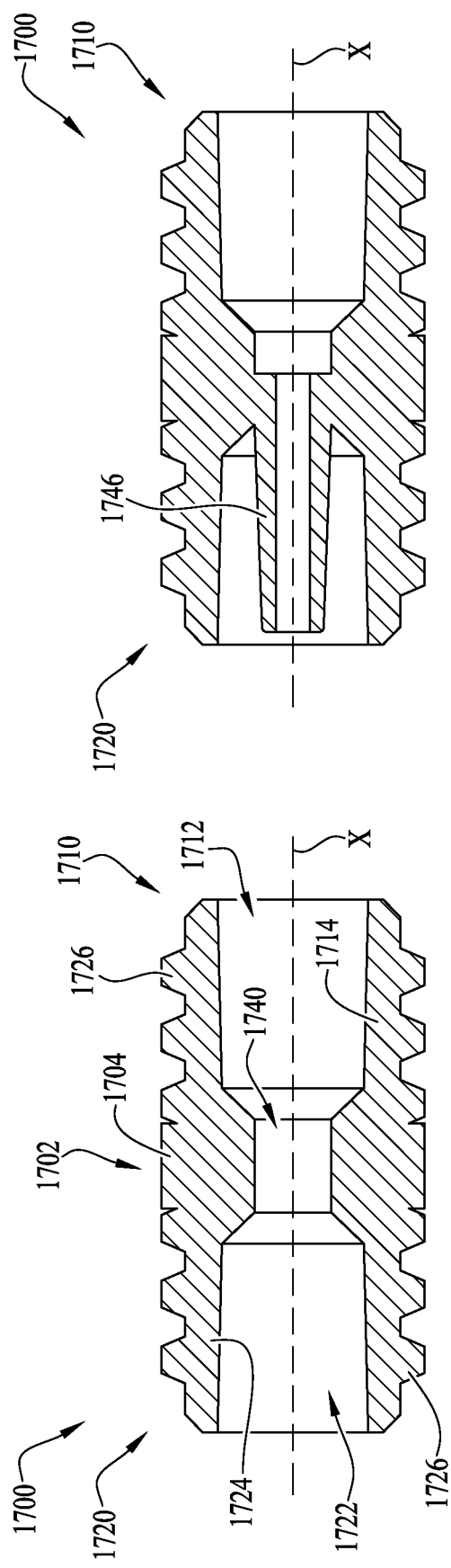
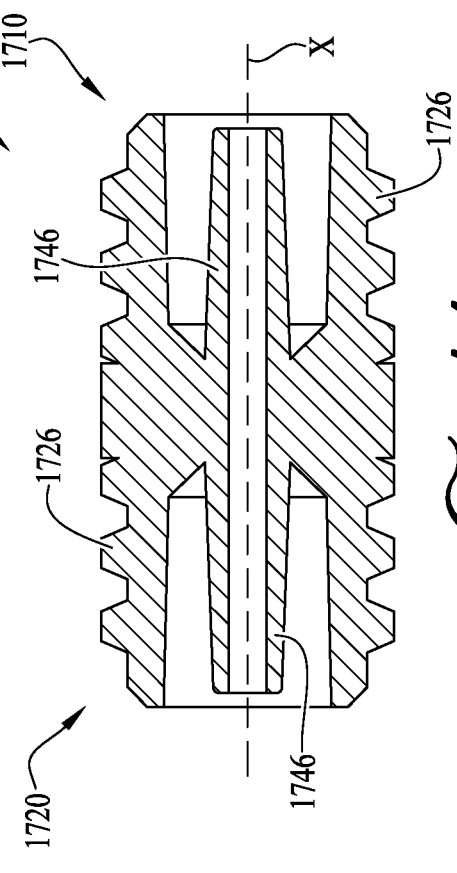
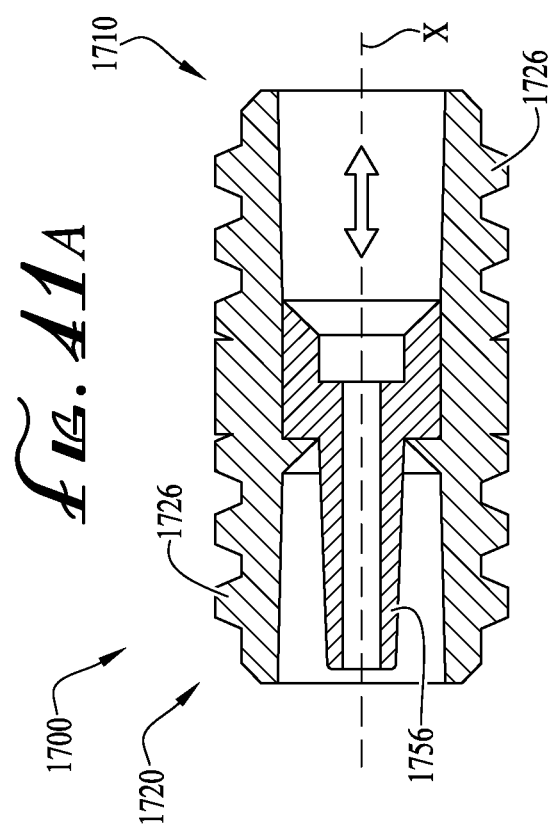
Fig. 41A  Fig. 41B  Fig. 41C  Fig. 41D

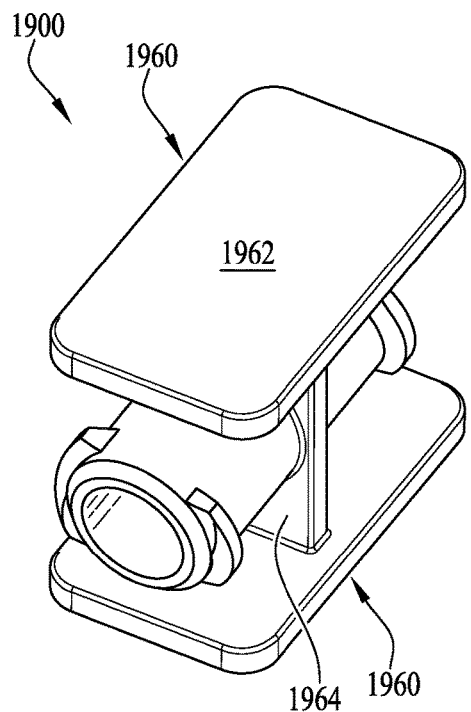
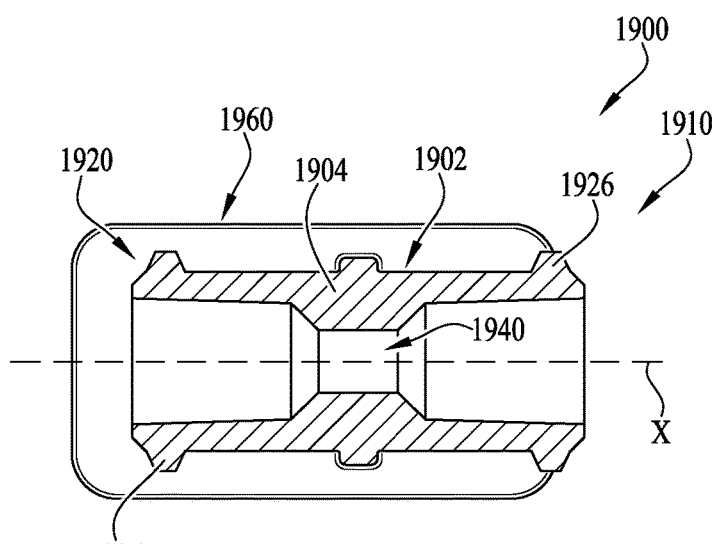
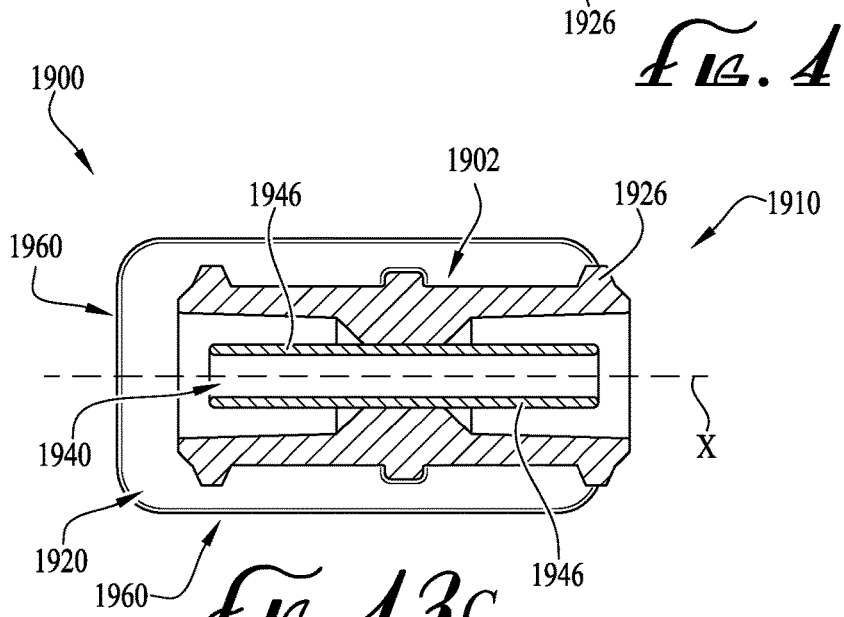

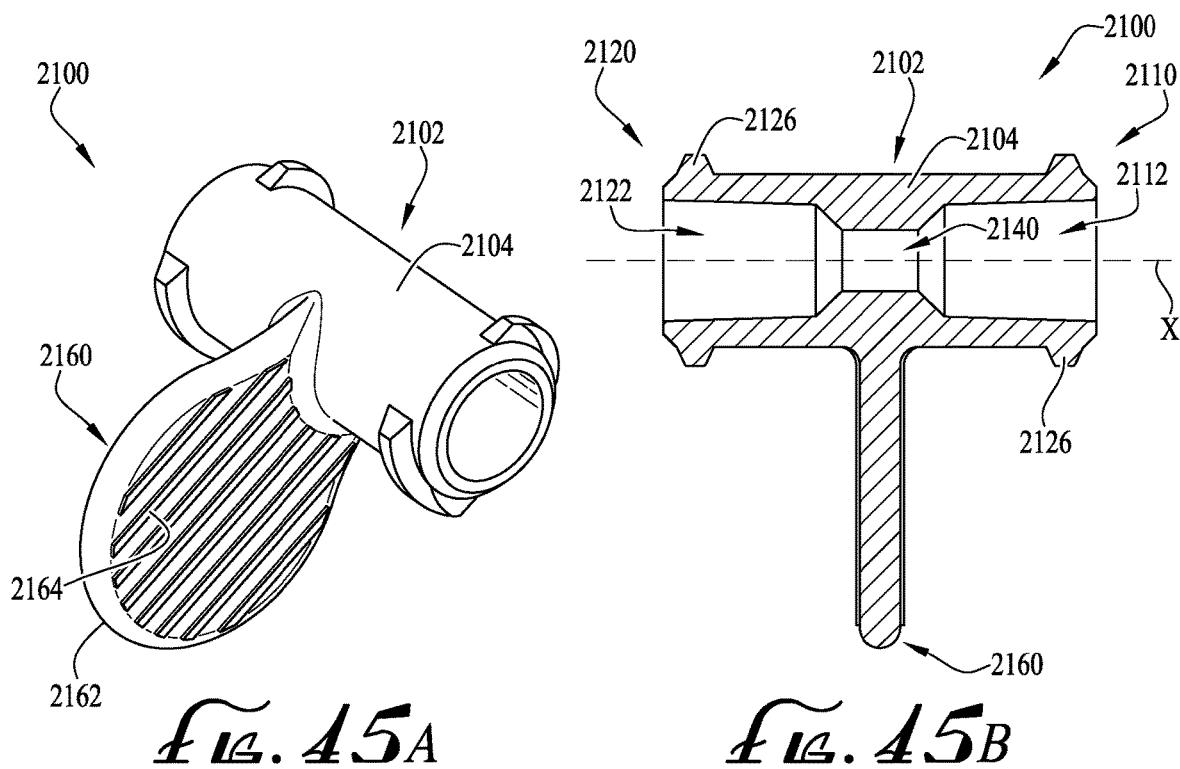
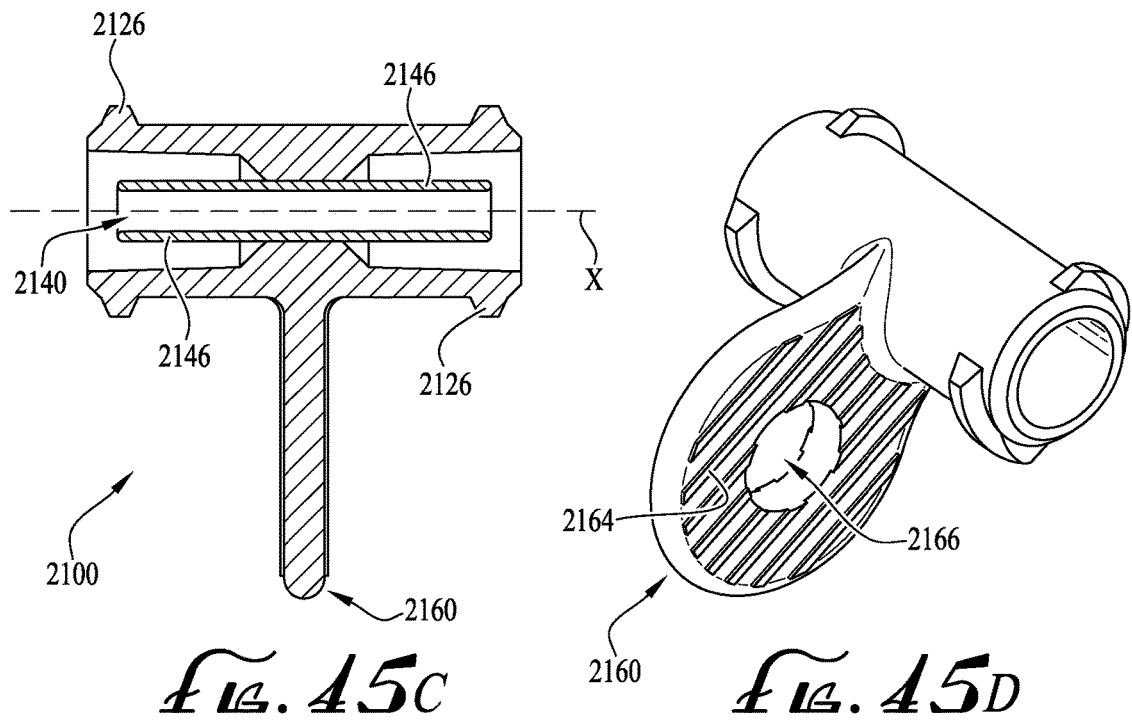

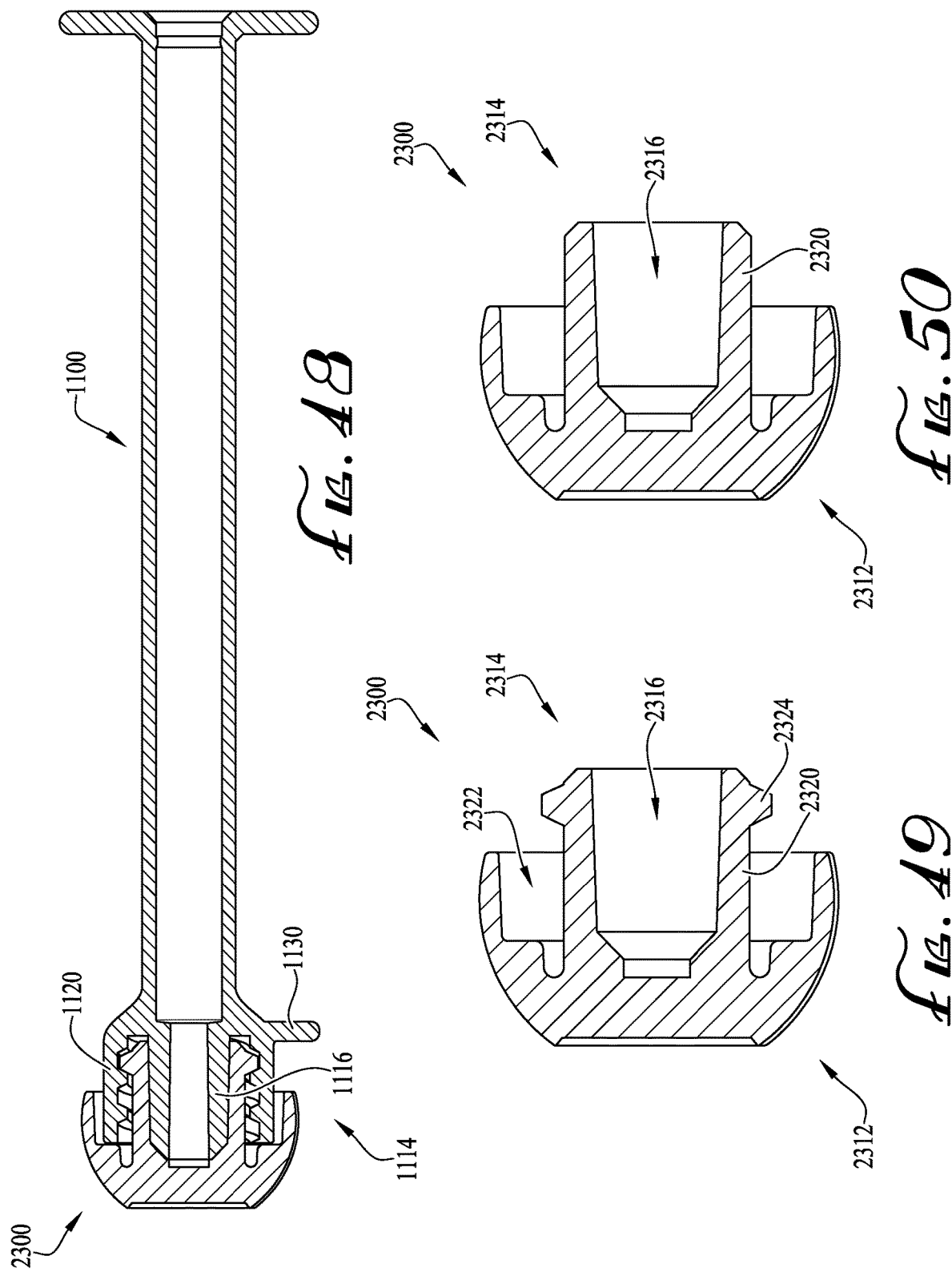

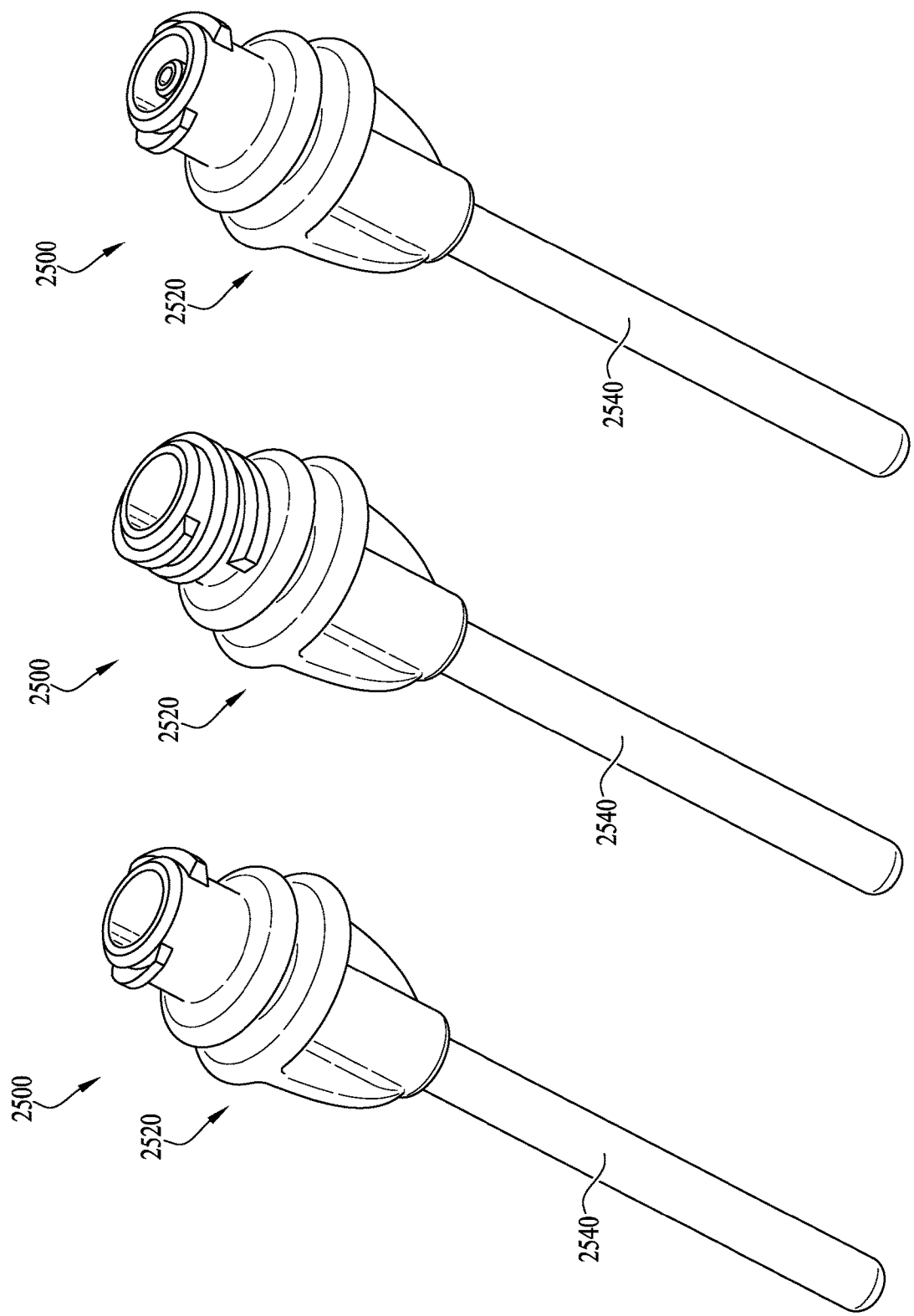

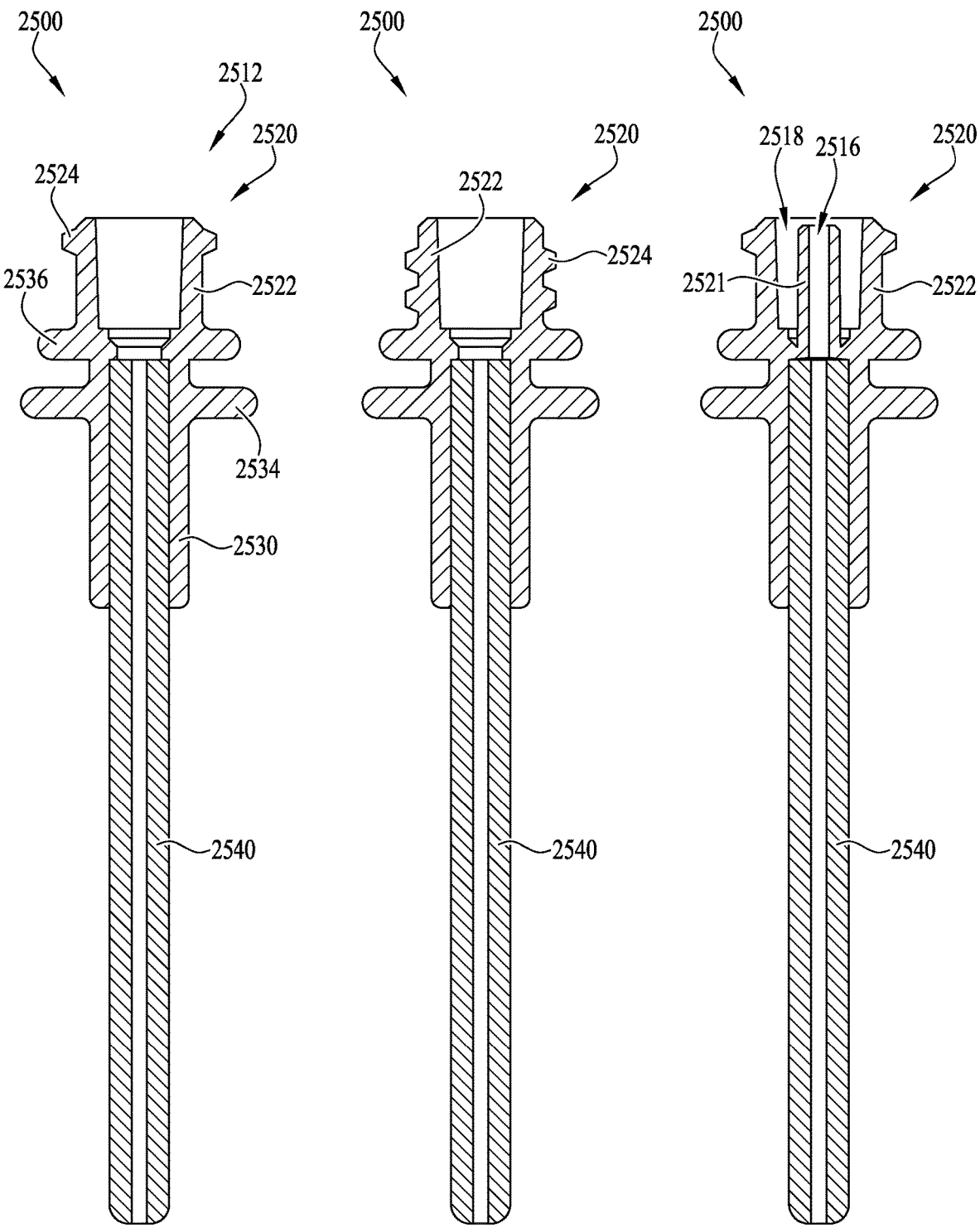

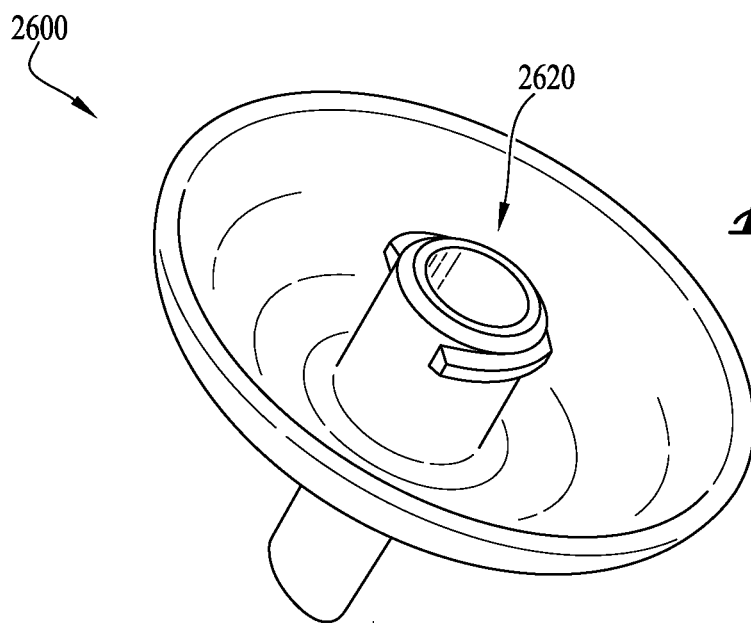
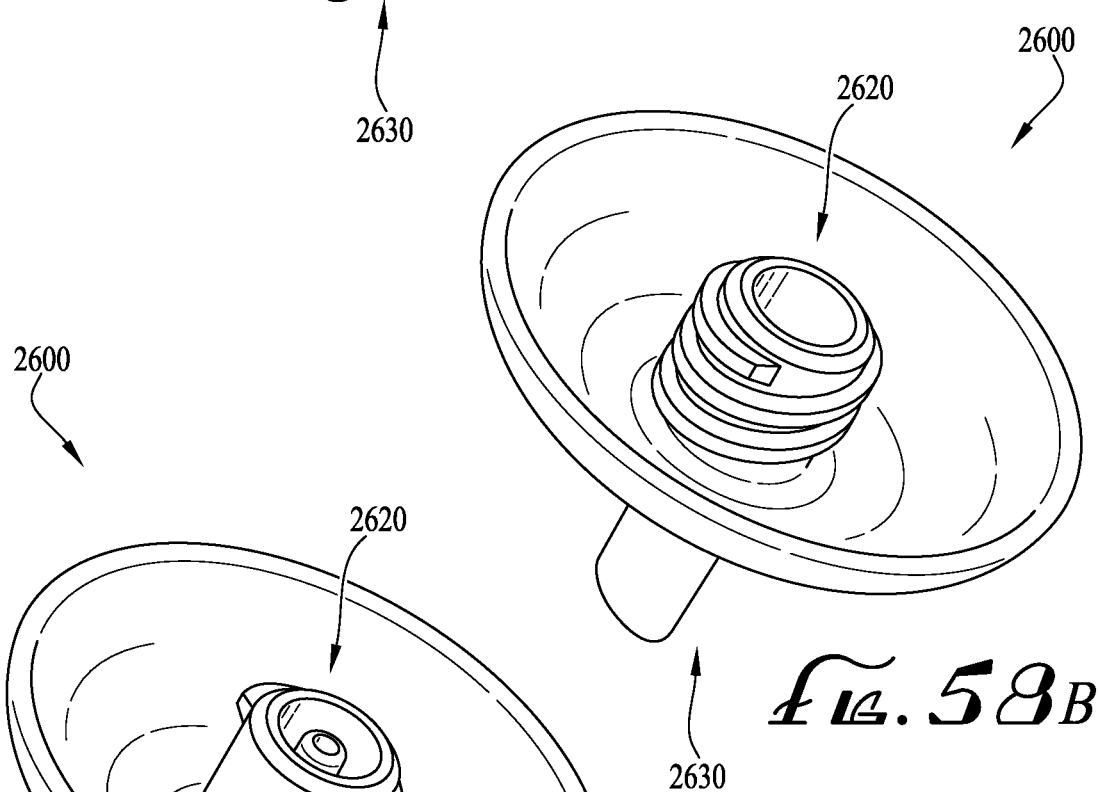
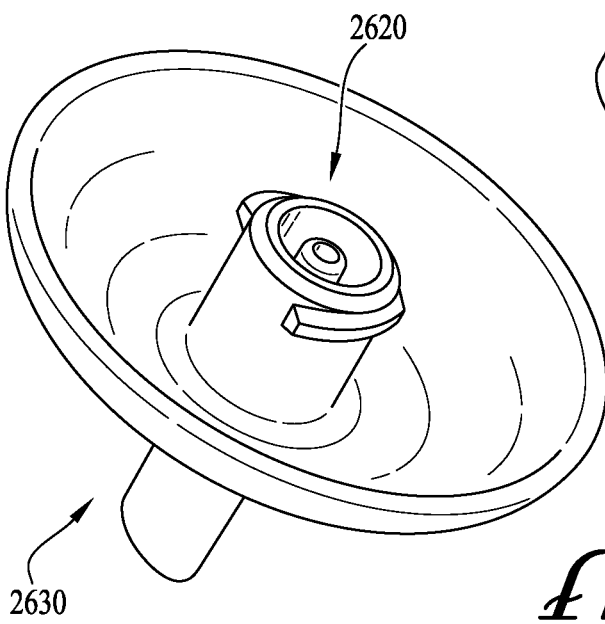

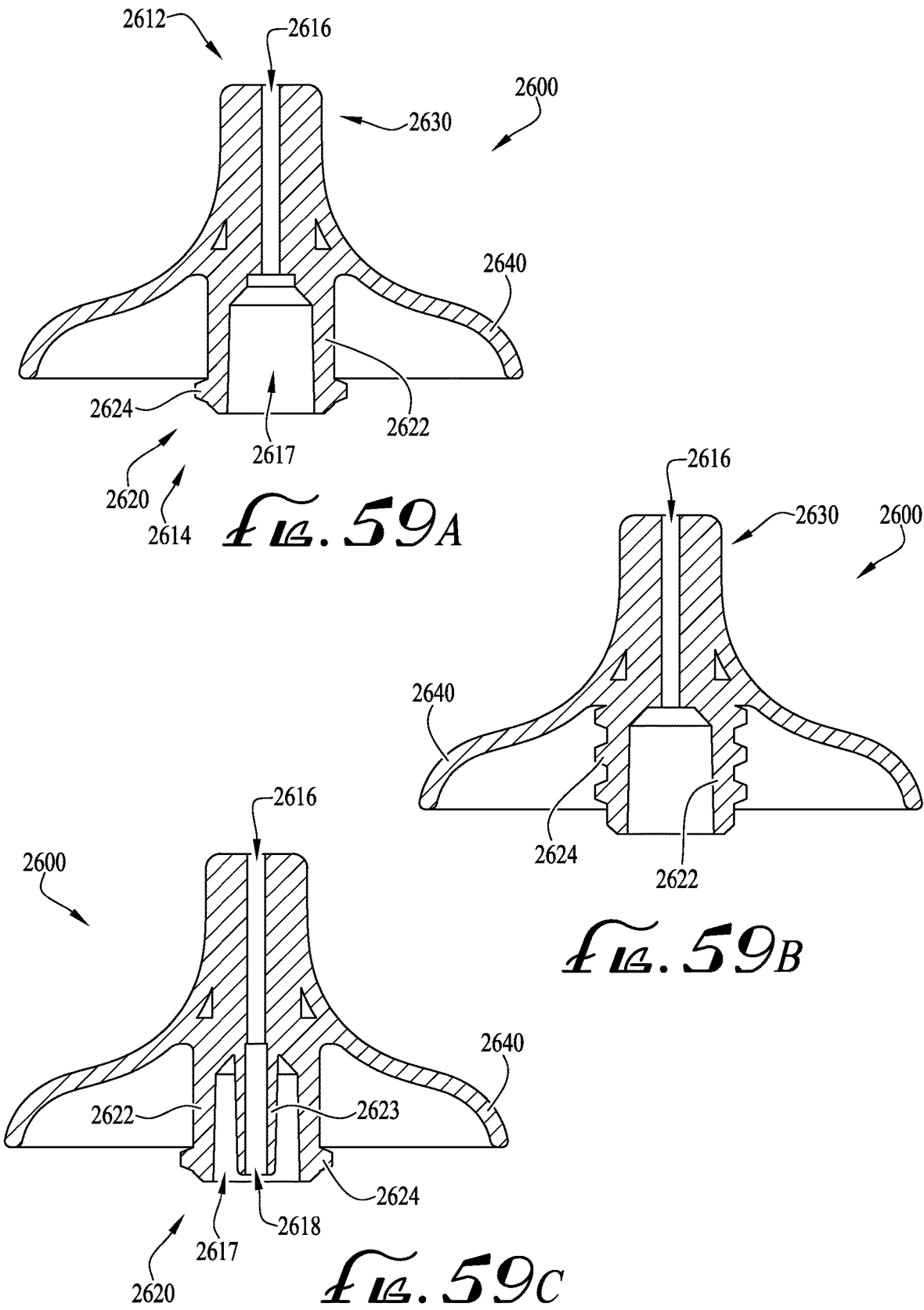

DOSING CONTROL COUPLING FOR ENTERAL FLUID TRANSFER AND ENTERAL COUPLINGS AND SYRINGES

CROSS-REFERENCE TO RELATED APPLICATIONS

This application claims the priority benefit of U.S. Provisional Patent Application Ser. No. 62/376,006 filed Aug. 17, 2016 and U.S. Provisional Patent Application Ser. No. 62/366,399 filed Jul. 25, 2016, and is a continuation-in-part of U.S. Non-Provisional patent application Ser. No. 15/210,282 filed Jul. 14, 2016, which claims the priority benefit of U.S. Provisional Patent Application Ser. No. 62/192,454 filed Jul. 14, 2015, U.S. Provisional Patent Application Ser. No. 62/207,120 filed Aug. 19, 2015 and U.S. Provisional Patent Application Ser. No. 62/350,934 filed Jun. 16, 2016, all of which are hereby incorporated herein by reference in their entireties.

TECHNICAL FIELD

The present invention relates generally to the field of enteral feeding and fluid transfer devices.

BACKGROUND

Healthcare patients and neonates are commonly administered fluids such as medication and nutrients through the use of enteral fluid delivery syringes and other enteral fluid transfer and delivery devices. Particularly in smaller volume quantities of enteral fluid delivery, accurate dosing measurement is often highly desirable. Commonly, variations in the size, configuration and positioning of cooperating coupling elements of enteral fluid delivery devices can result in dosing inaccuracies.

In particular, enteral syringes and other components having enteral-only couplings conforming to the ISO 80369-3 design standard (commonly known as ENFit®) may have larger dimensions and thus larger contained volume or displacement within the coupling than previous enteral syringe designs. Volumetric differences in fluid delivery resulting from these changes may adversely affect accuracy of dosing in oral and/or enteral administration of fluids.

Furthermore, enteral syringes and other components having couplings formatted differently than the ISO 80369-3 design standard are not connectable with ISO 80369-3 formatted syringes and components.

Thus it can be seen that needs exist for improved coupling configurations for enteral syringes and other components that enable more accurate control of fluid delivery dosing and connectability between enteral couplings formatted differently than the ISO 80369-3 standard and enteral coupling formatted according to the ISO 80369-3 standard. It is to the provision of an improved enteral and/or oral dosing control coupling and enteral syringes and other equipment incorporating such dosing control couplings that the present invention is primarily directed.

SUMMARY

In example embodiments, the present invention provides an enteral dosing control coupling and enteral syringes and other equipment incorporating such dosing control couplings that enables more accurate control of fluid delivery dosing.

In example forms, the enteral dosing control coupling incorporates a modified female ISO 80369-3 formatted coupling having a lumen extension tip for engagement within the lumen of a male ISO 80369-3 formatted coupling. The lumen extension tip reduces the volume of residual fluid contained in the coupling, and retains a substantially consistent volume of residual fluid contained in the coupling during fluid transfer into and out of the enteral syringe. For example, a substantially consistent residual volume is contained in the lumen extension tip when a syringe incorporating such a dosing control coupling is coupled to a larger volume container for filling, and when the syringe is coupled to a feeding tube for fluid delivery. Furthermore, the syringe incorporating the dosing control coupling can be coupled to other ENFit ISO 80369-3 formatted couplings and connectors.

In one aspect, the present invention relates to an enteral dosing control coupling including a cylindrical collar defining a hollow internal chamber and a lumen extension tip projecting axially into the internal chamber. An internal lumen extends axially through the lumen extension tip. In example embodiments, external coupling members are formed on a portion of the cylindrical collar.

In another aspect, the present invention relates to an enteral syringe including a hollow cylindrical barrel and a dosing control coupling. The hollow cylindrical barrel includes a cylindrical collar with an internal chamber and external coupling members. The dosing control coupling includes a lumen extension tip projecting axially into the internal chamber, and defining an internal lumen extending therethrough. In example embodiments, the cylindrical collar is generally shaped and sized according to the ISO 80369-3 standard. In one example form, the lumen extension tip is generally integrally formed with the cylindrical collar. In another example form, the lumen extension tip is a separate piece and configured to provide for removable coupling engagement with a portion of the enteral syringe.

In example forms, the lumen extension tip includes a generally elongate cylindrical body having a base portion for coupling engagement within the hollow cylindrical barrel of the enteral syringe. The base portion includes an outer peripheral surface for engagement with a surface defined by the hollow cylindrical barrel. In some example forms, the lumen extension tip comprises a sealing member for providing a seal between the hollow cylindrical barrel and the base portion of the lumen extension tip. In example forms, the outer peripheral surface of the base portion includes one or more engagement features for cooperating engagement with an engagement feature provided within the hollow cylindrical barrel.

In some example forms, a plunger is axially movable within the barrel to fill and dispense fluid into and from the syringe. The plunger optionally includes an elongate body having a forward end with a spear-like tip that is insertable within the internal lumen of the lumen extension tip of the syringe such that a contained volume within the internal lumen of the lumen extension tip is substantially zero. In this way, dosing inconsistencies and anomalies in accuracy during fluid delivery are substantially, if not entirely, eliminated.

In yet another aspect, the present invention relates to a lumen extension tip for use with an enteral syringe and for compatible fitting engagement within an internal conduit of a hub of a male ISO 80369-3 formatted coupling. The lumen extension tip includes an elongate cylindrical body, an internal conduit extending entirely through the cylindrical body, and a base portion including an outer peripheral surface and an abutment surface. The outer peripheral surface is configured for engagement with a hollow cylindrical barrel of the enteral syringe and the abutment surface is configured for seating engagement with an upper surface of a platform defined within the hollow cylindrical barrel. In example forms, a sealing member is provided and positioned between the abutment surface and the upper surface of the platform. In example embodiments, the outer peripheral surface of the base portion and an inner surface of the hollow cylindrical barrel can be shaped and sized to provide for removable engagement therebetween In yet another aspect, the present invention relates to an enteral syringe including a hollow cylindrical barrel and a dosing control coupling. The hollow cylindrical barrel is adapted to receive a plunger for retraction and advancement within the syringe barrel to transfer a delivered fluid to and from a contained volume of the syringe barrel. The dosing control coupling extends along an elongate axis from a first end to a second end. The first end includes a cylindrical outer collar defining a hollow internal chamber and a lumen extension tip projecting axially into the internal chamber of the collar. The second end includes an end coupling for engagement with the hollow syringe barrel.

In another aspect, the present invention relates to an enteral coupler including a coupling member having an elongate body extending a length along a longitudinal axis from a first end to a second end and defining a lumen extending therethrough. The first end includes a female formatted coupling and the second end includes a female formatted coupling. In example embodiments, at least one of the female formatted couplings includes a female ISO 80369-3 formatted coupling.

In another aspect, the present invention relates to an enteral connector for coupling engagement with a syringe including a male ISO 80369-3 formatted coupling. The connector includes a female ISO 80369-3 formatted coupling including a cylindrical outer collar defining a hollow internal chamber and a lumen extending entirely through the outer cylindrical collar.

These and other aspects, features and advantages of example embodiments of the invention will be understood with reference to the drawing figures and detailed description herein, and will be realized by means of the various elements and combinations particularly pointed out in the appended claims. It is to be understood that both the foregoing general description and the following brief description of the drawings and detailed description are exemplary and explanatory of embodiments of the invention, and are not restrictive of the invention, as claimed.

BRIEF DESCRIPTION OF THE DRAWINGS

FIG. 1 is a perspective view of an enteral syringe barrel including an enteral dosing control coupling according to an example embodiment of the present invention, shown connected to a male ISO 80369-3 formatted coupling.

FIG. 2 is a second perspective view of the enteral syringe of FIG. 1, disconnected from the male ISO 80369-3 formatted coupling, and showing the proximal end incorporating a lumen extension tip.

FIGS. 3A-B show cross-sectional views of an enteral dosing control coupling according to the present invention, connected to a male ISO 80369-3 formatted coupling, showing the small variation of residual volume contained in the lumen extension tip.

FIG. 6 shows the enteral syringe of FIG. 1, with a tip cap closure mounted on its proximal end.

FIG. 7 shows a cross-sectional view of the enteral syringe and mounted tip cap enclosure of FIG. 6 taken along line 7-7.

FIG. 8 is a perspective view of an enteral syringe including a hollow cylindrical barrel, an enteral dosing control coupling, and a plunger movably mounted within the barrel, according to another example embodiment of the present invention.

FIG. 9 is a perspective view of the plunger of FIG. 8, removed from the syringe barrel.

FIG. 10 is a cross sectional view of the enteral syringe of FIG. 8.

FIG. 11 is a detailed cross-sectional view of the enteral dosing control coupling portion of the syringe of FIG. 10.

FIG. 12 shows an enteral syringe including an enteral dosing control coupling in the form of a lumen extension tip according to another example embodiment of the present invention, and showing a section of the coupling removed to show internal portions thereof.

FIG. 13 shows a detailed view of the enteral syringe of FIG. 12, and showing the lumen extension tip of the enteral dosing control coupling in a seated and fully extended position.

FIG. 14 shows a detailed view of the enteral dosing control coupling of FIG. 12, and showing the lumen extension tip of the enteral dosing control coupling at least partially retracted within the syringe.

FIG. 15 shows a detailed view of the enteral dosing control coupling of FIG. 12, and showing the lumen extension tip of the enteral dosing control coupling entirely removed from the syringe.

FIG. 24 is a perspective view of a syringe having a dosing control coupling according to another example embodiment of the present invention.

FIG. 25 shows a cross-sectional view of the syringe of FIG. 24 taken along line 25-25.

FIG. 26 is a perspective view of a syringe having a dosing control coupling according to another example embodiment of the present invention.

FIG. 27 shows a cross-sectional view of the syringe of FIG. 24 taken along line 27-27.

FIGS. 29A-C show perspective and front views of an enteral syringe including a dosing control coupling according to another example embodiment of the present invention.

FIG. 30 shows a cross-sectional view of a syringe including a dosing control coupling according to another example embodiment of the present invention.

FIG. 31 shows a cross-sectional view of an enteral syringe including a dosing control coupling according to another example embodiment of the present invention.

FIG. 32 shows a cross-sectional view of an enteral syringe including an enteral dosing control coupling according to another example embodiment of the present invention.

FIG. 33 shows cross-sectional view of an enteral syringe according to another example embodiment of the present invention.

FIG. 34 shows the cross-sectional view of the enteral syringe of FIG. 33, and showing a tab extending from a portion of the syringe body.

FIG. 35 shows cross-sectional view of an enteral syringe according to another example embodiment of the present invention.

FIG. 36 shows the cross-sectional view of the enteral syringe of FIG. 35, and showing a tab extending from a portion of the syringe body.

FIGS. 38A-D show cross-sectional views of enteral couplers according to example embodiments of the present invention.

FIGS. 41A-D show cross-sectional views of enteral couplers according to example embodiments of the present invention.

FIG. 43A shows a perspective view of an enteral coupler according to another example embodiment of the present invention.

FIG. 43B shows a cross-sectional view of the enteral coupler of FIG. 43A.

FIG. 43C shows the cross-sectional view of the enteral coupler of FIG. 43B, and further including an enteral dosing control coupling.

FIG. 45A shows a perspective view of an enteral coupler according to another example embodiment of the present invention.

FIG. 45B shows a cross-sectional view of the enteral coupler of FIG. 45A.

FIG. 45C shows the cross-sectional view of the enteral coupler of FIG. 45B, and further including an enteral dosing control coupling.

FIG. 45D shows a perspective view of the enteral coupler of FIG. 45A, and showing a hole formed in a tab member thereof.

FIG. 48 shows a cross-sectional view of the enteral syringe of FIG. 34 coupled with a tip cap according to another example embodiment of the present invention.

FIG. 49 shows the cross-sectional view of the tip cap of FIG. 48.

FIGS. 50-51 show cross-sectional views of a tip cap according to example embodiments of the present invention.

FIGS. 56A-C show perspective view of oral administration couplers according to example embodiments of the present invention.

FIGS. 57A-C show cross-sectional views of the oral administration couplers of FIGS. 56A-C.

FIGS. 58A-C show perspective views of an oral administration couplers according to example embodiments of the present invention.

FIGS. 59A-C show cross-sectional views of the oral administration couplers of FIGS. 58A-C.

DETAILED DESCRIPTION OF EXAMPLE EMBODIMENTS

Figure 4:
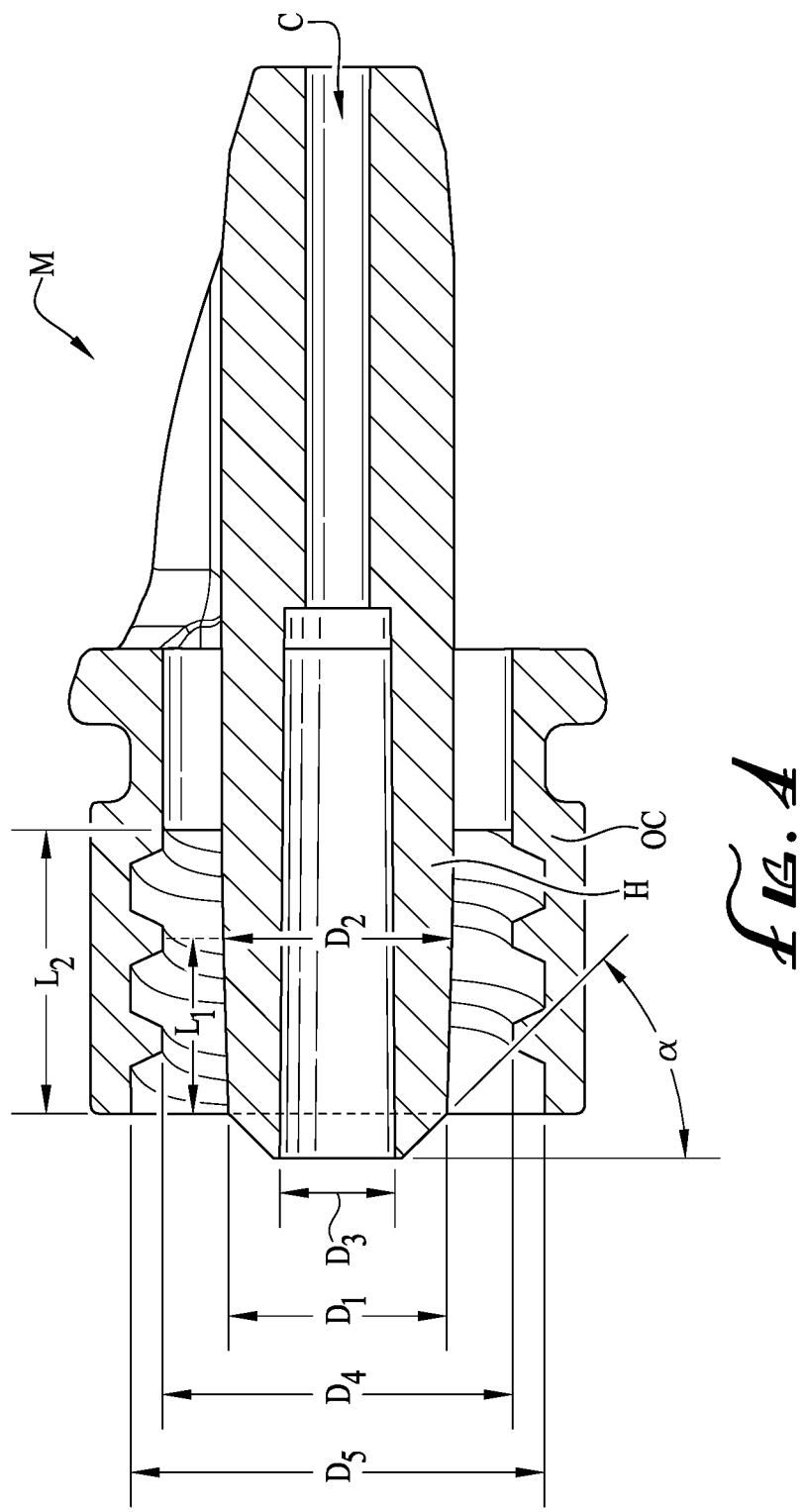
FIG. 4 shows a cross-sectional view of the male ISO 80369-3 formatted coupling of FIGS. 3A-B.

The present invention may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-7 show an enteral syringe 10 comprising an enteral dosing control coupling or low-dose tip according to an example embodiment of the invention. In example embodiments, the enteral syringe 10 includes a hollow cylindrical barrel 20, a base flange 30 at a distal end of the barrel, and an enteral dosing control coupling 40 at a proximal end of the barrel. As would be understood by one of ordinary skill in the art, the barrel 20 is adapted to receive a syringe plunger (see FIG. 8, as will be described below), which is axially advanced and retracted within the barrel to fill and dispense fluid into and from the syringe in typical fashion. A positioning flange 22 optionally extends transversely outward from the barrel 20, proximal the coupling 40. In some example embodiments, the syringe can be provided for use with a syringe pump, for example, where one or more portions of the syringe and/or the plunger can be interengageable with one or more portions of the syringe pump for moving the plunger relative to the syringe to dispense fluids from the syringe.

In the depicted example embodiment, the coupling 40 generally comprises a modified female ISO 80369-3 formatted coupling substantially conforming to ISO design standard 80369-3, and is engageable with a compatible coupling element such as a corresponding male ISO 80369-3 formatted coupling M, as shown in FIG. 1. In example applications, the male ISO 80369-3 formatted coupling M can be part of a feeding or extension tube, a pharmacy cap, or other enteral fluid delivery equipment to which the syringe 10 is to be coupled. As used herein, it is to be understood that the terms "ISO 80369-3 formatted" or "ISO 80369-3 format" are intended to be broadly construed to include ISO 80369-3 compatible, ISO 80369-3 compliant, or both ISO 80369-3 compatible and ISO 80369-3 compliant according to the ISO 80369-3 design standard.

Figure 5:
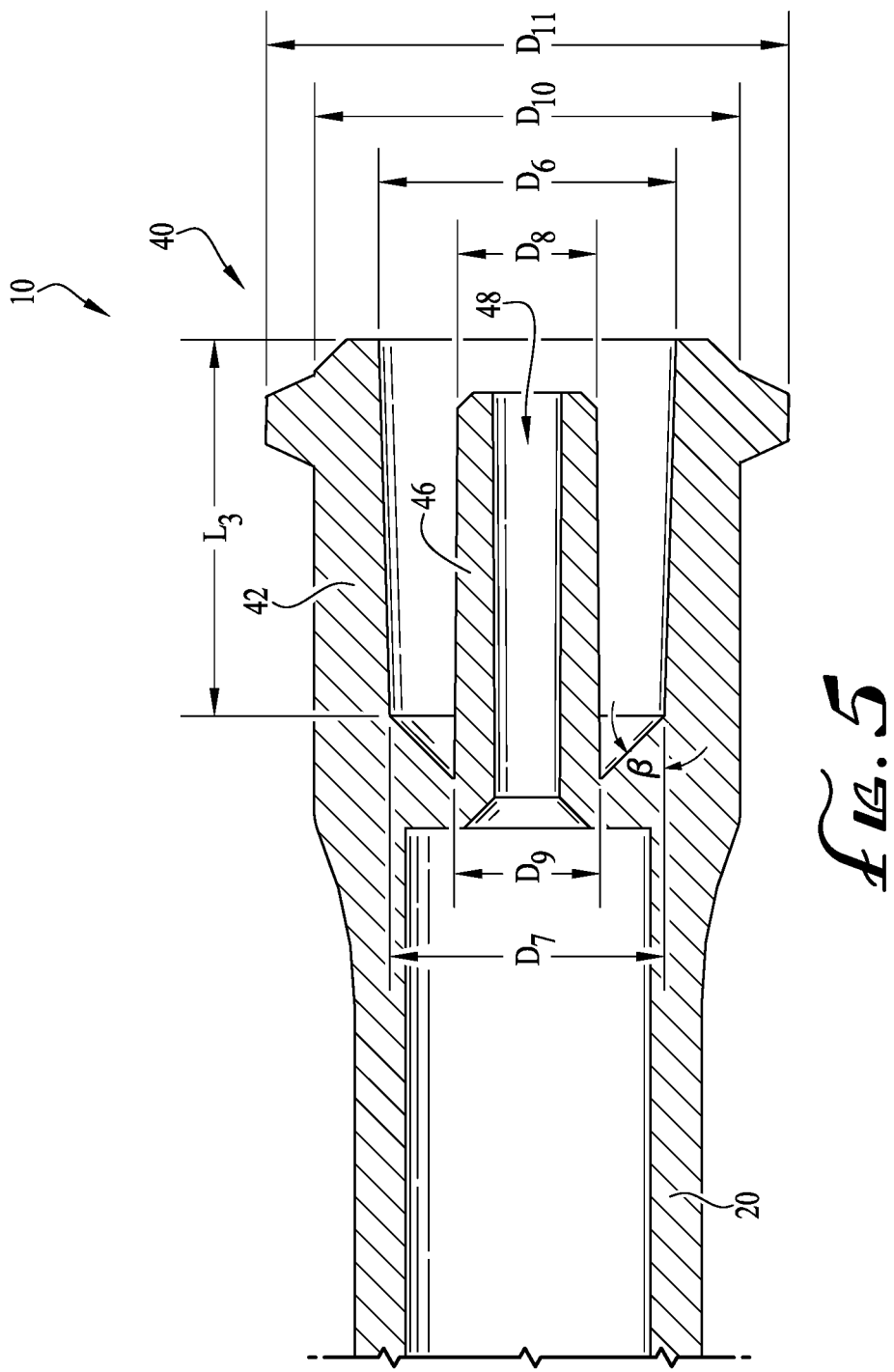
FIG. 5 shows a cross-sectional view of the female ISO 80369-3 formatted coupling portion of the enteral syringe of FIGS. 3A-B.

As depicted in FIGS. 2 and 5, the coupling 40 comprises a cylindrical outer collar 42 defining a hollow internal chamber, and a pair of helical coupling lugs 44 projecting outwardly from the exterior surface of the collar. Optionally, rather than lugs 44 projecting from the exterior surface of the collar, the exterior surface of the collar 42 can comprise helical threads generally extending about at least a portion of the exterior surface thereof, for example, like threads on a bolt, other types of conventional coupling members, etc. In some example embodiments, the exterior surface of the collar is entirely smooth without any lugs, for example, whereby a frictional fit (as will be described below) will be provided between the male ISO 80369-3 formatted coupling M and the coupling 40.

The coupling 40 further comprises a lumen extension tip 46, projecting axially from the barrel 20 of the syringe into the internal chamber of the collar 42. An internal lumen or enteral fluid delivery conduit 48 extends through the lumen extension tip 46 for fluid communication to and from the contained volume of the barrel 20, allowing fluid delivery in and out of the barrel. As shown in cross-section by FIGS. 3A-B, when the coupling 40 is engaged with a male ISO 80369-3 formatted coupling M, the lumen extension tip 46 is received within the lumen of a male coupling hub H (in effect becoming a male coupling element within the "female" lumen of the male ISO 80369-3 formatted coupling). The lumen extension tip 46 is generally cylindrical or tubular and includes an internal surface defining the lumen or fluid delivery conduit 48, a cylindrical or slightly tapered external surface, and a distal tip at its free end. The outer coupling collar 42 is also generally cylindrical or tubular, and at least partially surrounding the lumen extension tip 46. The collar 42 comprises an internal surface confronting and spaced a distance apart from the external surface of the lumen extension tip, and further comprises an external surface optionally comprising the lugs 44 or other coupling or connection features, and an outer rim at its distal free end. The internal dimension of the collar 42 is greater than the external dimension of the lumen extension tip 46, such that a space therebetween forms a receiver for a cooperating portion of a compatible coupling element. The lumen extension tip 46 is positioned generally concentrically and coaxially within the collar 42, and the lumen 48 extends generally centrally through the lumen extension tip also concentric and coaxial with the collar.

According to example embodiments, the lumen extension tip 46 is integrally formed with the coupling 40 whereby an internal end surface of the barrel 20 provides support for the extension of the tip 46 within the internal chamber of the collar 42. Typically, the lumen extension tip 46 is generally sized and shaped for substantially fitting within the lumen of the male coupling hub H of the male ISO 80369-3 formatted coupling M (see FIGS. 3A-B). In example embodiments, the coupling 40 (comprising the lumen extension tip 46) is preferably engagable with ISO 80369-3 formatted connectors (e.g., compliant or compatible). In some example embodiments, the extension of the tip 46 does not extend beyond an end of the collar 42, for example, such that the tip is recessed between about 0.45-0.65 millimeters below the end of the collar 42, for example about 0.55 millimeters according to example embodiments. However, according to other example embodiments, the tip 46 extends beyond the end of the collar 42. In example embodiments, the size, shape and extension of the tip 46 is generally configured for compatible engagement within the lumen of the male coupling hub H.

In example embodiments, the lumen extension tip 46 is configured such that dosing inconsistencies and anomalies in accuracy during fluid delivery are reduced, minimized or substantially eliminated. With respect to the coupling configuration shown in FIGS. 3A-B, it can be seen that the lumen extension tip 46 retains a substantially consistent volume of residual fluid contained in the internal lumen 48 of the extension tip during fluid transfer into and out of the enteral syringe. In example embodiments, the contained volume CV of the lumen extension tip 46 is between about 0.005 milliliters to about 0.03 milliliters, and more preferably about 0.01 milliliters (see FIG. 3B). In example embodiments the combined tip volume CTV (e.g., lumen plus the rest of the fluid space in the tip) is preferably about 0.017 milliliters (see FIG. 3A).

As depicted in FIG. 4 and as described above, the male coupling M is preferably formatted according to the ISO 80369-3 standard. For example, the male coupling hub H comprises a first outer diameter D1 that is defined at an end of the hub H adjacent the beginning of a tapered end surface (defined by angle α), a second outer diameter D2 that is defined at a length L1 from the end of the hub H adjacent the taper. The internal lumen of the hub H is defined by a diameter D3. An outer collar OC generally surrounds the hub H for providing coupling engagement with the lugs 44 of the coupling 40 of the syringe 10. The outer collar comprises a minor inside thread diameter D4 and a major inside thread diameter D5. The length of the hub H from the end of the outer collar OC is defined by a length L2. In typical configurations, the first outer diameter D1 is about 5.41 millimeters, the second outer diameter D2 is about 5.64 millimeters, the internal lumen diameter D3 is about 2.90 millimeters, the minor inside thread diameter D4 is about 8.65 millimeters, the major inside thread diameter D5 is about 10.23 millimeters, and the angle α is about 45 degrees. In some configurations, the diameter D5 is larger than 10.23 millimeters, for example, wherein the male hub H generally relies on frictional engagement with the coupling 40 (e.g., instead of the lugs 44 engaging the threads of the outer collar OC). Alternatively, the collar 42 can be substantially smooth without lugs such that the outer collar 42 can generally pass between the first and second diameters D1, D2 of the hub H and the minor inside thread diameter D4, for example, where a frictional fit is provided between the hub H and an interior or inner wall of the collar 42. The length L1 is about 3.82 millimeters and the length L2 is about 6.82 millimeters or greater.

In example embodiments, the coupling 40 (and enteral dosing control coupling thereof) is formatted according to the ISO 80369-3 standard, for example, to provide for coupling engagement with the male coupling M (and the hub H thereof). For example, as depicted in FIG. 5, the coupling 40 comprises a first internal diameter D6 and a second internal diameter D7 that are spaced a length L3 between each other. The lumen extension tip 46 comprises a first outer diameter D8 defined near its end and a second outer diameter D9 defined at the connected side of the tip 46. An angled taper (defined by an angle β) is provided between the base end of the tip 46 and an internal surface of the collar 42. The lugs 44 of the collar 42 define a minor outside thread diameter D10 and a major outside thread diameter D11. According to example embodiments, the first internal diameter D6 is about 5.69 millimeters, the second internal diameter D7 is about 5.26 millimeters, the first outer diameter D8 of the tip 46 is about 2.50 millimeters, the second outer diameter D9 of the tip 46 is about 2.85 millimeters, the minor outside thread diameter D10 is about 8.10 millimeters, and the major outside thread diameter D11 is about 9.93 millimeters. The length L3 defined between the first and second internal diameters D6, D7 is about 7.14 millimeters, and the angle β of the angled taper is about 45 degrees. Optionally, according to alternate example embodiments, the male coupling M and the coupling 40 can be sized as desired.

In example embodiments, the first and second outer diameters D8, D9 of the lumen extension tip 46 are generally sized and shaped to provide for compatible fitting engagement within the internal lumen of the hub H of the male coupling M (defined by internal diameter D3). Thus, with the internal lumen diameter D3 being about 2.90 millimeters, the first and second outer diameters D8, D9 are preferably sized to provide for fitting engagement within the internal lumen thereof. In some example embodiments, the first and second diameters D8, D9 are configured such that little to no interference is provided between the tip 46 and the internal lumen of the hub H. Alternatively, the first and second diameters D8, D9 can be configured such that at least some interference is provided therebetween to frictionally and/or sealingly engage the two together.

In example embodiments, the lumen extension tip 46 preferably assists in the prevention of unwanted fluid transfer when uncoupling the coupling hub H from the syringe 10. Typically, a vacuum is formed when the coupling hub H and the syringe 10 are coupled together and fluid is communicating therebetween (or stagnant therein). Thus, by providing the lumen extension tip 46, a smaller quantity of fluid is present and subject to being transferred back into the syringe 10. Accordingly, provision of the lumen extension tip 46 preferably minimizes the unwanted transfer of fluid, which is intended to be carried within and out of the coupling hub H, from being drawn back into the syringe 10 when the connection between the coupling hub H and the lumen extension tip 46 is broken.

While the coupling 40 comprising the lumen extension tip 46 is described and shown herein as part of an enteral syringe, it will be understood that the lumen extension tip of the present invention may be incorporated in the coupling elements of various other types of enteral fluid collection, storage and/or transfer devices as well. Thus, the present invention includes without limitation, a coupling (such as for example, a modified female ISO 80369-3 formatted coupling) including a lumen extension tip as disclosed, as well as enteral fluid collection, storage and/or transfer devices comprising such a coupling, for example, syringes of differing sizes and formats, enteral fluid collection devices, enteral fluid storage devices, enteral fluid delivery or transfer tubes or conduits, enteral connectors or couplings, and the like, as well as accessories, couplings and adaptors for use in connection with various ISO 80369-3 formatted or non-ENFit enteral fluid storage and delivery devices.

For example, according to one example embodiment as depicted in FIGS. 6-7, a tip cap TC can be coupled to the coupling 40 for sealing the internal lumen 48 to prevent fluids from dispensing from the internal lumen, and for preventing debris and contaminants from contacting the coupling 40 and internal lumen 48. According to one example embodiment, the tip cap TC comprises a male hub H (as described above) for providing interengagement with the coupling 40 (and for permitting extension of the lumen extension tip 46 within the internal cavity of the male hub H). According to one example embodiment, the tip cap TC comprises a coaxial connection collar that is modified to comprise a radial array of two or more split retainer tab members or clips COC, which are generally at least partially flexible and resilient for outwardly flexing during engagement with the lugs 44 of the coupling 40. U.S. patent application Ser. No. 15/078,674, U.S. patent application Ser. No. 15/185,583, U.S. patent application Ser. No. 14/844,922, U.S. Design patent application Ser. No. 29/521,665, and U.S. Design patent application Ser. No. 29/533,173 are incorporated herein by reference and disclose various clipped, snap-on and dual-action attachment and removal mechanisms. Optionally, one or more of the ends of the couplings can be provided with tabs or clips for providing permanent engagement between the coupling and the compatible connector, for example, when it is intended to prevent removal of the coupling 40 (and syringe 10 thereof) from the compatible connector after use.

In an example method of use, a syringe 10 is connected to another enteral fluid delivery component by engagement of the modified female ISO 80369-3 formatted coupling 40 of the syringe with a male ISO 80369-3 formatted coupling, in typical fashion. The lumen extension tip of the syringe coupling is received within the lumen of the male ISO 80369-3 formatted coupling. Fluid is transferred in or out of the syringe, from or to the other enteral fluid delivery component by retracting or advancing the syringe plunger. A reduced and substantially consistent residual volume is contained in the lumen extension tip during sequential fluid transfer operations, thereby maintaining accurate dosing control.

According to an example embodiment of the present invention, the plunger of the syringe is preferably configured such that an end thereof extends within the internal lumen 48 of the lumen extension tip 46 as the plunger is advanced into the syringe body for fluid delivery, for example, to eliminate the dead space within the internal lumen 48 of the lumen extension tip 46 so that dosing inconsistencies and anomalies in accuracy during fluid delivery are further reduced, minimized or substantially eliminated. As shown in FIGS. 8-9, for example, an enteral syringe 100 is shown and comprises a plunger 150 movably mounted within a hollow cylindrical barrel 120, a base flange 130 at a distal end of the barrel, and an enteral dosing control coupling 140 at a proximal end of the barrel. As described above, the coupling 140 similarly comprises a cylindrical outer collar 142 and a pair of helical lugs 144 projecting outwardly from the exterior surface of the collar 142. In example embodiments, the plunger 150 comprises a generally elongate body 152 comprising a forward end portion 154 having a displacement member or generally spear-like tip or rod 156 at a forward end thereof. In the depicted embodiment, the forward end 154 includes a forward body portion 160, and a seal ring or gasket 162 positioned generally adjacent the forward end portion (see FIG. 9). Optionally, the rearward end of the plunger 150 can comprise an actuating flange or feature 164 for providing manipulation thereof to push or pull the plunger 150 into and out of the hollow cylindrical barrel 120.

FIGS. 10-11 show a cross-sectional view of the syringe 100 with the plunger 150 fully inserted within the hollow cylindrical barrel 120 and the tip 156 fully inserted within the internal lumen 148 of the lumen extension tip 146 of the modified ISO 80369-3 formatted coupling 140. Preferably, with the plunger 150 fully inserted therein, the contained volume within the internal lumen 148 of the lumen extension tip 146 is substantially zero, and thus, dosing inconsistencies and anomalies in accuracy during fluid delivery are substantially, if not entirely, eliminated. Typically, the size of the tip 156 is substantially similar to the size and shape of the internal lumen 148, and the size and shape of the elongate body 152 and forward end body portion 160 are substantially similar or slightly smaller than the size and shape of the hollow cylindrical barrel 120. According to example embodiments, the size of the gasket 162 is generally slightly greater than the size of the hollow cylindrical barrel 120.

FIGS. 12-17 show an enteral syringe 200 comprising an enteral dosing control coupling 240 according to another example embodiment of the invention. As similarly recited above, the enteral syringe 200 includes a hollow cylindrical barrel 220, a base flange 230 at a distal end of the barrel, and the enteral dosing control coupling 240 at a proximal end of the barrel. The barrel 220 is adapted to receive a syringe plunger, which is axially advanced and retracted within the barrel to fill and dispense fluid into and from the syringe in typical fashion. In example embodiments, a lumen extension tip 246 is generally floating or movable with respect to the syringe (e.g., a separate piece), and is generally fitted and interengageable within the barrel of the syringe such that at least a portion thereof extends from the coupling 240 (as similarly described above). According to example embodiments, configuring the lumen extension tip as a separate piece further de-risks the chances of a misconnection with a non-ENFit connector, and a substantially wide variety of options are available regarding the manufacturing and assembly of the tip and the syringe.

The lumen extension tip 246 comprises an internal lumen 248, and functions substantially similarly to the embodiments as described above, for example, such that dosing control inaccuracies are substantially eliminated to provide for accurate dosing control. As depicted in FIGS. 12-15, a portion of the coupling 240 is removed to show internal portions thereof. However, according to some example embodiments, the coupling 240 can comprise one or more cut-outs or removed sections (e.g., as depicted) to facilitate the removal and evacuation of any fluids that are contained within the coupling 240, for example, within the area defined between the lumen extension tip 246 and an interior wall portion of the coupling 240. In some example embodiments, about one cut-out portion is formed within the coupling 240. In other example embodiments, two or more cutouts are formed within the coupling 240. According to some example embodiments, one or more openings can be formed along any portion of the coupling 240, for example, to act as a drain or exit conduit for facilitating the removal of unwanted fluids.

Figure 17:
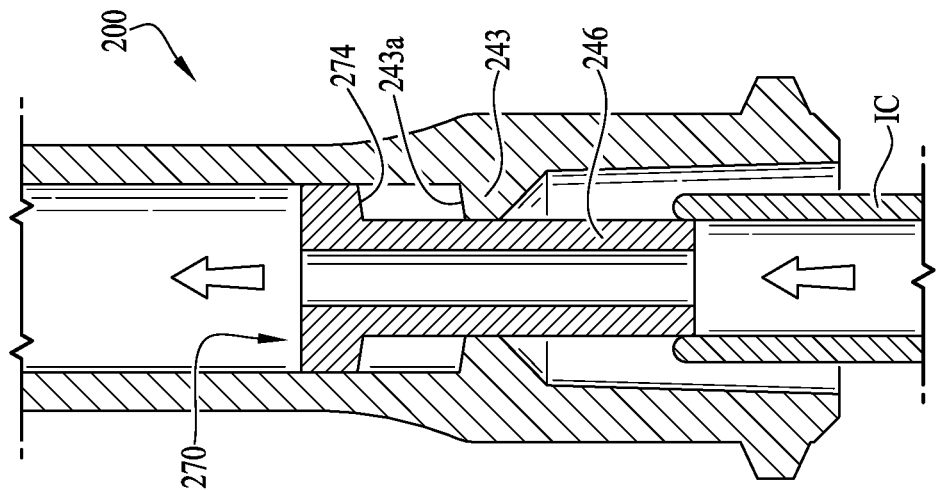
FIG. 17 shows the lumen extension tip of FIG. 12 retracted within the syringe by misconnecting a non-ENFit enteral connector with the lumen extension tip.
Figure 16:
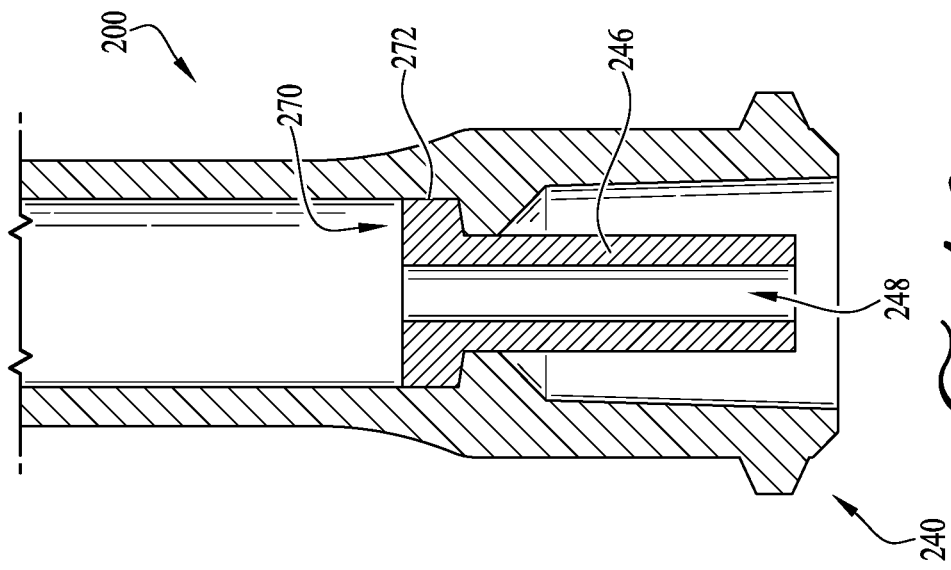
FIG. 16 shows a cross-sectional view of the enteral syringe of FIG. 12.

As depicted in FIGS. 13 and 16, the lumen extension tip 246 is preferably configured for fitting within at least a portion of the barrel 220, for example, such that at least a portion of the tip 246 extends coaxially within at least a portion of coupling 240, or within at least a portion of the space defined and surrounded by the collar of the modified female ISO 80369-3 formatted coupling substantially conforming to ISO design standard 80369-3, and is engageable with a corresponding male ISO 80369-3 formatted coupling M, as shown in FIG. 1. As depicted in FIG. 15, the lumen extension tip 246 generally comprises a cylindrical body defining the conduit 248 extending therethrough. In example embodiments, an end of the cylindrical body comprises a base portion 270 having an outer peripheral surface 272 for being retained within the internal conduit of the barrel. Furthermore, a contact or abutment surface 274 is provided for engaging a portion of the internal conduit within the barrel 220 (e.g., to define an in-use, fully-extended position). For example, as shown in FIGS. 15 and 17, an end of the internal conduit within the barrel 220 comprises an outer shelf or inwardly directed platform 243 defining an upper surface 243a for contact with the abutment surface 274 of the lumen extension tip 246, and wherein a centrally-positioned opening or conduit 221 is defined for receiving the cylindrical body of the lumen extension tip 246. In example embodiments, the outer peripheral surface 272 is generally similar in diameter and generally parallel with at least a portion of the internal conduit of the syringe barrel 220. In example embodiments, a frictional fit is provided between the outer wall of the internal conduit of the barrel 220 and the outer peripheral surface 272 of the base portion 270, or at least when the abutment surface 274 is contacting the upper surface 243a of the platform 243. For example, to ensure fluids do not pass around the outer peripheral surface 272 and through the conduit 221 of the syringe coupling 240 (e.g., leaking from the coupling and not being contained within the internal lumen 248), an interference fit is generally provided between the at least a portion of the base 270 and the platform 243.

Figure 18:
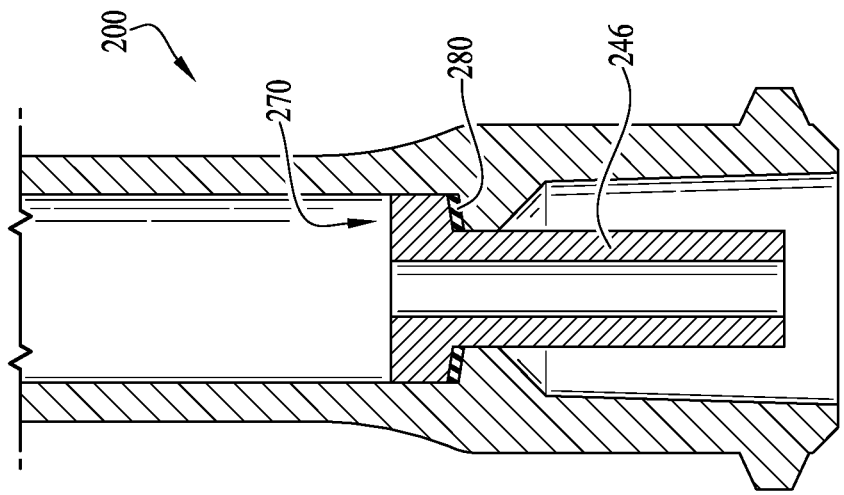
FIG. 18 shows a cross-sectional view of an enteral syringe with the lumen extension tip thereof having a sealing member according to another example embodiment of the present invention.

In some example embodiments, as depicted in FIG. 18, a seal ring or gasket 280 is generally provided for seating against the abutment surface 274 and around the cylindrical body 246, and thereby providing for an enhanced seal between the upper surface 243a and the abutment surface 274. In example embodiments, when the gasket 280 is provided, the outer diameter of the outer peripheral surface 272 need not be the exact same size or larger for providing an interference fit. However, in some example embodiments, the outer diameter of the outer peripheral surface 272 is generally substantially similar to the diameter of the internal conduit of the barrel 220 generally near the platform 243, for example, to provide an interference fit therebetween. In some example embodiments, the diameter of the internal conduit of the barrel 220 varies along its length, for example, at least partially varying or tapering along its length such that sufficient retraction of the lumen extension tip 246 within the internal conduit of the barrel 220 (see FIG. 17) will eventually cause the lumen extension tip 246 to become free from engagement with the internal conduit of the barrel 220. In some example embodiments, the outer peripheral surface 272 generally remains in contact with the outer surface of the internal conduit of the barrel 220.

For example, as depicted in FIG. 17, a non-ENFit connector IC is shown attempting to misconnect with the lumen extension tip 246. As the ISO 80369-3 standard facilitates a reduction of misconnections between different enteral connectors, configuring the lumen extension tip 246 to be a separate piece can further reduce or de-risk the likelihood of a misconnection, for example, whereby attempting to connect the non-ENFit connector IC to the tip 246 causes the lumen extension tip 246 to retract within the internal conduit of the barrel 220. In example embodiments, with the lumen extension tip 246 being movable within the internal conduit of the barrel 220, in the event of a user incorrectly attempting to couple non-ENFit connectors with the coupling 240 (and lumen extension tip 246 thereof), such misconnection is substantially (if not entirely) prevented, for example, since direct engagement with the lumen extension tip 246 causes retraction of the tip 246 relative to the internal conduit of the barrel 220. And thus, with the lumen extension tip 246 retracted within the internal conduit of the barrel, the syringe is incapable of properly functioning and thereby warning a user of the potential misconnection and/or preventing non-ENFit connectors from being unintentionally misconnected with the lumen extension tip. In example embodiments, the force required to cause retraction of the lumen extension tip 246 can be adjusted based on the interference provided between the lumen extension tip 246 (and the base 270 thereof) and the internal conduit of the barrel 220 (or with other portions of the syringe). For example, according to some example embodiments, only a relatively small force is required to cause retraction of the lumen extension tip 246. Alternatively, in other example embodiments, a larger force is required to cause retraction of the lumen extension tip 246 within the internal conduit of the barrel 220. Preferably, the interference provided between the lumen extension tip and the syringe can be adjusted as desired such that the desired force causes retraction of the lumen extension tip within the internal conduit of the barrel.

Figure 19:
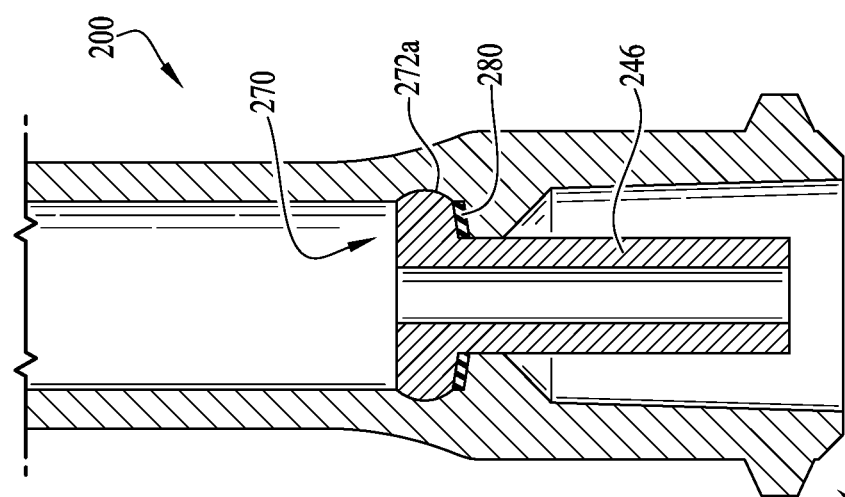
FIG. 19 shows a cross-sectional view of an enteral syringe with the lumen extension tip thereof having a sealing member and interengagement features according to another example embodiment of the present invention.
Figure 20:
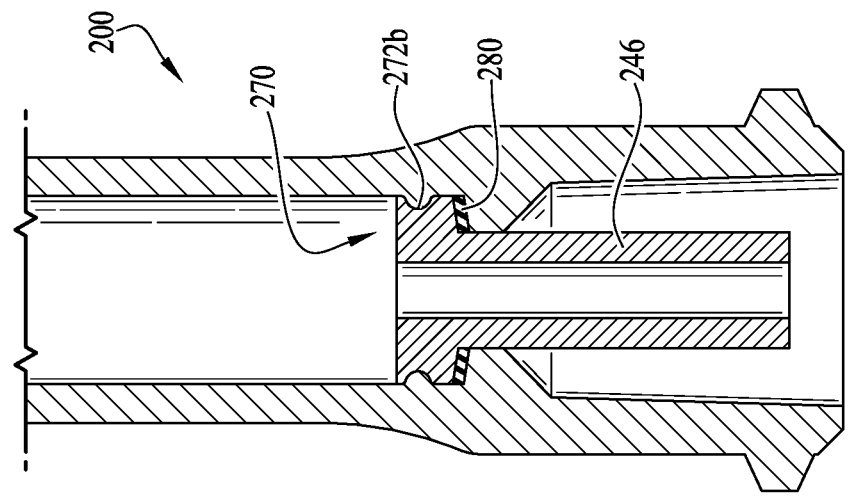
FIG. 20 shows a cross-sectional view of an enteral syringe with the lumen extension tip thereof having a sealing member and interengagement features according to another example embodiment of the present invention.
Figure 21:
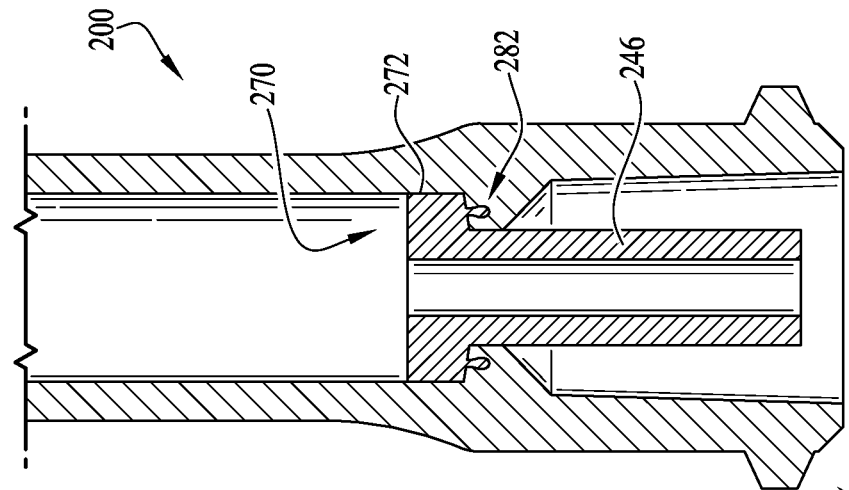
FIG. 21 shows a cross-sectional view of an enteral syringe with the lumen extension tip thereof having interengagement features according to another example embodiment of the present invention.

As depicted in FIGS. 19-21, the base 270 of the lumen extension tip 246 can preferably be configured in various forms such that coupling and/or sealing engagement is provided between the base 270 (or at least a portion of the lumen extension tip 246) and the internal conduit of the barrel 220 or platform 243. FIG. 19 shows the lumen extension tip 246 seated within the internal cavity and projecting coaxially within the coupling 240. In example embodiments, the base 270 comprises an outwardly curved peripheral surface 272a for engagement with a radiused recess formed in the outer surface of the internal conduit of the barrel 220. In alternate example embodiments, the interengagement provided between the outwardly curved peripheral surface 272a and the radiused recess provides a sufficient seal therebetween (see FIG. 19), and preferably provides for sufficient seating engagement therebetween. In some example embodiments, the interference between the outwardly curved peripheral surface 272a and the radiused recess is such that a non-ENFit connector attempting to misconnect with the lumen extension tip 246 causes the base 270 and the outwardly curved peripheral surface 272a of the lumen extension tip 246 to disengage the radiused recess and begin to move rearwardly within the internal lumen of the barrel 220 (e.g., similar to the tip 24 of FIG. 17).

Alternatively, as depicted in FIG. 20, the base 270 of the lumen extension tip 246 comprises an inwardly directed outer peripheral surface 272b for interengagement with a radiused ring or rib of the outer surface of the internal cavity of the barrel 220. Optionally, a seal ring 280 is provided between the abutment surface 274 and the upper surface 243a. According to another example embodiment, a protruding rib or ring 282 extends from the abutment surface 274 for interengagement within a circular recess formed within a portion of the platform 243 (see FIG. 21). Optionally, according to other example embodiments, the lumen extension tip 246 (e.g., cylindrical body and/or base) can be shaped and sized as desired, and can be configured for removable or permanent interengagement with the internal lumen of the barrel (or other portions of the syringe). Optionally, as described above, the interengagement between the lumen extension tip and the syringe is such that an attempted misconnection with a non-ENFit connector is de-risked by retraction of the lumen extension tip within the internal conduit of the barrel 220. In example embodiments, with the lumen extension tip 246 being separate and movable with respect to the syringe, the likelihood of non-ENFit connectors being unintentionally misconnected with the lumen extension tip 246 is substantially reduced. As such, the incidence of potential misconnections with other coupling formats, for example, luer slip couplings or other coupling formats, can be reduced or avoided. For example, in example embodiments, attempting to connect other coupling formats that are not configured according to a coupling substantially conforming to ISO 80369-3 design standard will cause the lumen extension tip 246 to move within the syringe, and thus, provide a warning the user and/or will not allow for connecting with the non-ENFit coupling format.

According to other example embodiments, the lumen extension tip 246 can comprise one or more engagement features for providing interengagement with the internal conduit of the barrel 220 (or other portions of the syringe 200), and the plunger movably mounted within the barrel 220 can preferably provide for manipulating or facilitating movement of the lumen extension tip 246 within the internal conduit of the barrel 220, for example, to provide for selective engagement/disengagement of the lumen extension tip 246 within the internal conduit of the barrel 220. According to example embodiments, one or more teeth or coupling features are provided on a portion of the base 270 for engagement with a portion of the plunger. And, one or more interengagement features are provided with the lumen extension tip 246 for coupling engagement with the internal conduit of the barrel 220 (or other portions of the syringe). Thus, according to some example embodiments, the plunger can engage the one or more coupling features of the base 270 such that the lumen extension tip 246 can be manipulated (or rotationally driven) to provide for selective engagement/disengagement of the lumen extension tip 246 with the syringe 200.

Figure 22:
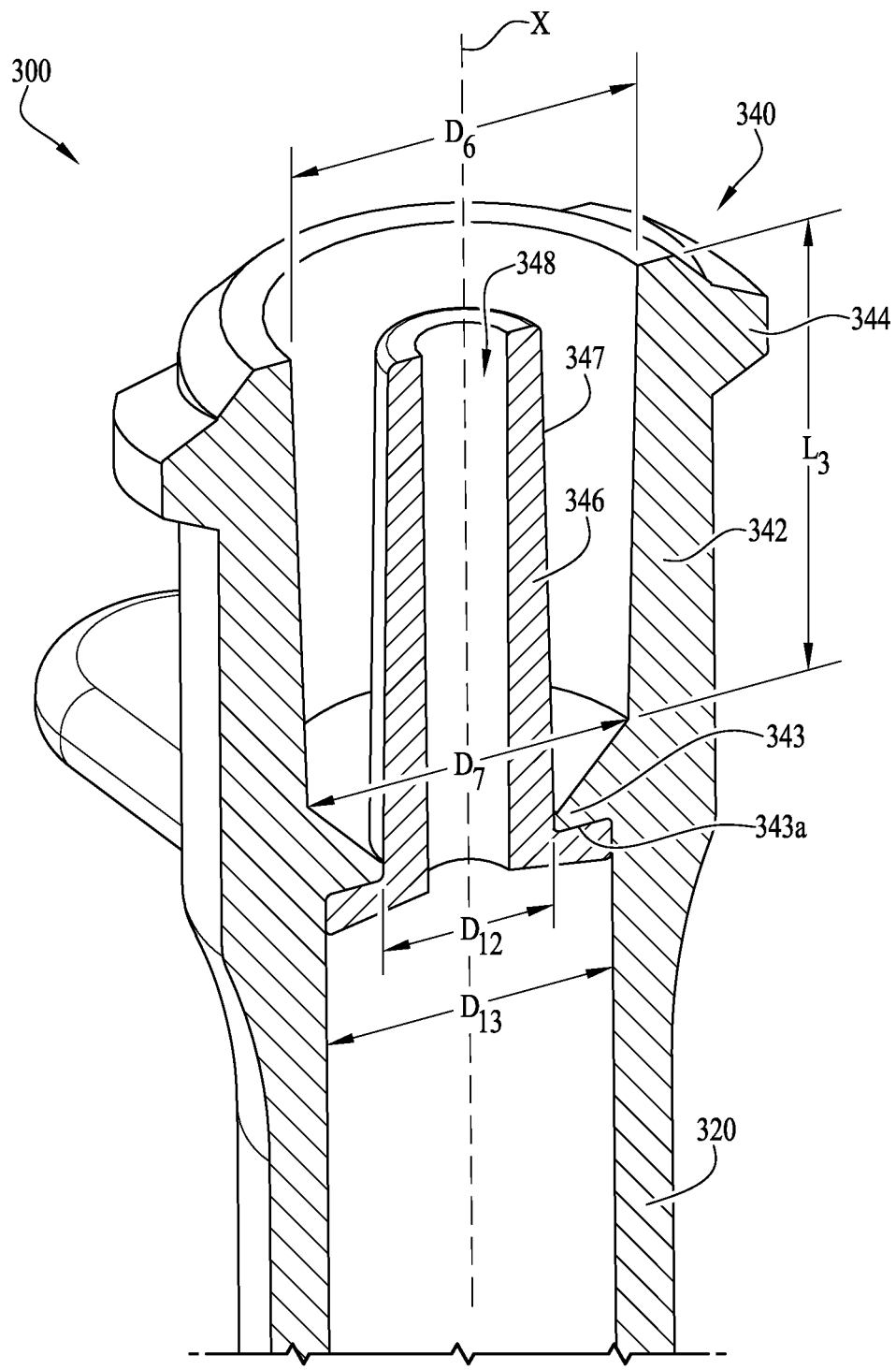
FIG. 22 is a perspective cross-sectional view of a portion of a syringe including an enteral dosing control coupling having a lumen extension tip seated and fully extending from the end of the syringe according to another example embodiment of the present invention.
Figure 23:
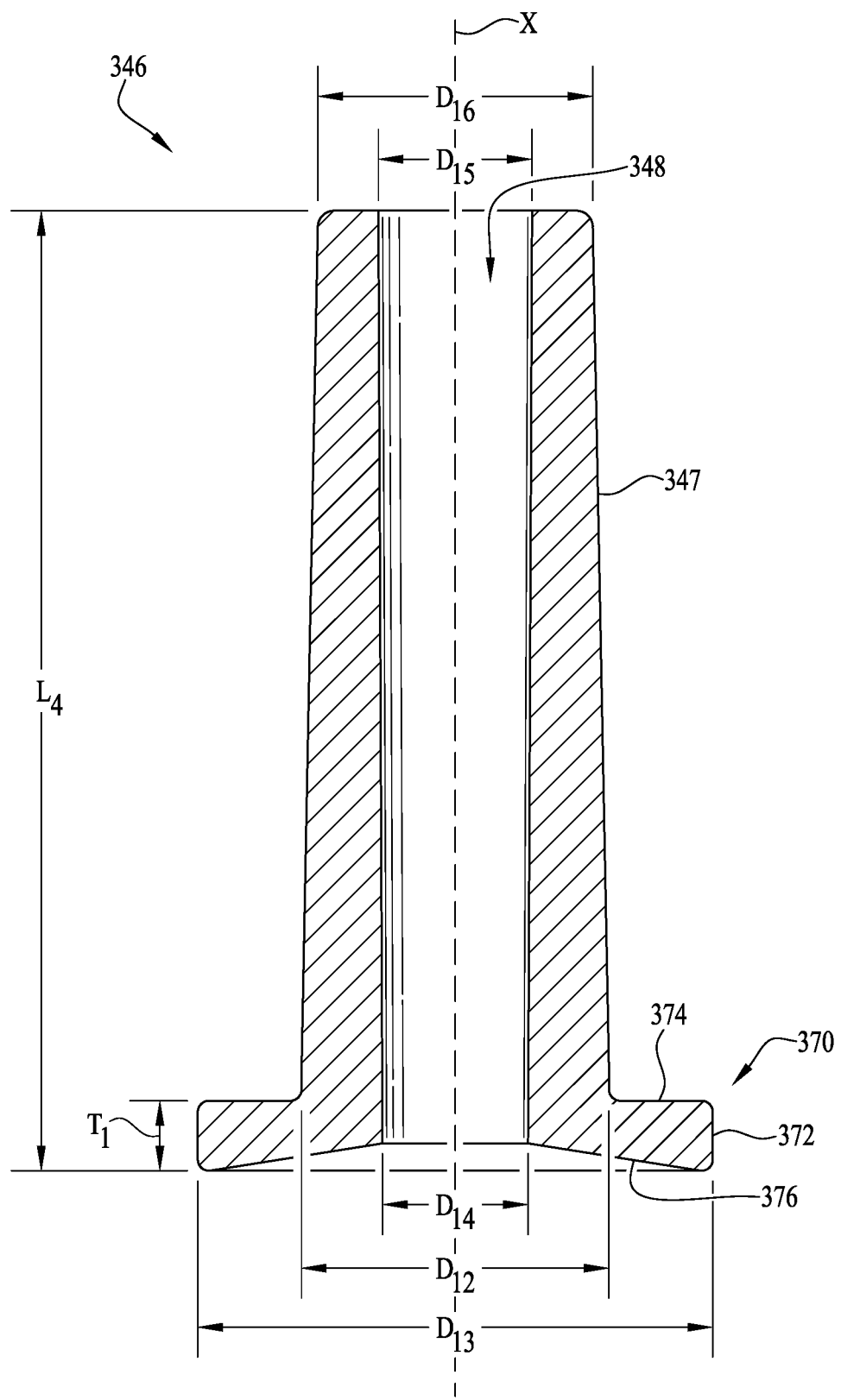
FIG. 23 is a cross-sectional view of the lumen extension tip portion of the syringe of FIG. 22.

FIGS. 22-23 show a syringe 300 comprising a lumen extension tip 346 according to another example embodiment of the present invention. In example embodiments, the syringe 300 is generally similar to the syringe 200 as described above. In example embodiments, the first and second internal diameters D6, D7 of the collar 340 and the length L3 defined therebetween are substantially similar as described above. For example, the first internal diameter D6 is about 5.69 millimeters, the second internal diameter D7 is about 5.26 millimeters, and the length L3 defined between the first and second internal diameters D6, D7 is about 7.14 millimeters. In example embodiments, the diameter D12 of the central opening of the syringe 300 (e.g., for receiving the lumen extension tip 346) is about 2.80 millimeters, and the diameter D13 of the internal conduit of the syringe barrel 320 is about 4.69 millimeters.

As depicted in FIG. 23, the lumen extension tip 346 is generally similarly shaped as described above and comprises a cylindrical body having a base 370 at an end thereof and comprising an internal lumen 348 extending entirely through the cylindrical body. In example embodiments, the outer diameter D13 of the internal conduit of the barrel 320 is substantially similar to the outer diameter D13 of the base 370, for example, which is about 4.69 millimeters. Thus, according to example embodiments, the outer diameter D13 of the base 370 is sized to provide for an interference, frictional fit with the internal conduit of the barrel 320. The base 370 comprises a thickness T1 of about 0.64 millimeters and the outer peripheral surface 372 is generally substantially flat and generally parallel relative to the axis X longitudinally extending along a length L4 of the tip 346. A bottom side of the base 270 comprises a slightly tapered surface that is generally angled towards the opening of the internal conduit 348. In example embodiments, the length L4 (defined between the ends of the tip 346) is about 8.76 millimeters. As similarly described above, the base 370 of the tip 346 comprises an abutment surface 374 for engagement with the upper surface 343a of the platform 343. The internal conduit 348 of the tip 346 comprises a first inner diameter D14 defined near the base 370 and a second inner diameter D15 the end of the tip. In example embodiments, the first inner diameter is about 1.33 millimeters and the second inner diameter D15 is about 1.40 millimeters. The outer diameter of the end of the tip 346 defines an outer diameter D16, which is about 2.51 millimeters according to one example embodiment. In example embodiments, the outer periphery of the cylindrical body of the tip 346 comprises a surface 347 that is provided for fitting within the internal cavity of a male hub H of an ISO 80369-3 formatted connector. In example embodiments, the end of the tip 346 generally near the outer diameter D16 con comprise a radiused edge or other curved or tapered feature. As depicted, a radiused edge is provided at the end portion of the tip 346.

FIGS. 24-27 show syringes 400, 500 comprising lumen extension tips 446, 546 according to additional example embodiments of the present invention. In example embodiments, the dosing control couplings (as described above) can be adapted for use with syringes of different sizes. For example, FIGS. 24-25 depicts a 3 milliliter syringe 400 comprising a syringe body 420, an ISO 80369-3 formatted enteral dosing control coupling 440 in the form of a modified female ENFit coupling. The lumen extension tip 446 can be integrally formed with the coupling as depicted, or in alternate embodiments can be a separate component. Similarly, FIGS. 26-27 show a 6 milliliter syringe 500 comprising a syringe body 520, an ISO 80369-3 formatted enteral dosing control coupling 540 in the form of a modified female ENFit coupling positioned offset from the barrel of the syringe. The lumen extension tip 446 can be integrally formed with the coupling. Alternatively, the lumen extension tips 446, 546 can be separate and movable with respect to the syringe, for example, as described above with respect to FIGS. 12-23. In example embodiments, the enteral dosing control couplings 440, 540 of the syringes 400, 500 can be applied to syringes of various volumes and shapes, for example, between about 0.5 milliliters-6 milliliters and wherein the dosing control couplings can be positioned concentrically, off-centered, or asymmetrical relative to the syringe body. In still other embodiments, a low-dose tip or dosing control coupling according to any of the embodiments as disclosed herein can be provided in connection with various other syringe formats including, for example syringes having non-circular barrel configurations (see U.S. patent application Ser. No. 14/224,297, incorporated herein by reference in its entirety).

Figure 28A:
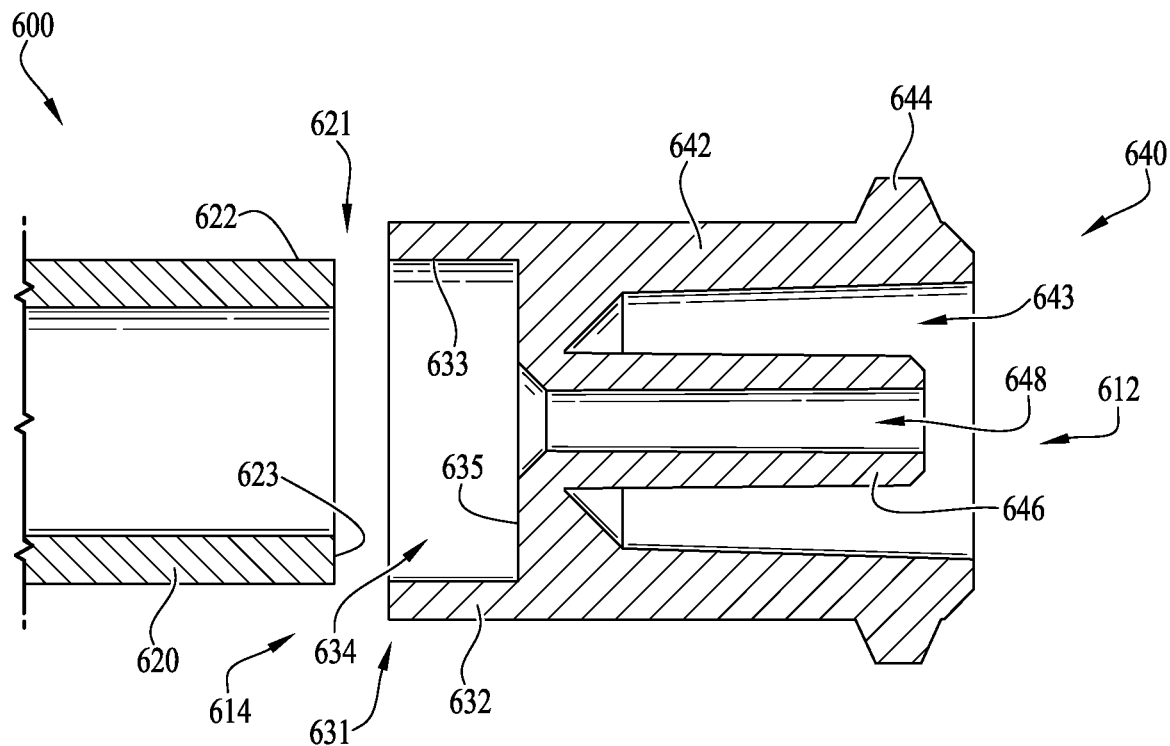
FIGS. 28A-B show cross-sectional view of an enteral syringe including an enteral dosing control coupling according to another example embodiment, showing an assembly view with components thereof disconnected and an assembled view with the components connected together.
Figure 28B:
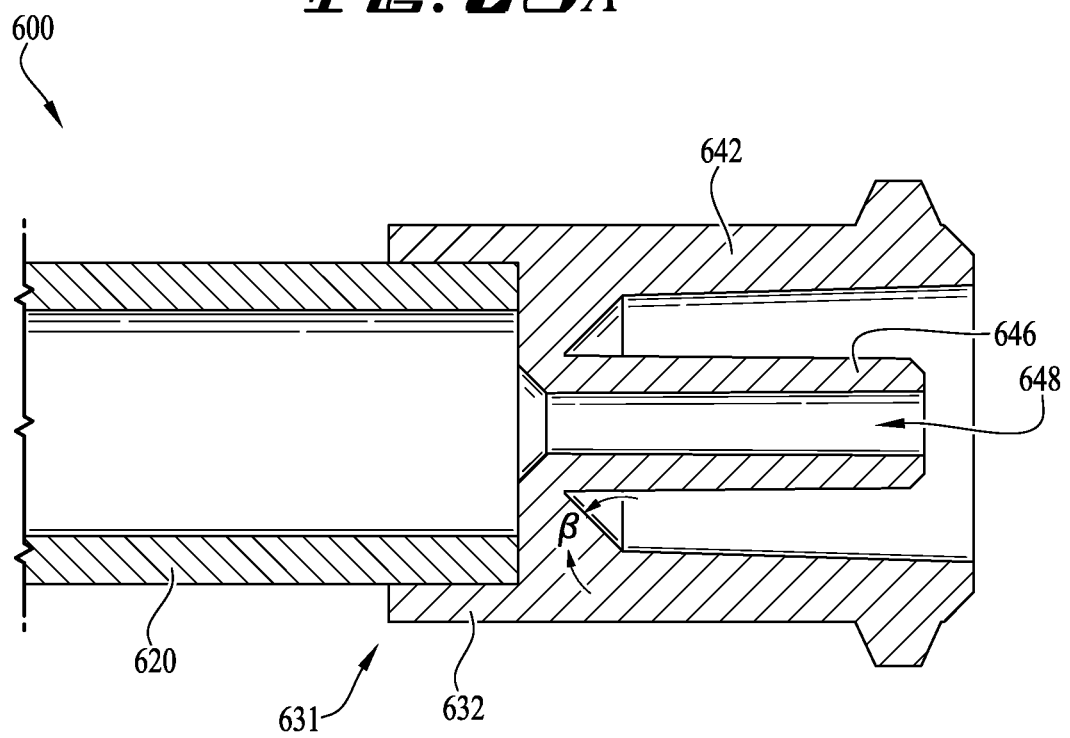

FIGS. 28A-B show an enteral syringe 600 comprising an enteral dosing control coupling or low-dose tip 646 according to an example embodiment of the invention. In example embodiments, the enteral syringe 600 includes a hollow cylindrical barrel 620 and an enteral dosing control coupling 640 for coupling with a proximal end of the barrel. According to the depicted example embodiment, the hollow cylindrical barrel 620 and the dosing control coupling 640 are separate pieces configured for sealingly engaging each other. Optionally, the barrel 620 and the coupling 640 can be one integral piece. As would be understood by one of ordinary skill in the art, the barrel 620 is adapted to receive a syringe plunger that is axially advanceable and retractable within the barrel to fill and dispense fluid into and from the syringe in typical fashion. In some example embodiments, the syringe can be provided for use with a syringe pump, for example, where one or more portions of the syringe and/or the plunger can be interengageable with one or more portions of the syringe pump for moving the plunger relative to the syringe to dispense fluids from the syringe.

In the depicted example embodiment, the coupling 640 generally comprises a modified ISO 80369-3 formatted coupling and is engageable with a compatible coupling element such as a corresponding male ISO 80369-3 formatted coupling M, as shown in FIG. 4. In example applications, the male ISO 80369-3 formatted coupling M can be part of a feeding or extension tube, a pharmacy cap, syringe (as will be described below) or other enteral fluid delivery equipment to which the syringe 600 is to be coupled.

In example embodiments, a front end 612 of the coupling 640 comprises a cylindrical outer collar 642 defining a hollow internal chamber 643, and a pair of helical coupling lugs 644 projecting outwardly from the exterior surface of the collar 642. Optionally, rather than lugs 644 projecting from the exterior surface of the collar, the exterior surface of the collar 642 can comprise helical threads generally extending about at least a portion of the exterior surface thereof, for example, like threads on a bolt, other types of conventional coupling members, etc. In some example embodiments, the exterior surface of the collar is entirely smooth without any lugs, for example, whereby a frictional fit (as described above) will be provided between the male ISO 80369-3 formatted coupling and the coupling 640. Optionally, other coupling elements can be provided on the collar as desired.

In example embodiments, the coupling 640 further comprises a lumen extension tip 646 that projects axially from a base portion of the coupling 640 and into the internal chamber of the collar 642. According to example embodiments, the lumen extension tip 646 is substantially coaxial and concentric with respect to the collar 642.

In example embodiments, a second end 614 of the coupling 640 comprises an end coupling 631 for engagement with an open end 621 of the barrel 620. For example, according to one example embodiment, the second end 614 comprises an end coupling 631 for sealingly engaging the open end 621 of the syringe barrel 620. In example embodiments, the end coupling 631 comprises a skirt or outer collar 632 defining a recess or cavity 634 and floor surface 635 therein for receiving the open end 621 of the barrel 620. In example embodiments, the collar 632 comprises an inner surface 633 that is configured for engagement with an outer surface 622 of the barrel 620, and an end surface 623 of the syringe abuts with the floor surface 635 of the cavity 634. Thus, according to some example embodiments, both the outer surface 622 and end surface 623 generally sealingly engage or at least abut with the respective inner surface 633 and floor surface 635 of the collar 632. According to one example embodiment, the outer collar member 642 and the collar 632 have a substantially similar outer diameter, for example, such that the transition therebetween (along the length of the coupling 640 from the first end 612 to second end 614) is substantially unnoticeable or at least substantially smooth between the ends. In example embodiments, the collar 632 of the end coupling 631 is substantially similar to an outer dimension of the female ISO 80369-3 formatted coupling.

An internal lumen or enteral fluid delivery conduit 648 extends through the lumen extension tip 646 for fluid communication to and from the contained volume of the barrel 620, allowing fluid delivery in and out of the barrel 620. As similarly shown and described above, when the coupling 640 is engaged with a male ISO 80369-3 formatted coupling M, the lumen extension tip 646 is received within the lumen of a male coupling hub H (in effect becoming a male coupling element within the "female" lumen of the male ISO 80369-3 formatted coupling). The lumen extension tip 646 is generally cylindrical or tubular and includes an internal surface defining the lumen or fluid delivery conduit 648, a cylindrical or slightly tapered external surface, and a distal tip at its free end. The outer coupling collar 642 is also generally cylindrical or tubular, and at least partially surrounding the lumen extension tip 646. The collar 642 comprises an internal surface confronting and spaced a distance apart from the external surface of the lumen extension tip, and further comprises an external surface optionally comprising the lugs 644 or other coupling or connection features, and an outer rim at its distal free end. The internal dimension of the collar 642 is greater than the external dimension of the lumen extension tip 646, such that a space therebetween forms a receiver 643 for a cooperating portion of a compatible coupling element, for example a male ISO 80369-3 formatted coupling. The lumen extension tip 646 is positioned generally concentrically and coaxially within the collar 642, and the lumen 648 extends generally centrally through the lumen extension tip also concentric and coaxial with the collar.

In example embodiments, the dosing control coupling 640 is generally a separate piece, and during the manufacture thereof the dosing control coupling 640 is generally sealingly engaged with the syringe barrel 620 to form the syringe 600. According to one example embodiment, the dosing control coupling 640 can be permanently and sealingly attached to the barrel 620, for example by co-molding, over-molding, welding or fusing, adhesives, glues, or other available attachment means. Optionally, the dosing control coupling 640 and syringe barrel 620 can comprise one or more interengagement features or other coupling elements such that the dosing control coupling 640 can be either permanently or removably attached to the barrel 620.

In alternate example embodiments, the lumen extension tip 646 can be a separate piece and installable with the dosing control coupling 640. Thus, according to some example embodiments, the lumen extension tip 646, the dosing control coupling 640 and the barrel 640 are separate pieces of the syringe 600. According to another example embodiment as depicted in FIGS. 28A-B, the barrel 620 and the dosing control coupling 640 are separate pieces, and the lumen extension tip 646 is integral with the dosing control coupling 640. And as shown in FIG. 5 the dosing control coupling, lumen extension tip and barrel are one integral syringe. Thus, according to example embodiments of the present invention, the lumen extension tip can be integrally formed with the integral coupling or the separate coupling, and further optional the lumen extension tip can be a separate piece for use with the dosing control coupling when the dosing control coupling is integral with the syringe or when the dosing control coupling is a separate piece.

FIGS. 29A-C show an enteral syringe 700 comprising an enteral dosing control coupling or low-dose tip 746 according to an example embodiment of the invention. In example embodiments, the enteral syringe 700 is substantially similar to the syringe 10 as described above (see FIG. 5). In some example embodiments, the syringe 700 can be configured substantially similar to the enteral syringe 600, for example, wherein the dosing control coupling is a separate piece and attached to the open end of the syringe.

In example embodiments, the syringe 700 comprises hollow cylindrical barrel 720, a base flange 730 at a distal end of the barrel, and the enteral dosing control coupling 740 at a proximal end of the barrel. In example embodiments, the enteral dosing control coupling 740 comprises a cylindrical outer collar 742 defining a hollow internal chamber 743, and a pair of helical coupling lugs 744 projecting outwardly from the exterior surface of the collar 742. Optionally, rather than lugs 744 projecting from the exterior surface of the collar, the exterior surface of the collar 742 can comprise helical threads generally extending about at least a portion of the exterior surface thereof, for example, like threads on a bolt, other types of conventional coupling members, etc. In some example embodiments, the exterior surface of the collar is entirely smooth without any lugs, for example, whereby a frictional fit (as described above) will be provided between the male ISO 80369-3 formatted coupling and the coupling 740. Optionally, other coupling elements can be provided on the collar as desired.

In example embodiments, the coupling 740 further comprises a lumen extension tip 746 that projects axially from a base portion of the coupling 740 and into the internal chamber of the collar 742. According to example embodiments, the lumen extension tip 746 is substantially coaxial and concentric with respect to the collar 742.

An internal lumen or enteral fluid delivery conduit 748 extends through the lumen extension tip 746 for fluid communication to and from the contained volume of the barrel 720, allowing fluid delivery in and out of the barrel 720. As similarly shown and described above, when the coupling 740 is engaged with a male ISO 80369-3 formatted coupling, the lumen extension tip 746 is received within the lumen of a male coupling hub (in effect becoming a male coupling element within the "female" lumen of the male ISO 80369-3 formatted coupling). The lumen extension tip 746 is generally cylindrical or tubular and includes an internal surface defining the lumen or fluid delivery conduit 748, a cylindrical or slightly tapered external surface, and a distal tip at its free end. The outer coupling collar 742 is also generally cylindrical or tubular, and at least partially surrounding the lumen extension tip 746. The collar 742 comprises an internal surface confronting and spaced a distance apart from the external surface of the lumen extension tip, and further comprises an external surface optionally comprising the lugs 744 or other coupling or connection features, and an outer rim at its distal free end. The internal dimension of the collar 742 is greater than the external dimension of the lumen extension tip 746, such that a space therebetween forms a receiver 743 for a cooperating portion of a compatible coupling element, for example a male ISO 80369-3 formatted coupling. The lumen extension tip 746 is positioned generally concentrically and coaxially within the collar 742, and the lumen 748 extends generally centrally through the lumen extension tip also concentric and coaxial with the collar.

In example embodiments, the enteral syringe 700 can further comprise a flange 722 optionally extending transversely outward from the outer collar 742 (or base portion thereof). In example embodiments, rather than the flange 722 only extending along a portion of the outer periphery of the syringe barrel (see FIG. 2), the flange 722 generally extends around the entirety of the outer periphery of the outer collar (or base portion thereof). For example, according to example embodiments of the present invention, the syringe 700 is configured such that the dosing control coupling 740 is a separate piece and assembled for permanent and sealed engagement with the barrel 720. According to one example embodiment, a spacer 721 is provided below the flange 722, and wherein the spacer 721 extends and transitions into a base flange 723 that generally tapers outwardly to the dimension of the syringe barrel 720. In example embodiments, a seal 724 is provided to sealingly and permanently attach the base flange 723 (and enteral dosing control coupling 740) to the syringe barrel 720 (e.g., by co-molding, over-molding, welding or fusing, adhesives, glues, or other available attachment means). In alternate example embodiments as similarly described with respect to the enteral syringe 600, the enteral dosing control coupling 740 and be configured for removable engagement with the syringe barrel 720. Optionally, according to additional example embodiments, the dosing control coupling and/or lumen extension tip (as described with respect to syringes 600, 700) can be attached or secured to a syringe barrel as desired, for example, by attachment to the barrel, the barrel tip, a protrusion or other feature of the barrel, or other barrel fittings, couplings, spacers, flanges, or other aspects and features of any available syringe barrel. In some example embodiments as similarly described above, the syringe can be provided for use with a syringe pump, for example, where one or more portions of the syringe and/or the plunger can be interengageable with one or more portions of the syringe pump for moving the plunger relative to the syringe to dispense fluids from the syringe.

FIGS. 30-35 show a plurality of syringes comprising various couplings according to example embodiments of the present invention. In example embodiments, the coupling 814 of the syringe 800 of FIG. 30 generally comprises a modified female ENFit coupling substantially conforming to ISO design standard 80369-3, and is engageable with a compatible coupling element such as a corresponding male ISO 80369-3 formatted coupling M, as shown in FIG. 1. In example embodiments, the collar 816 of the modified female ENFit coupling does not comprise ribs for engagement with the threaded collar portion of the male ISO 80369-3 formatted coupling, but instead comprises a smooth outer surface and smooth transition to the outer surface of the syringe body. Furthermore, the modified female ENFit coupling comprises a lumen extension tip 817 as described above. In some example forms, as depicted in FIG. 31, the coupling 914 of the syringe 900 comprises only a lumen extension tip 916 defining a lumen 918 extending therethrough, for example, for compatible engagement within the internal conduit of the male ISO 80369-3 formatted coupling M. According to one example embodiment, the lumen extension tip 916 extends a length L5 of between about 5.5 millimeters to about 9.5 millimeters. In some example embodiments, as depicted in FIG. 32, the coupling 1014 of the syringe 1000 extends along the elongate axis X a length L6 of between about 5 millimeters to about 15 millimeters. In example embodiments, the coupling 1014 comprises a stepped profile comprising a first coupling portion 1020, a second coupling portion 1022, and a third coupling portion 1024. In example embodiments, the stepped profile comprises generally smooth and radiused transitions between the coupling portions.

In example embodiments, the first coupling portion 1020 comprises a transfer port substantially sized and shaped similarly lumen extension tip 916 as described above. The second coupling portion 1022 is preferably sized and shaped for compatible interengagement with enteral-only (EO) formatted couplings, and the third coupling portion 1024 is preferably sized and shaped for compatible interengagement with ISO 80369-3 formatted couplings (e.g., dimensionally generally similar to ISO 80369-3 formatted male transfer port). Thereafter the third coupling portion 1024, an outer periphery portion of the coupling 1014 generally tapers outwardly to the syringe body 1010. Thus, according to example embodiments, the coupling 1016 preferably comprises a plurality of coupling portions for providing compatible coupling engagement with a plurality of enteral couplings or formats (e.g., enteral-only (EO) or ISO 80369-3 format). Optionally, a plunger can be sized and shaped such that the lumen 1018 is entirely occupied with the plunger when fully inserted within the barrel 1010. U.S. patent application Ser. No. 15/652,742 is incorporated herein by reference and shows a syringe-type delivery device comprising a plurality of coupling portions and a plunger for compatible use therewith.

As recited above, in example embodiments the delivery of fluid travels in a direction such that fluid moves from a female ISO 80369-3 formatted coupling to a male ISO 80369-3 formatted coupling, for example as shown in the embodiments of FIGS. 1-27 (e.g., fluid traveling from a syringe (female ISO 80369-3 formatted coupling) to a coupling (male ISO 80369-3 formatted coupling) for delivery to the patient). However, according to additional example embodiments of the present invention, fluid delivery from the syringe to a coupling or fluid delivery conduit is configured such that fluid moves from a male ISO 80369-3 formatted coupling to a female ISO 80369-3 formatted coupling. For example, according to additional example embodiments of the present invention, the end coupling of the syringe is a male ISO 80369-3 formatted coupling, and the connector, coupler, other couplings, etc. can comprise female ISO 80369-3 formatted couplings (as will be described below).

FIGS. 31-59C show a plurality of enteral syringes and connectors including fluid transfer connectors (e.g., syringe-to-syringe connectors, transfer caps), and capping or closure components (e.g., tip caps, fluid transfer connectors, etc.) according to additional example embodiments of the present invention. For example, as depicted in FIGS. 33-36, the syringes 1100, 1200 comprise a modified male ENFit coupling substantially conforming to ISO design standard 80369-3, for example, rather than having a modified female ENFit coupling substantially conforming to ISO design standard 80369-3 (as shown in FIGS. 1-27).

In example embodiments, the syringe 1100 can comprise a male ISO 80369-3 coupling 1114, for example, which can comprise an outer collar portion 1120 with an internally threaded portion 1122 and a centrally-positioned male coupling hub 1116 extending along an elongate axis X, and a lumen 1118 defined within the male coupling hub 1116. Optionally, a protrusion or tab 1130 can extend from a portion of the coupling 1114 (see FIGS. 33-34). According to another example embodiment, the coupling of the syringe 1200 only comprises a male coupling hub 1216 and defines a lumen 1218 extending through the hub 1216.

According to example embodiments of the present invention, the male ISO 80369-3 formatted couplings 1216 of the syringes 1200 are substantially similar to the male coupling M (e.g., see FIGS. 3A-B and 4 showing a male coupling M and example dimensions thereof). In some example embodiments, the coaxial connection collar 1120 of FIGS. 33-34 can be replaced with one or more clips or generally flexible tabs or other engagement features for removable engagement with the female ISO 80369-3 formatted couplings. According to example embodiments, the one or more clips can provide for dual-function engagement with the female ISO 80369-3 formatted coupling. For example, the dual-function engagement can provide for rotationally engaging the male and female coupling together or for directly pressing one of the couplings relative to the other of the couplings, for example a "press-in" engagement such that the one or more clips resiliently flex to provide for passage of the one or more protrusions or ribs formed on the outside surface of the collar of the female coupling. Optionally, the one or more clips can provide for removable or permanent engagement with a female ISO 80369-3 formatted coupling. U.S. patent application Ser. No. 15/454,761, U.S. patent application Ser. No. 15/078,674, U.S. patent application Ser. No. 15/185,583, U.S. patent application Ser. No. 14/844,922, U.S. Design patent application Ser. No. 29/521,665, and U.S. Design patent application Ser. No. 29/533,173 are incorporated herein by reference and disclose various clipped, snap-on and dual-action attachment and removal mechanisms for replacement with the coaxial connection collars 1120 of the male ISO 80369-3 coupling for the syringes of FIGS. 33-34. Optionally, one or more of the ends of the couplings can be provided with tabs or clips for providing permanent engagement between the coupling and the compatible connector, for example, when it is intended to prevent removal of the coupling 40 (and syringe 10 thereof) from the compatible connector after use. Further optional, according to some example embodiments of the present invention, the coupling can comprise one or more channels or grooves, for example, that are generally formed on an outer portion of the coaxial connection collar, for providing for engagement with one or more teeth, ribs, fingers, or engagement members or tabs, for example, to provide for additional engagement between the connection of the male and female ISO 80369-3 formatted couplings. Thus, according to some example embodiments of the present invention, the outer coaxial connection collar can be utilized as a bayonet fitting for further engagement with one or more portions of the female ISO 80369-3 formatted coupling.

According to some example embodiments, the syringes of FIGS. 30-35 can preferably be utilized as syringe-type fluid delivery devices for orally administering fluids, food, medicine or other contents within the syringe barrel to the mouth of a human or animal patient. U.S. patent application Ser. No. 15/652,742 discloses various syringe-type delivery devices and are incorporated herein by reference in their entirety.

FIGS. 37A-45D show a plurality of male-to-male, syringe-to-syringe and ISO 80369-3 formatted couplings according to additional example embodiments of the present invention. For example, when it is desired to connect or transfer fluids from one syringe to another syringe (for example, the syringes of FIGS. 33-36), or when it is desired to couple together two male ISO 80369-3 formatted connectors, the syringe-to-syringe couplers as depicted herein can provide for the removable or permanent coupling engagement of two male ISO 80369-3 formatted connectors.

According to some example embodiments as shown in FIGS. 37A-41D, the syringe-to-syringe couplers 1300, 1400, 1500, 1600 and 1700 each comprise a connector member having a generally elongate body extending along a longitudinal axis X. In example embodiments, a first end of the connector member comprises a female ISO 80369-3 formatted coupling and the second end of the connector comprises a female ISO 80369-3 formatted coupling. Optionally, according to other example embodiments (as will be described in detail below), one of the ends of the couplers can be configured for engagement with syringes or other coupling features formatted differently and/or not formatted with ISO 80369-3 format. Preferably, the couplers can be sized and shaped as desired, for example, for facilitating gripping the coupler, for example at the time of installation or removal. In some example embodiments, one or both of the ends can be fully threaded, can comprise outer ribs or lugs, or can be substantially smooth for fictional engagement with a male ISO 80369-3 formatted coupling. In some example embodiments, one or both of the female ISO 80369-3 formatted ends of the couplings can comprise a lumen extension tip, for example, as depicted above with respect to FIGS. 1-32. In some example embodiments, where only one side of the ends of the coupling comprises a lumen extension tip, the lumen extension tip can be movable relative to the coupling for example, to generally cause retraction within the end thereof when a misconnection is attempted.

FIGS. 37A-D show a male-to-male coupler 1300 according to one example embodiment of the present invention. In example embodiments, the coupler 1300 comprises a coupling member 1302 comprising an elongate body 1304 extending along the longitudinal axis X from a first end 1310 to a second end 1320 and defining a lumen 1340 extending therethrough. In example embodiments, the elongate body 1304 comprises a length L7 of between about 14 millimeters to about 30 millimeters, for example between about 16 millimeters to about 19 millimeters according to one example embodiment of the present invention. In example embodiments, the first end 1310 comprises a female ISO 80369-3 formatted coupling and the second end 1320 comprises a female ISO 80369-3 formatted coupling. As described in detail below, the first and second ends 1310, 1320 comprise cylindrical outer collars 1314, 1324 defining hollow internal chambers 1312, 1322 that are sized and shaped to receive male ISO 80369-3 formatted couplings. Thus, in example embodiments, the couplings as described herein can be configured for sealingly coupling or engaging together two male ISO 80369-3 formatted couplings, for example, such that fluids from one of the male ISO 80369-3 formatted couplings can be transferred (via the coupling 1300) to the other male ISO 80369-3 formatted coupling.

In example embodiments, the coupling 1300 can serve to connect two syringes together, for example, two syringes wherein each comprises a male ISO 80369-3 formatted coupling, or can serve for connecting the male ISO 80369-3 formatted coupling of a syringe (see FIGS. 33-35) to an ISO 80369-3 formatted coupling or system, for example, having a formatted fluid flow configuration (e.g., fluids flowing from female ISO 80369-3 coupling to male ISO 80369-3 coupling). For example, according to some example embodiments of the present invention, the coupling 1300 can comprise a first end comprising a female formatted coupling for connecting with a syringe comprising a male formatted coupling, and a second end thereof can comprise a female ISO 80369-3 formatted coupling. Thus, according to certain example embodiments of the present invention, the coupling can preferably comprise an end having a female ISO 80369-3 formatted coupling, and another end comprising a format other than the ISO 80369-3 format for compatible engagement with other coupling formats. For example, according to example embodiments of the present invention, the couplers 1300-2100 can be configured to be adapters, for example, such that enteral syringes and other enteral feeding components, etc. can be adapted to the ISO80369-3.

Referring back to FIGS. 37A-D, according to example embodiments as similarly described above (see FIG. 5), each end 1310, 1320 comprises a first internal diameter D6, a second internal diameter D7, a third internal diameter D9, a length L3, an outer coupler diameter D10, and angle β. According to one example embodiment, the first internal diameter D6 is about 5.69 millimeters, the second internal diameter D7 is about 5.26 millimeters, the third internal diameter D9 is about 2.85 millimeters, the length L3 is about 7.14 millimeters, the outer coupler diameter D10 is about 8.10 millimeters, and the angle β is about 45 degrees. Optionally, according to additional example embodiments of the present invention, the ends 1310, 1320 of the coupler 1300 can be sized and shaped as desired.

Figure 37A:
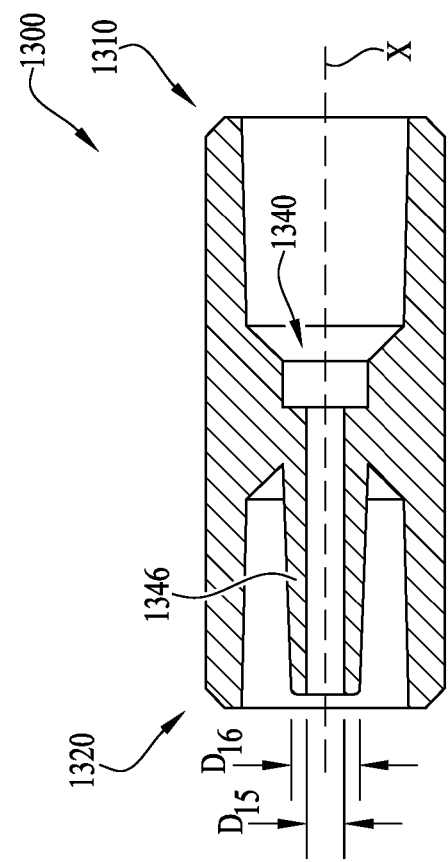
FIGS. 37A-D show cross-sectional views of enteral couplers according to example embodiments of the present invention.
Figure 37B:
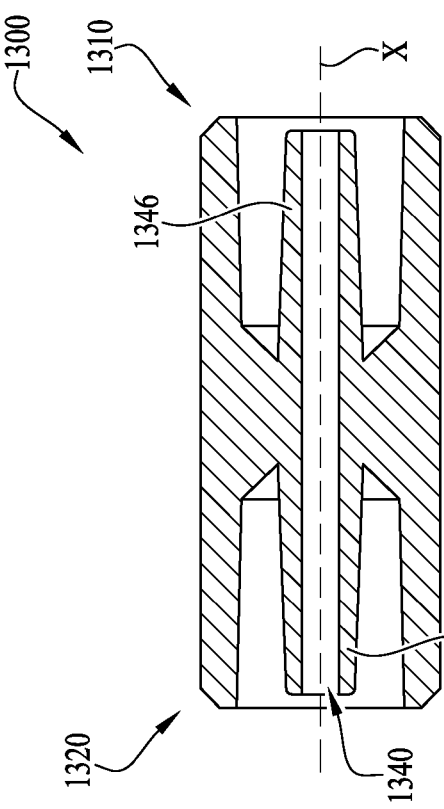
Figure 37C:
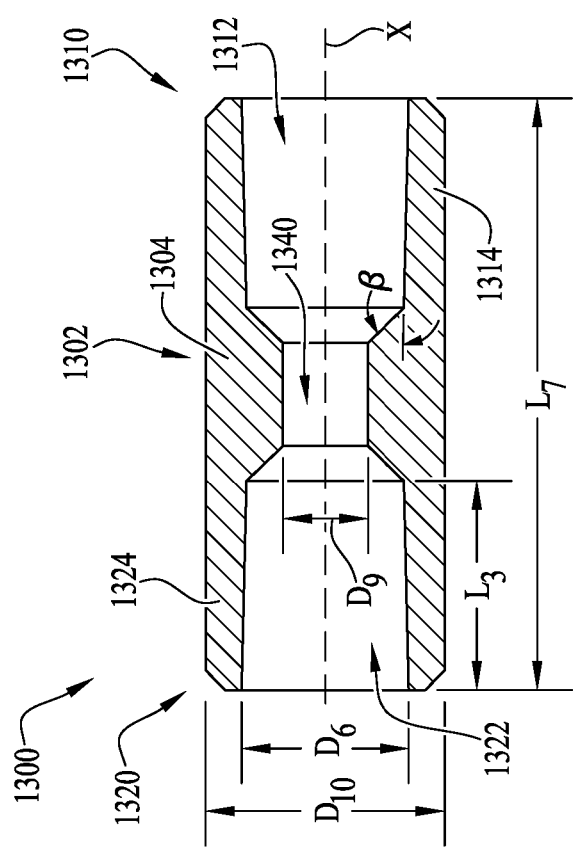
Figure 37D:
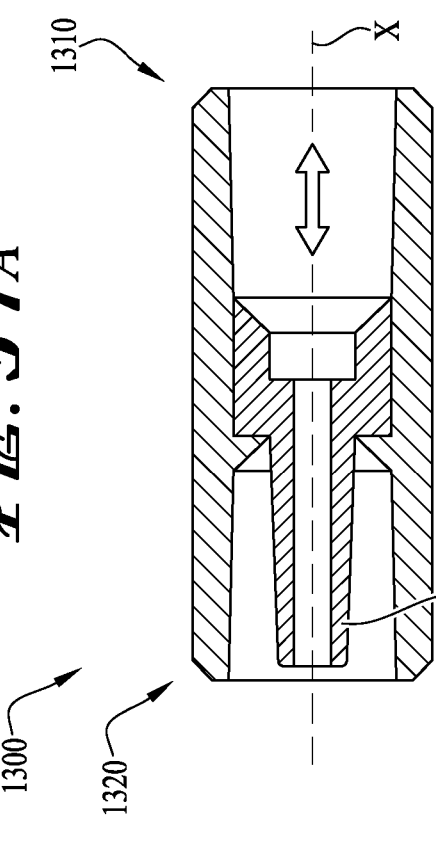
Figure 39B:
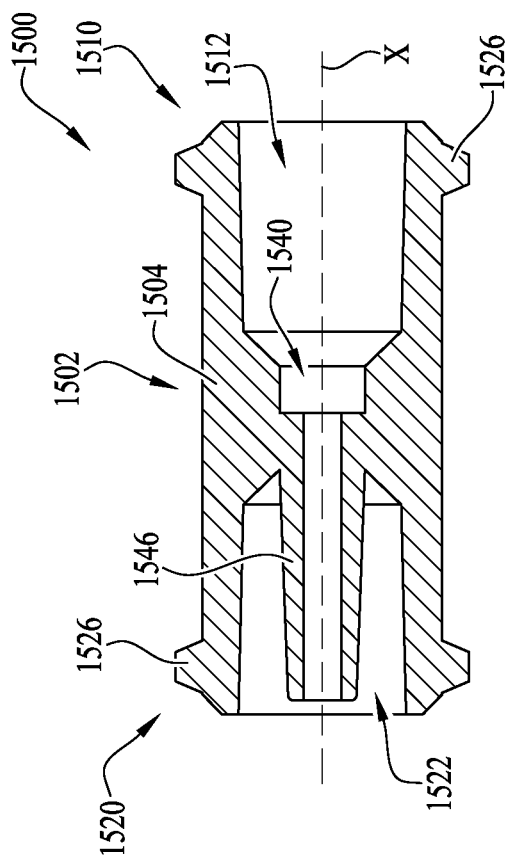
FIGS. 39A-D show cross-sectional views of enteral couplers according to example embodiments of the present invention.
Figure 39D:
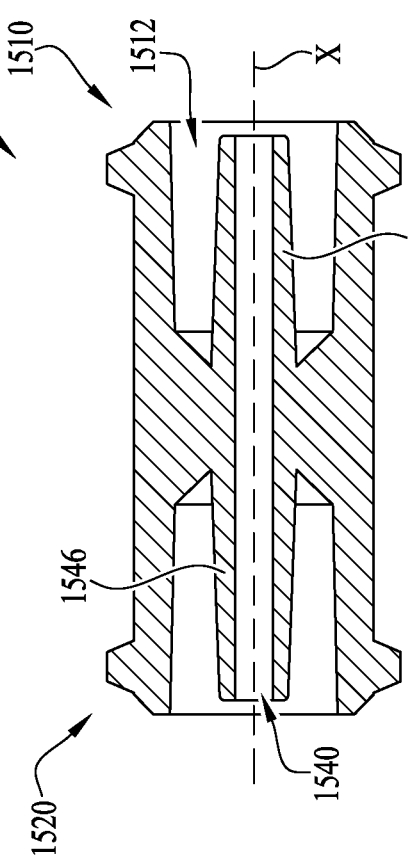
Figure 39A:
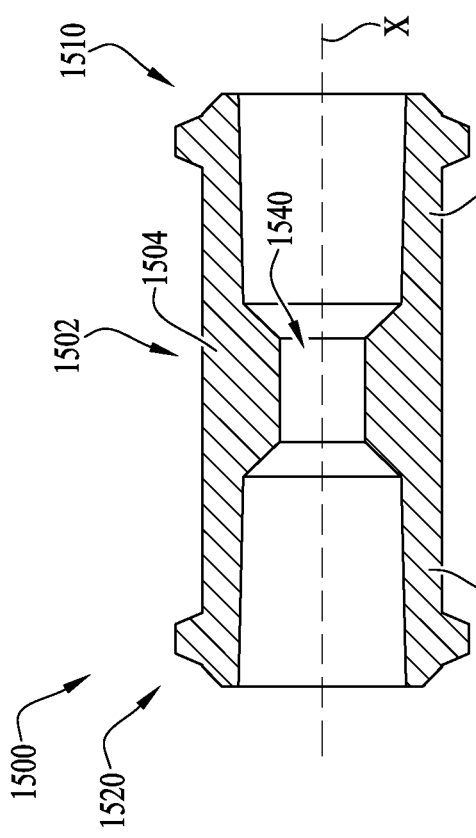
Figure 39C:
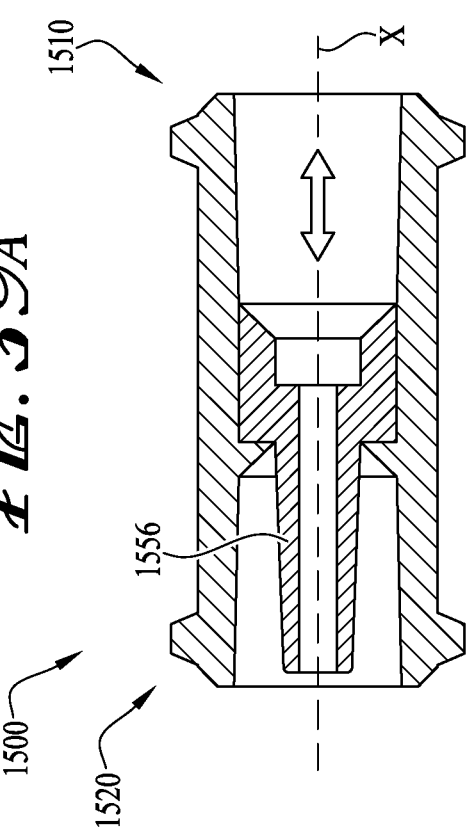
Figure 40A:
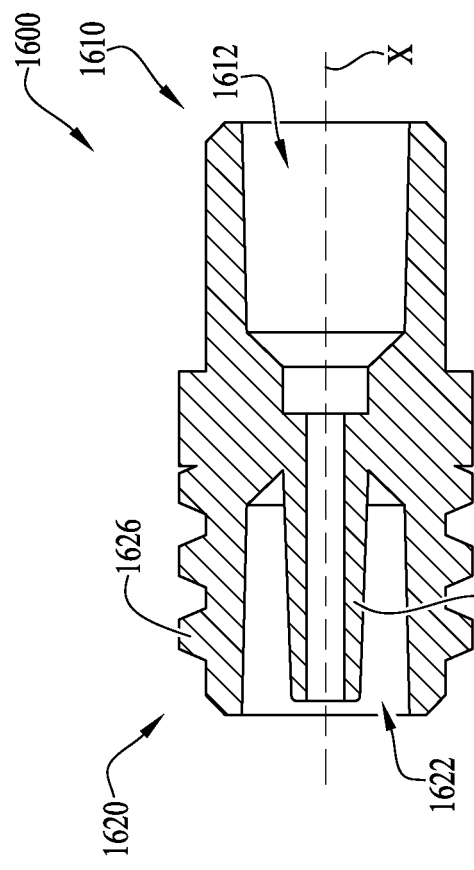
FIGS. 40A-D show cross-sectional views of enteral couplers according to example embodiments of the present invention.
Figure 40B:
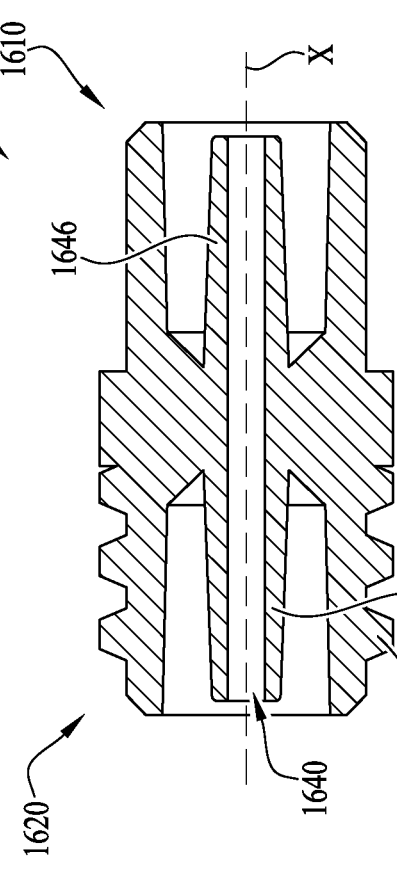
Figure 40C:
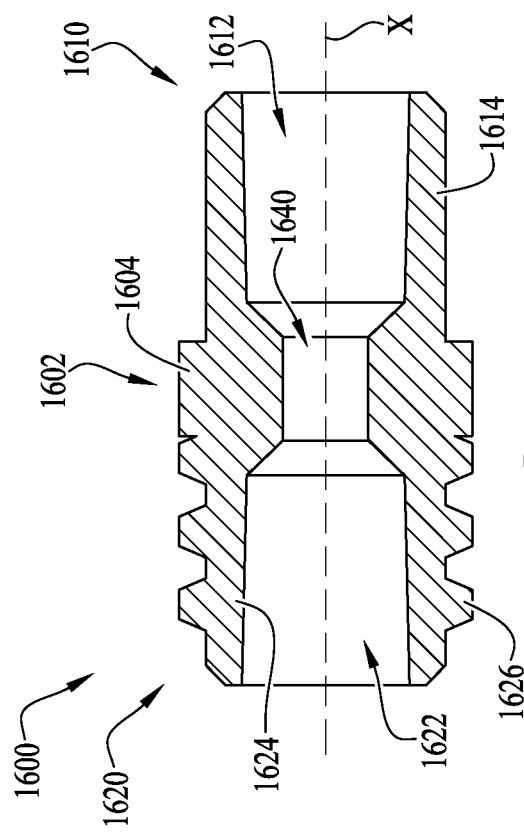
Figure 40D:
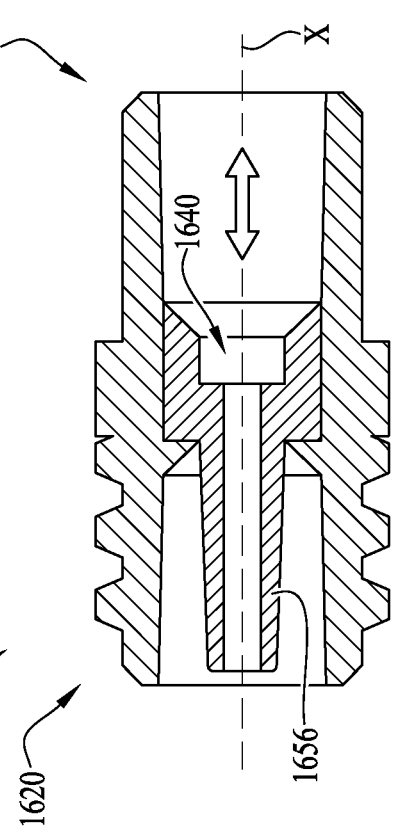

FIG. 37B shows the coupler 1300 comprising a lumen extension tip integrally connected with the female ISO 80369-3 formatted coupling of the second end 1320. As similarly described above and according to one example embodiment of the present invention, the lumen extension tip 1346 comprises an outer diameter D16 and an internal diameter D15 defining the lumen 1340 extending therethrough. The lumen extension tip extends along the elongate axis X and is coaxially aligned and concentric with the collar 1324. Optionally, as depicted in FIG. 37C and further described and detailed above, the lumen extension tip 1356 of the second end 1320 can be movable relative to the coupling 1300 and allow for the retraction thereof towards the first end 1310 when a misconnection is attempted (see FIGS. 12-23). FIG. 37D shows a coupling 1300 comprising a lumen extension tip 1346 at each end 1310, 1320 thereof. A lumen 1340 extends entirely between the ends 1310, 1320 to allow for fluid communication therethrough, for example, such that dosing control inaccuracies are substantially eliminated to provide for accurate dosing control.

FIGS. 38A-D show a coupler 1400 that is substantially similar to the coupling 1300. In example embodiments, the outer collar 1424 of the second end comprises one or more protrusions or ribs 1426 formed on the outside surface thereof. Optionally, both the first and second ends 1410, 1420 can comprise ribs 1424. For example, FIGS. 39A-D shows a coupler 1500 substantially similar to the couplings 1300, 1400, and comprising one or more protrusions or ribs 1526 formed on outside surfaces of each collar 1514, 1524 of both the first and second ends 1510, 1520. In example embodiments, the couplers 1500 are configured such that the first and second ends 1610, 1620 comprise female ISO 80369-3 formatted couplings. In alternate example embodiments, the second end 1520 of the coupling comprises a female ISO 80369-3 formatted coupling (optionally comprising permanent or removable lumen extension tip 1546, 1556), and the first end 1510 comprises a coupling format other than the ENFit ISO 80369-3 coupling format. For example, according to example embodiments, the first end 1510 of the coupling 1500 comprises a coupling format other than ISO 80369-3, and wherein syringe or delivery device comprising the coupling format other than ISO 80369-3 can sealingly connect with the first end 1510 of the coupling 1500, and thereby providing an adaptor such that coupling formats other than ISO 80369-3, for example, syringes and delivery devices (with other threaded enteral coupling formats), are connectable with ISO 80369-3 formatted couplings. According to further example embodiments, the lumen extension tip 1546, 1556 provides reduction to the volume of the conduit 1540, for example, such that dosing control inaccuracies are substantially eliminated to provide for accurate dosing control.

According to one example embodiment and shown in FIGS. 40A-D, rather than the second end 1420 of the coupling 1400 comprising one or more protrusions 1426 (see FIGS. 38A-D), the coupling 1600 comprises a second end 1620 having helical threads 1626 generally extending about at least a portion of the outer surface thereof, for example, like threads on a bolt, other types of conventional coupling members, etc. Similar to the coupling 1400, the outer collar 1614 of the first end 1610 comprises a substantially smooth outer surface configured for frictional and sealing engagement with a male formatted coupling, for example which can be in the form of an ISO 80369-3 formatted coupling, or for example, can be formatted according to other coupling formats (e.g., EO, lure, lure lock, other available coupling formats, etc.). Optionally, as depicted in FIGS. 41A-D, both ends 1710, 1720 can comprise helical threads 1726 formed on the outer collars 1714, 1724 thereof.

Figure 42A:
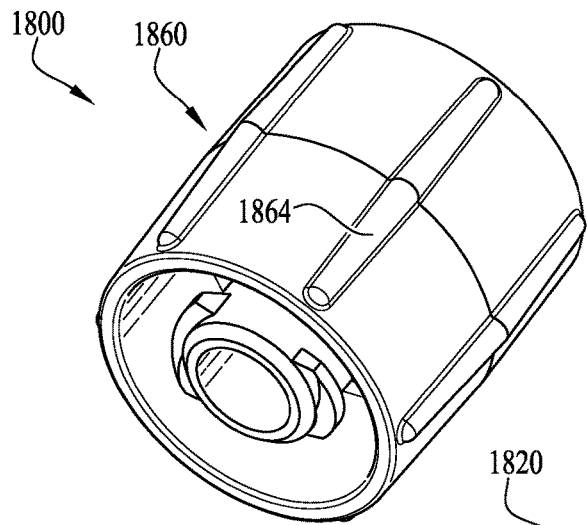
FIG. 42A shows a perspective view of an enteral coupler according to another example embodiment of the present invention.
Figure 42B:
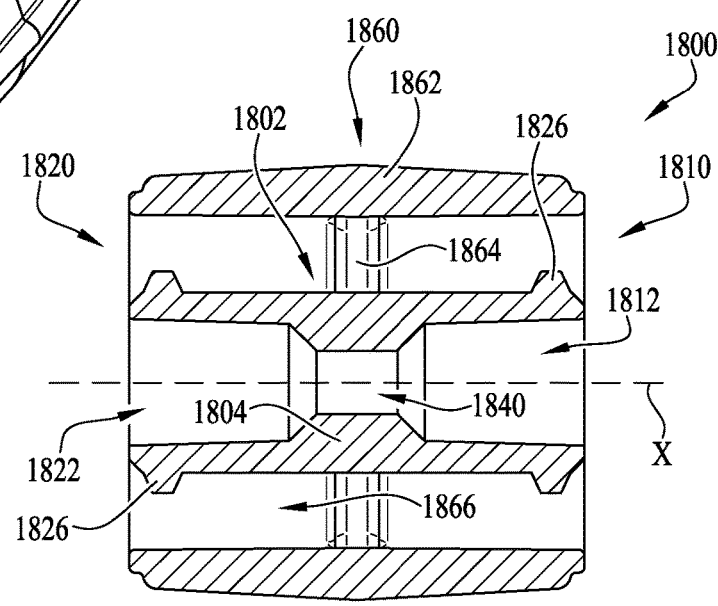
FIG. 42B shows a cross-sectional view of the enteral coupler of FIG. 42A.
Figure 42C:
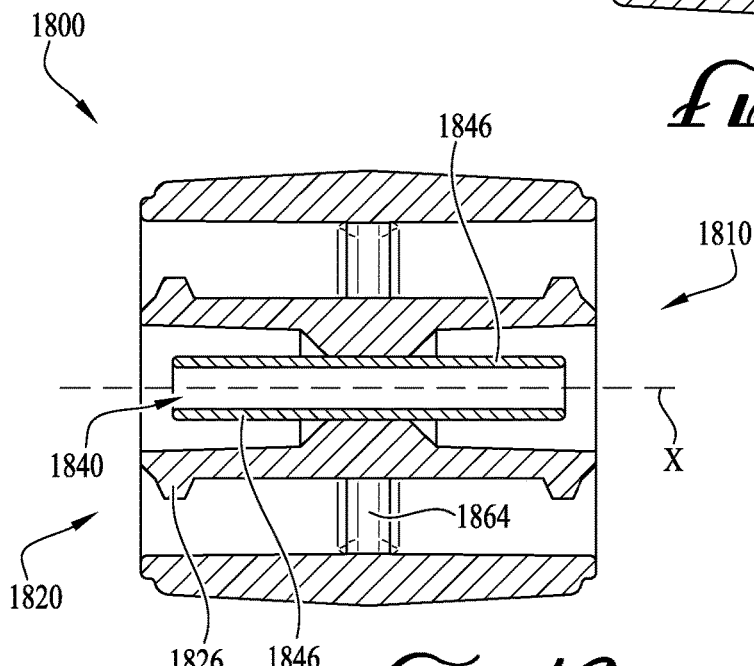
FIG. 42C shows the cross-sectional view of the enteral coupler of FIG. 42B, and further including an enteral dosing control coupling.
Figure 44A:
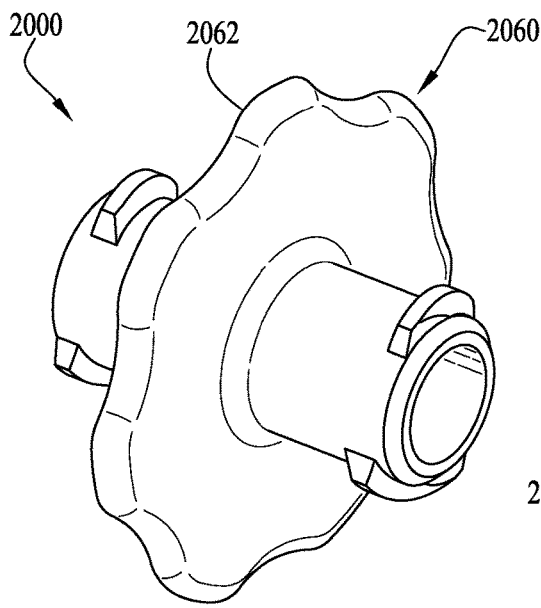
FIG. 44A shows a perspective view of an enteral coupler according to another example embodiment of the present invention.
Figure 44B:
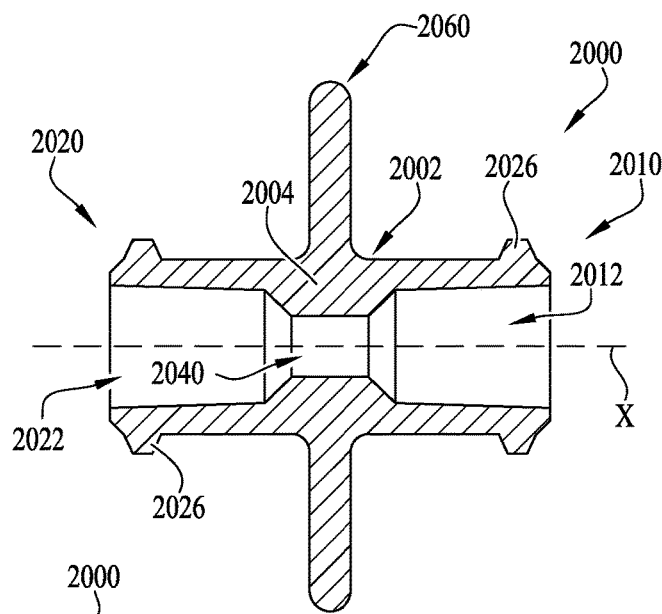
FIG. 44B shows a cross-sectional view of the enteral coupler of FIG. 44A.
Figure 44C:
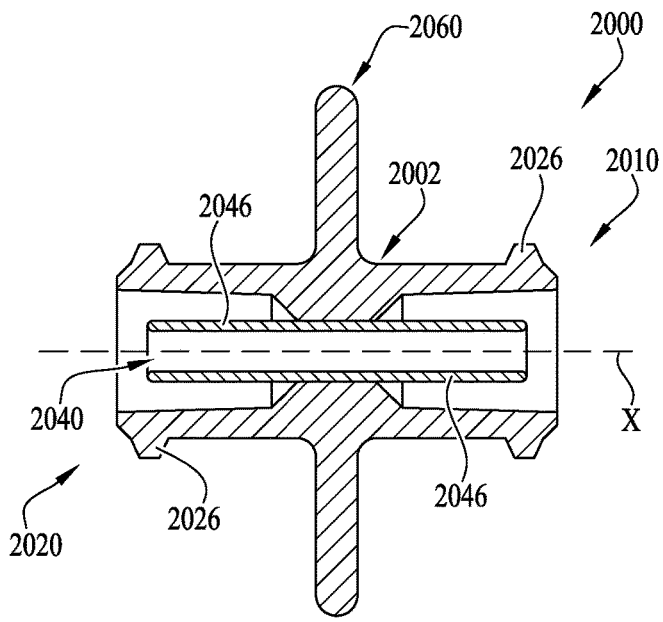
FIG. 44C shows the cross-sectional view of the enteral coupler of FIG. 44B, and further including an enteral dosing control coupling.
Figure 46A:
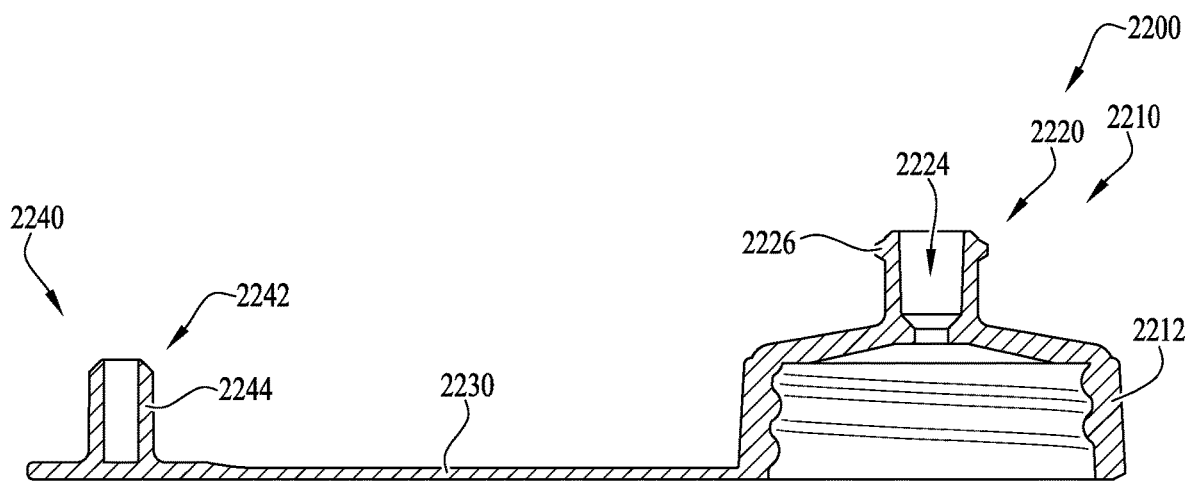
FIGS. 46A-C show cross-sectional view of a fluid transfer lid according to example embodiments of the present invention.
Figure 46B:
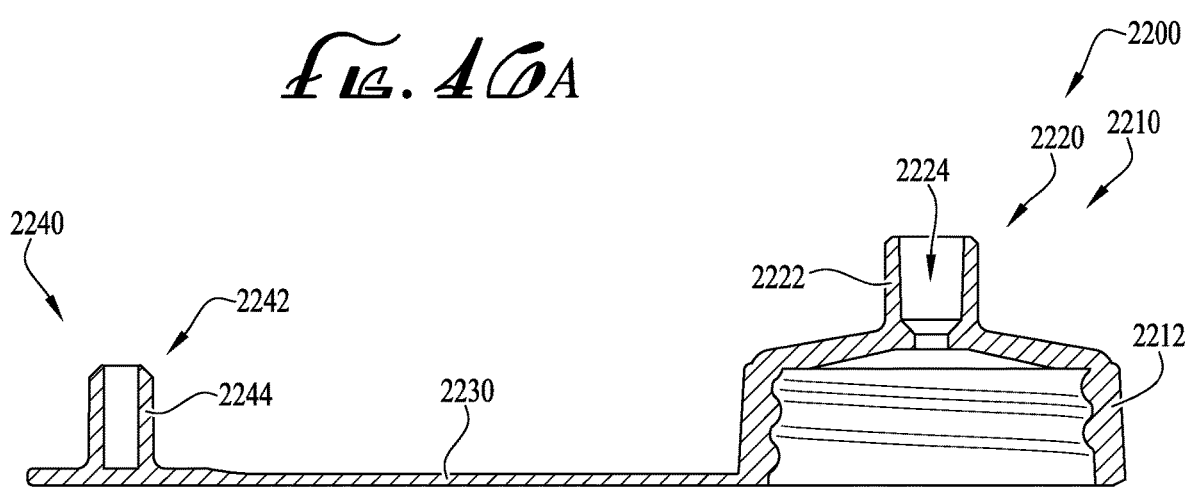
Figure 46C:
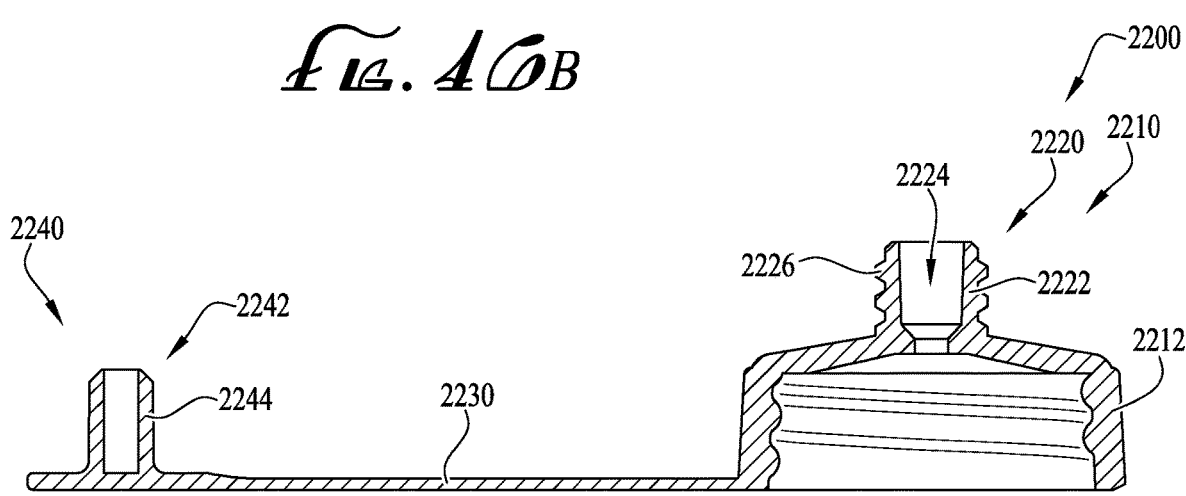

Optionally, according to another example embodiment of the present invention, the couplings as shown in FIGS. 37A-41D can further comprise one or more additional features to improve grasping or gripping the coupler during use. For example, according to one example embodiment as shown throughout FIGS. 42A-45D, the couplings 1800, 1900, 2000 and 2100 comprise one or more protrusions or helical coupling lugs 1826, 1926, 2026, 2126 projecting outwardly from the exterior surface of the collars at the first and second ends thereof. Optionally, rather than lugs projecting from the exterior surface of the collar, the exterior surface of the collar can comprise helical threads generally extending about at least a portion of the exterior surface thereof, for example, like threads on a bolt, other types of conventional coupling members, etc. In some example embodiments, the exterior surface of the collar is entirely smooth without any lugs, for example, whereby a frictional fit (as described above) will be provided between the male ISO 80369-3 formatted coupling and one of the ends of the coupling. Optionally, other coupling formats can be provided on one of the ends, for example as described above. Optionally, a lumen extension tip 1846, 1946, 2046, 2146 can be provided with one or both ends of the couplings and define a respective lumen 1840, 1940, 2040, 2140 extending therethrough. FIGS. 42A-C show a coupler 1800 comprising an outer barrel 1860 comprising one or more ribs or connecting members 1864 for generally coaxially and concentrically aligning the outer barrel 1860 with the coupling member 1802. According to example embodiments, one or more vents 1866 can be provided, for example wherein one or more of the connecting members 1864 are generally spaced apart about a circular array. According to other example embodiments, the connecting member 1864 can be substantially solid and comprise one or more holes or other openings extending entirely therethrough. According to additional example embodiments, the coupling can be configured as desired, for example, to further assist in grasping or gripping the coupler during use. According to one example embodiment, the outer barrel 1860 can be replaced with one or more gripping panels 1960 defining outer surfaces 1962 (see FIGS. 43A-D). In example embodiments, a connecting member or transverse flange 1964 generally connecting the one or more gripping panels 1960 to the coupling member 1902. U.S. patent application Ser. No. 15/185,583 discloses syringe-to-syringe couplers comprising one or more gripping panels or an outer barrel, the entirety of which is incorporated herein by reference. Optionally, one or more vents can extend through the entirety of the flange 1964.

According to another example embodiment and depicted in FIGS. 44A-D, the coupler 2000 comprises a centrally-positioned collar member or disc-shaped protrusion 2060 that extends outwardly around the entire outer periphery of the coupling member 2002 (generally about at the midpoint of the body 2004). In example embodiments, an outer surface profile 2062 can be provided, for example such as the depicted undulating pattern comprising a plurality of alternating peaks and valleys along the outer periphery of the circular profile. According to one example embodiment, the protrusion 2060 provides the user or operator a coupling which can easily be grasped by one or more fingers of the user or operator, and can be easily manipulated (e.g., rotation for attachment/detachment).

FIGS. 45A-D show a coupler 2100 comprising a tab 2160 extending from a portion of the coupling member 2102. In example embodiments, the tab 2160 is generally comprises an oval or circular outer profile 2162 or for example comprising a tear-drop shape, for example with a generally oval-shaped outer profile 2162 having one end thereof connected to the coupling member 2102. In example embodiments, the tab 2160 can comprise one or more ribs, protrusions, or other surface features 2164. According to one example embodiment, the tab 2160 can comprise an opening 2166 to function as a gripping feature, or for example, an eyelet or for engagement with a tether or other engagement feature, or for example two end caps for removable engagement with the first and second ends of the coupling 2100 (the end caps being connected to the opening 2166 by a tether). Optionally, the tab 2160 and/or gripping feature thereof can be shaped and sized as desired.

In alternate example embodiments, for example when the delivery of fluid travels in a direction such that fluid moves from a female ISO 80369-3 formatted coupling to a male ISO 80369-3 formatted coupling, an adaptor can be provided such that a syringe comprising a female ISO 80369-3 formatted coupling without the lumen extension tip extending therein is modified to have a female ISO 80369-3 formatted coupling with the lumen extension tip extending therein. For example, a first end of the adaptor can comprise a male ISO 80369-3 formatted coupling (e.g., for connecting to the female ISO 80369-3 formatted coupling) and a second end of the adaptor can comprise a modified female ISO 80369-3 formatted coupling comprising a lumen extension tip, for example, as described herein. Thus, for syringes comprising the female ISO 80369-3 formatted coupling and not comprising a lumen extension tip extending axially therein, the adaptor as described above can be connected to the syringe such that dosing inconsistencies and anomalies in accuracy during fluid delivery are further reduced, minimized or substantially eliminated.

Figure 47A:
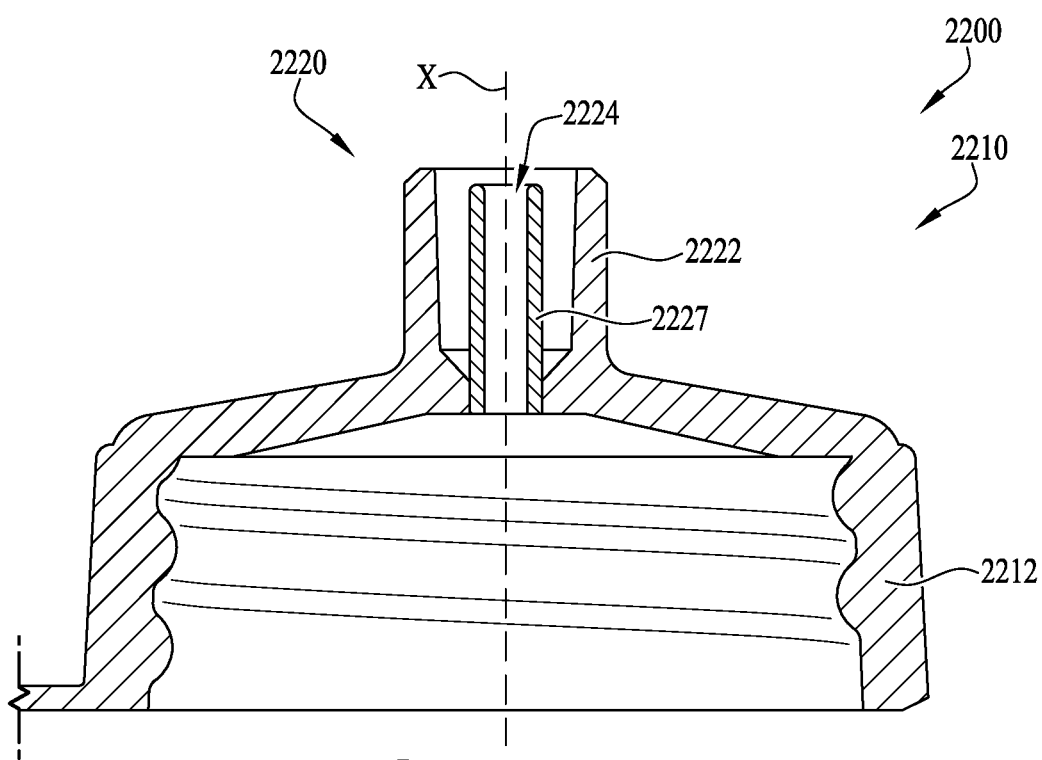
FIGS. 47A-B show a detailed cross-sectional view of the fluid transfer lid of FIG. 46B, and further including a dosing control coupling.
Figure 47B:
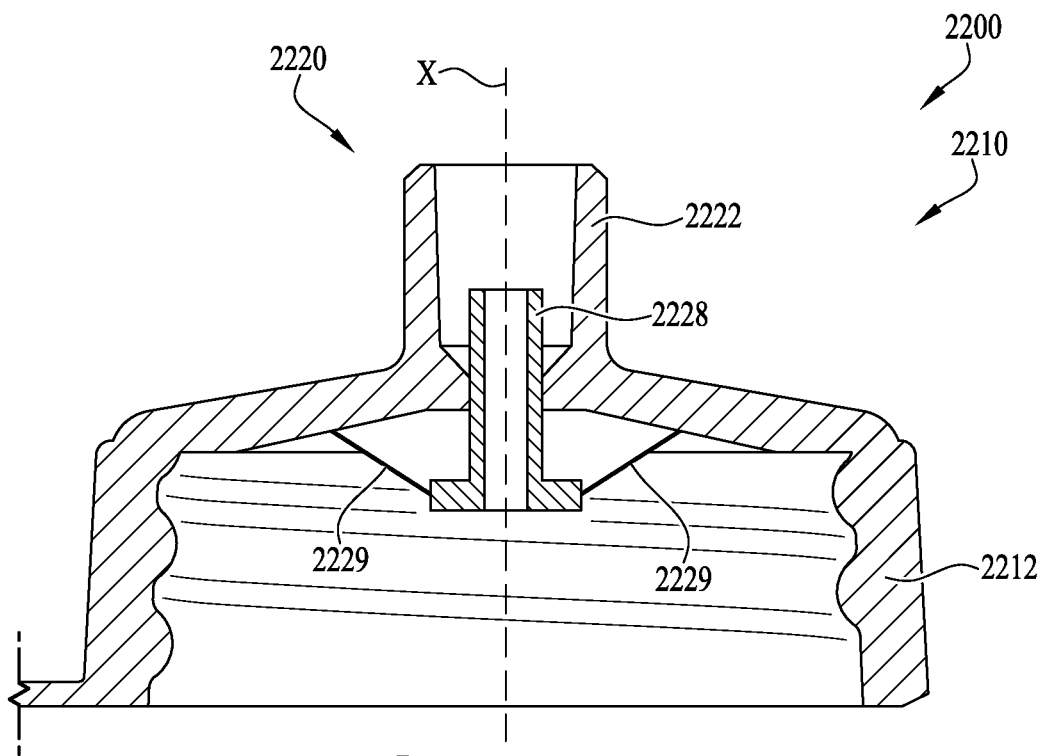
Figure 51:
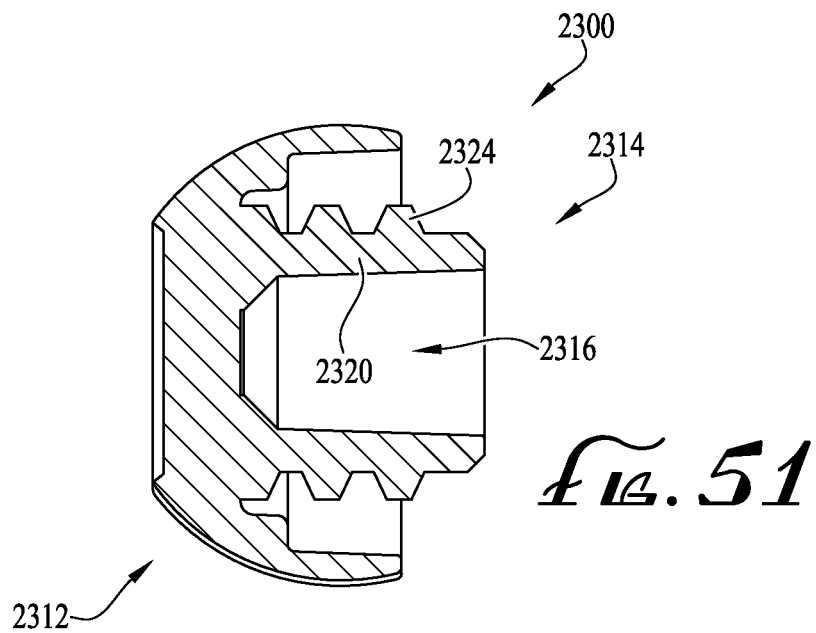
Figure 52:
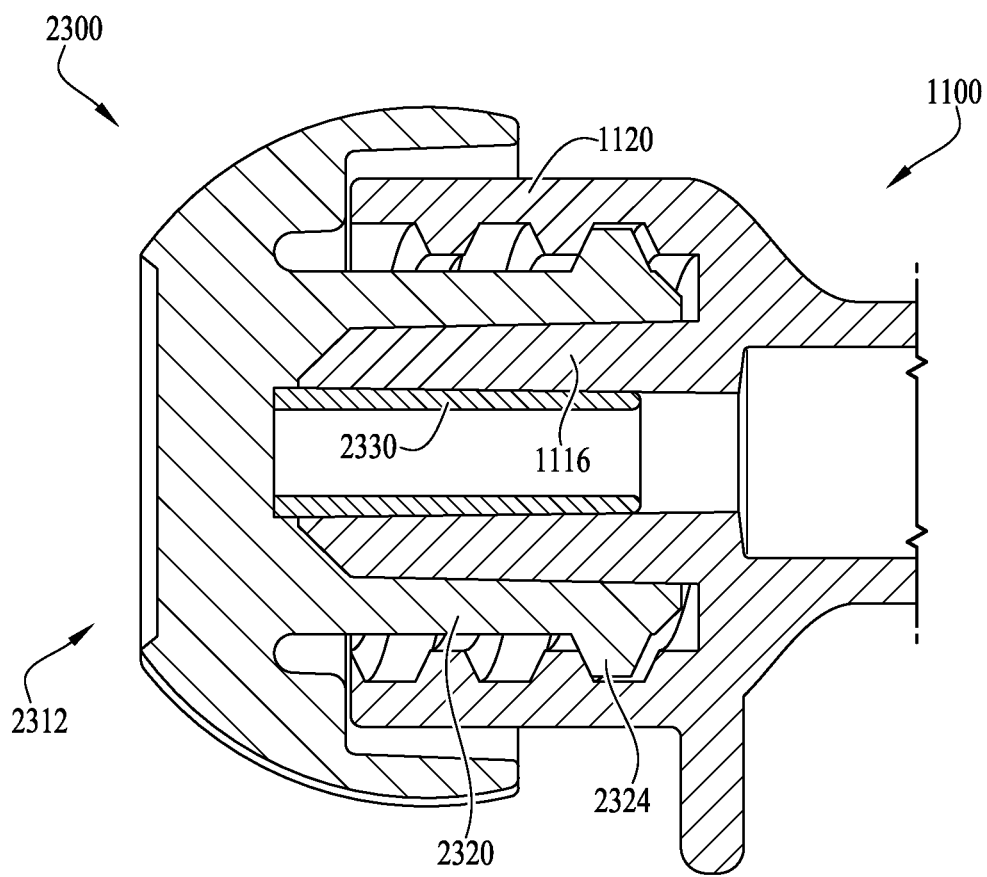
FIGS. 52-54 show cross-sectional views of a tip cap according to example embodiments of the present invention.
Figure 53:
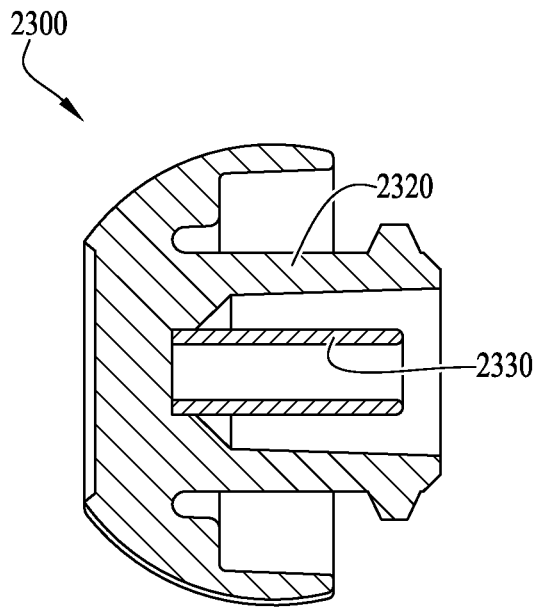
Figure 54:
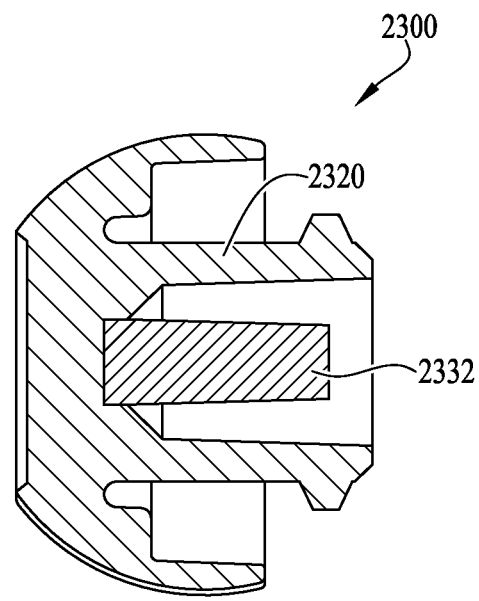

FIGS. 46A-47B show a fluid transfer lid 2200 according to another example embodiment of the present invention. In example embodiments, the transfer lid 2200 as depicted herein preferably provides for coupling engagement with a pharmacy bottle or other container comprising a liquid medicine or fluid, for example, which is to be transferred (by small or large doses) to a syringe. Thus, in example embodiments where the coupling of the syringe is in the form of a male ISO 80369-3 formatted coupling, the transfer lid 2200 for compatible engagement therewith comprises a female ISO 80369-3 formatted coupling, for example, which can comprise one or more outer ribs (see FIG. 46A), threads (see FIG. 46C), or can be substantially smooth (see FIG. 46B). As depicted in FIGS. 47A-B, a lumen extension tip 2227, 2228 can be incorporated with the female ISO 80369-3 formatted coupling. In some example embodiments, the lumen extension tip is substantially integral with the female ISO 80369-3 formatted coupling (see FIG. 47A). As depicted in FIG. 47B, a flexible membrane 2229 is attached to a separate dosing control coupling 2228, which is positioned to be biased within the internal conduit 2224 of the female coupling 2220, and wherein the membrane 2229 is generally sealed with an inner surface of the cap, and wherein the dosing control coupling 2228 remains biased to fully extend within the internal conduit of the coupling. In example embodiments, when a misconnection is attempted with the dosing control coupling, the dosing control coupling retracts as depicted in FIG. 47B, for example, such that the misconnection cannot be achieved. U.S. patent application Ser. No. 14/960,905 is incorporated herein by reference and shows transfer lids for use with enteral connectors. Optionally, the fluid transfer lid can be configured for venting, for example, to relieve any vacuum created during the transfer of fluids from the bottle attached with the fluid transfer lid. U.S. patent application Ser. No. 14/844,910 is incorporated herein by reference and discloses a transfer lid having a vented slot.

FIGS. 48-55 show a plurality of tip caps according to additional example embodiments of the present invention. As depicted and according to the embodiments of FIGS. 48-54, a tip cap 2300 extends from a first end 2312 to a second end 2314, and the second end 2314 comprises a female ISO 80369-3 formatted coupling for engagement with a male ISO 80369-3 formatted coupling, for example, with the male ISO 80369-3 formatted coupling of the syringes of FIGS. 33-35. Preferably, the tip cap can optionally comprise a dosing control coupling 2330, 2332, for example, which can be substantially solid or comprise a hollow reservoir therein, for example, for generally extending within the internal conduit of the male ISO 80369-3 formatted coupling, for example, to act as a plug, stopper or medium for preventing fluids within the syringe from further occupying the internal conduit of the male ISO 80369-3 formatted coupling. In some example embodiments, the tip caps as described herein are preferably self-righting, for example, such that the orientation of the tip cap in a rest position is generally configured such that the female ISO 80369-3 formatted coupling is generally facing upwards. In some example embodiments, the tip cap can comprise one or more vents, for example, as described in U.S. patent application Ser. No. 14/844,922, the entirety of which is incorporated herein by reference. In some example embodiments, the tip can comprise a substantially large base, for example, which can prevent the tip cap from being a choking hazard, and which can function as a stand to orient the syringe in a vertical manner when coupled thereto.

Figure 55:
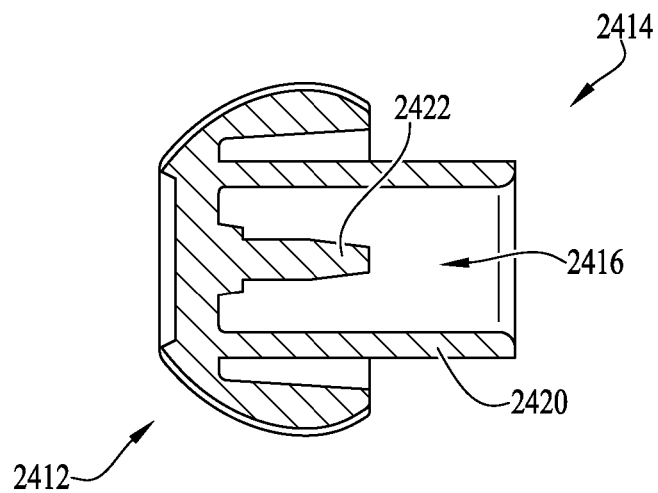
FIG. 55 shows a cross-sectional view of a tip cap according to another example embodiment of the present invention.

Optionally, as depicted in FIG. 55, the female connector of the second end 2414 is configured for engagement with a coupling format other than the ISO 80369-3 format. According to one example embodiment of the present invention, the female connector is configured for compatible coupling engagement with an end portion of an applicator or tube, for example, for capping an end portion of an applicator tube 2540 of an oral administration coupler 2500 (see FIGS. 56A-59D). Optionally, a lumen extension tip or other male projection 2422 can be provided for fitting within a lumen of the tube 2540 when the cap 2400 is engaged therewith.

In example embodiments, the oral administration coupler 2500 comprises an end for coupling to a syringe, for example, a female ISO 80369-3 formatted coupling, and another generally opposite end for delivering fluids orally to a patient, for example, within the patient's mouth. In some example embodiments, the female ISO 80369-3 formatted coupling can comprise a dosing control coupling, or for example, can be formed from two or more separate materials and comprise one or more flexible portions such that fluids can be delivered to the back of the patient's mouth. U.S. patent application Ser. No. 15/078,674 and U.S. patent application Ser. No. 15/652,742 disclose various oral administration couplers and are incorporated herein by reference in their entirety.

For example, FIGS. 56A-57D show a plurality of oral administration couplers 2500 configured for back-of-mouth delivery, which generally comprise a coupling member 2520 and a generally elongate straw or delivery tube 2540 extending from the coupling member 2520. In example embodiments, an end of the coupling member comprises a female ISO 80369-3 formatted coupling, for example, which can comprise one or more ribs 2524 (see FIGS. 56A, 56C, 57A, 57C) or can be fully threaded (see FIGS. 56B, 57B). Optionally, as depicted in FIGS. 56C and 57C, the female ISO 80369-3 formatted coupling can comprise a dosing control coupling 2521 as described above. In example embodiments, the oral delivery applicator 2540 comprises a generally elongate tube extending a length sufficient for delivering medications orally.

FIGS. 58A-59B show an oral administration coupler 2600 according to another example embodiment of the present invention. According to the depicted example embodiment, the oral administration coupler 2600 comprises a first end 2612 and a second end 2614, for example, wherein a coupling portion 2620 is provided at the second end 2614 and an applicator 2630 at the first end 2612. In example embodiments, the coupling portion 2620 comprises a female ISO 80369-3 formatted coupling and the applicator 2630 is generally elongate for assisting in the oral delivery of fluids to a patient's mouth. In example embodiments, the coupling portion 2620 comprises a collar 2622, a hollow internal chamber 2617, one or more protrusions 2624 formed on an outside surface of the collar 2622, and a lumen 2616 extending entirely from the first end 2612 to the second end 2614.

According to example embodiments, the coupling portion 2622 can optionally comprise helical threads 2624 on an outside surface of the collar 2624 (see FIG. 58B, 59B) as similarly described above, or for example can comprise a lumen extension tip 2623 axially extending within the hollow internal chamber 2617 of the collar 2622. According to example embodiments, an outer flange 2640 can be formed with the coupler 2600 as desired. According to one example embodiment, the flange 2640 is configured to mitigate choking risks. U.S. patent application Ser. No. 15/652,742 shows a plurality of oral administration couplers, the entirety of which is incorporated herein by reference.

While the invention has been described with reference to example embodiments, it will be understood by those skilled in the art that a variety of modifications, additions and deletions are within the scope of the invention, as defined by the following claims.

What is claimed is:

1. An enteral syringe comprising:
a hollow syringe barrel adapted to receive a plunger for retraction and advancement within the syringe barrel to transfer a delivered fluid to and from a contained volume of the syringe barrel; and
a dosing control coupling extending along an elongate axis from a first end to a second end, the first end comprising a female ISO 80369-3 formatted coupling comprising a cylindrical outer collar defining an internal chamber and a lumen extension tip projecting axially into the internal chamber of the cylindrical outer collar, wherein the lumen extension tip has an axial length that is shorter than an axial length of the cylindrical outer collar, the second end comprising an end coupling for engagement with the syringe barrel, wherein the dosing control coupling is configured for coupling engagement with a male ISO 80369-3 formatted coupling comprising a male coupling hub defining a cavity or lumen extending at least partially therethrough, and wherein coupling engagement of the dosing control coupling with the male coupling hub of the male ISO 80369-3 formatted coupling is configured such that the lumen extension tip of the dosing control coupling provides a clearance fit within the cavity or lumen of the male coupling hub when the male coupling hub is coupled with the cylindrical outer collar of the female ISO 80369-3 formatted coupling, further comprising helical external coupling members formed on a portion of the cylindrical collar.

2. The enteral syringe of claim 1, wherein the dosing control coupling is formed separately from the syringe barrel and is configured for attachment to the syringe barrel.

3. The enteral syringe of claim 2, wherein the dosing control coupling is permanently attached to the hollow syringe barrel.

4. The enteral syringe of claim 3, wherein the dosing control coupling is configured for removable attachment with the hollow syringe barrel.

5. The enteral syringe of claim 1, wherein the dosing control coupling is formed integrally with the hollow syringe barrel.

6. The enteral syringe of claim 1, wherein the lumen extension tip is formed integrally with the dosing control coupling.

7. The enteral syringe of claim 1, wherein the lumen extension tip is a separate piece and configured for removable coupling engagement with the dosing control coupling.

8. The enteral syringe of claim 1, further comprising a flange extending around the entirety of a periphery of the dosing control coupling.

9. The enteral syringe of claim 8, wherein the flange extends outwardly around the entirety of a periphery of the cylindrical outer collar.

10. The enteral syringe of claim 1, wherein the cylindrical outer collar of the first end comprises an internal diameter and the lumen extension tip comprises an outer diameter, and wherein the internal diameter of the cylindrical outer collar is greater than the outer diameter of the lumen extension tip.

11. The enteral syringe of claim 1, wherein the clearance fit defines a separation of between about 0.40 mm and about 0.05 mm between the outer surface of the lumen extension tip of the dosing control coupling and the inner surface of the cavity or lumen of the male coupling hub.

12. An enteral syringe comprising:
a hollow cylindrical syringe barrel adapted to receive a plunger for retraction and advancement within the syringe barrel to transfer a delivered fluid to and from a contained volume of the syringe barrel; and
a dosing control coupling comprising a cylindrical collar defining a hollow internal chamber comprising an internal diameter and having a smooth interior surface, and a lumen extension tip defining a cylindrical body comprising an outer diameter having a smooth outer surface and comprising an internal lumen extending axially through the cylindrical body, the lumen extension tip being positioned concentrically and coaxially within the cylindrical collar such that the generally cylindrical body projects axially into the hollow internal chamber, and at least a portion of the outer diameter of the lumen extension tip being about 2.5 millimeters, wherein the lumen extension tip has an axial length that is shorter than an axial length of the cylindrical collar, further comprising helical external coupling members formed on a portion of the cylindrical collar,
wherein the internal diameter of the cylindrical collar is greater than the outer diameter of the cylindrical body of the lumen extension tip such that a space defined therebetween forms a receiver for receiving a cooperating portion of a compatible coupling element, and wherein the dosing control coupling is configured such that, upon engagement of the dosing control coupling with the cooperating portion of the compatible coupling element, the hollow internal chamber is occupied by the cooperating portion of the compatible coupling element, from the smooth interior surface of the cylindrical collar to the smooth outer surface of the lumen extension tip, with an inner surface of the cooperating portion of the compatible coupling element providing a clearance fit with the smooth outer surface of the lumen extension tip.

13. The enteral syringe of claim 12, wherein the compatible coupling element comprises a male ISO 80369-3 compatible coupling comprising a hub centrally positioned therein and defining an internal conduit extending therethrough.

14. The enteral syringe of claim 13, wherein the lumen extension tip is sized, shaped and positioned within the cylindrical collar for compatible fitting engagement within the internal conduit of the hub of the male ISO 80369-3 compatible coupling.

15. The enteral syringe of claim 12, wherein the lumen extension tip defines a contained volume of between about 0.005 milliliters to about 0.03 milliliters.

16. The enteral syringe of claim 15, wherein the lumen extension tip defines a contained volume of about 0.01 milliliters.

17. The enteral syringe of claim 12, wherein the lumen extension tip is integrally formed with the cylindrical collar.

18. The enteral syringe of claim 12, wherein the cylindrical collar is generally sized and shaped according to the ISO 80369-3 standard.

19. The enteral syringe of claim 18, further comprising a plunger axially movable within the barrel to fill and dispense fluid into and from the syringe, the plunger comprising an elongate body comprising a forward end having a spear-like tip, the spear-like tip being insertable within the internal lumen of the lumen extension tip such that a contained volume within the internal lumen of the lumen extension tip is substantially zero, and thus, dosing inconsistencies and anomalies in accuracy during fluid delivery are substantially eliminated.

20. An enteral syringe comprising:
a hollow cylindrical syringe barrel adapted to receive a plunger for retraction and advancement within the syringe barrel to transfer a delivered fluid to and from a contained volume of the syringe barrel; and
a dosing control coupling comprising a female ISO 80369-3 formatted coupling comprising a cylindrical collar defining a hollow internal chamber comprising an internal diameter and having a smooth interior surface, and a lumen extension tip comprising an elongate and cylindrical body projecting axially into the hollow internal chamber between a base portion and an end tip portion, the base portion engaged with a surface defined by the hollow internal chamber and the end tip portion generally oppositely extending therefrom, the end tip portion being recessed between 0.45-0.65 millimeters below an end portion of the cylindrical collar, the elongate and cylindrical body comprising a maximum outer diameter, and further comprising helical external coupling members formed on a portion of the cylindrical collar,
wherein an internal conduit extends entirely through the elongate and cylindrical body, wherein the elongate and cylindrical body is configured for compatible fitting engagement within an internal conduit of a male hub of an ISO 80369-3 compatible male ENFit coupling, the internal conduit of the male hub comprising a maximum internal diameter, and wherein the maximum outer diameter of the elongate and cylindrical body is less than or equal to the maximum internal diameter of the internal conduit of the male hub of the ISO 80369-3 compatible male ENFit coupling such that there is a space between an outer surface of the elongate and cylindrical body and an inner surface of the internal conduit of the male hub.

* * * * *